(12) United States Patent
Diskin et al.

(10) Patent No.: US 12,173,052 B2
(45) Date of Patent: Dec. 24, 2024

(54) HIV-1 GP120 CD4 BINDING SITE ANTIBODIES TARGETING HIV ESCAPE MUTANTS

(71) Applicants: The Rockefeller University, New York, NY (US); California Institute of Technology, Pasadena, CA (US)

(72) Inventors: Ron Diskin, Pasadena, CA (US); Anthony P. West, Pasadena, CA (US); Michel Nussenzweig, New York, NY (US); Pamela J. Bjorkman, La Canada, CA (US)

(73) Assignees: The Rockefeller University, New York, NY (US); California Institute of Technology, Pasadena, CA (US)

( * ) Notice: Subject to any disclaimer, the term of this patent is extended or adjusted under 35 U.S.C. 154(b) by 355 days.

(21) Appl. No.: 17/500,171

(22) Filed: Oct. 13, 2021

(65) Prior Publication Data
US 2022/0169707 A1  Jun. 2, 2022

Related U.S. Application Data

(63) Continuation of application No. 15/835,319, filed on Dec. 7, 2017, now Pat. No. 11,149,081, which is a continuation of application No. 13/924,469, filed on Jun. 21, 2013, now Pat. No. 9,879,068.

(60) Provisional application No. 61/662,594, filed on Jun. 21, 2012.

(51) Int. Cl.
C07K 16/10 (2006.01)
A61K 39/00 (2006.01)

(52) U.S. Cl.
CPC ...... *C07K 16/1063* (2013.01); *C07K 16/1045* (2013.01); *A61K 2039/505* (2013.01); *A61K 2039/507* (2013.01); *A61K 2039/545* (2013.01); *C07K 2317/567* (2013.01); *C07K 2317/76* (2013.01); *C12N 2740/16111* (2013.01); *C12N 2740/16122* (2013.01)

(58) Field of Classification Search
CPC ................................................ C07K 16/1063
See application file for complete search history.

(56) References Cited

U.S. PATENT DOCUMENTS

| | | | |
|---|---|---|---|
| 5,229,275 A | 7/1993 | Goroff | |
| 5,545,806 A | 8/1996 | Lonberg et al. | |
| 5,545,807 A | 8/1996 | Surani et al. | |
| 5,567,610 A | 10/1996 | Borrebaeck et al. | |
| 5,569,825 A | 10/1996 | Lonberg et al. | |
| 5,591,669 A | 1/1997 | Krimpenfort et al. | |
| 5,641,870 A | 6/1997 | Rinderknecht et al. | |
| 9,695,230 B2 | 7/2017 | Kwong et al. | |
| 9,879,068 B2 * | 1/2018 | Diskin | C07K 16/1045 |
| 10,035,844 B2 | 7/2018 | Kwong et al. | |
| 11,149,081 B2 * | 10/2021 | Diskin | A61P 31/18 |
| 2009/0053220 A1 | 2/2009 | Duensing et al. | |
| 2012/0288502 A1 | 11/2012 | Diskin et al. | |
| 2013/0209454 A1 | 8/2013 | Diskin et al. | |

FOREIGN PATENT DOCUMENTS

| | | |
|---|---|---|
| WO | 93/19786 A1 | 10/1993 |
| WO | 97/17852 A1 | 5/1997 |
| WO | 2012158948 A1 | 11/2012 |
| WO | 2013/86533 A1 | 6/2013 |
| WO | 2013/090644 A2 | 6/2013 |

OTHER PUBLICATIONS

Li, L., et al., 2019, AbRSA: A robust tool for antibody numbering, Prot. Sci. 28:1524-1531.*
Dondelinger, M., et al., Oct. 2018, Understanding the Significance and Implications of Antibody Numbering and Antigen-Binding Surface/Residue Definition, Front. Immunol. 9:Article 2278, pp. 1-15.*
Edwards, B. M., et al., 2003, The Remarkable Flexibility of the Human Antibody Repertoire; Isolation of Over One Thousand Different Antibodies to a Single Protein, BLyS, J. Mol. Biol. 334:103-118.*
Nezlin, R., 2001, Combinatorial Events in Generation of Antibody Diversity, Combinatorial Chem. High Throughput Screening, 4:377-383.*
Winkler, K., et al., 2000, Changing the Antigen Binding Specificity by Single Point Mutations of an Anti-p24 (HIV-1) Antibody, J. Immunol. 165:4505-4514.*
Yuan, W., and C. R. Parrish, 2000, Comparison of Two Single-Chain Antibodies That Neutralize Canine Parvovirus: Analysis of an Antibody-Combining Site and Mechanisms of Neutralization, Virol. 269:471-480.*
Diskin, R., et al., Dec. 2011, Increasing the potency and breadth of an HIV antibody by using structure-based rational design, Science 334:1289-1294.*
Dondelinger, M., et al., Oct. 2018, Understanding the Significance and Implications of Antibody Numbering and Antigen-Binding Surface/Residue Definition, Front. Immnol. 9:article 22, pp. 1-15.
Wu, X., et al., Sep. 2011, Focused evolution of HIV-1 neutralizing antibodies revealed by structures and deep sequencing, Science 333: 1593-1603.
Abhinandan, K.R., et al.; "Analysis and improvements to Kabat and structurally correct numbering of antibody variable domains"; Molecular Immunology, 45; 2008; pp. 3832-3839.
Akers and Defilippis, 2000, Peptides and Proteins as Parenteral Solutions. In: Pharmaceutical Formulation Development of Peptides and Proteins. Philadelphia, PA: Taylor and Francis; pp. 145-177.

(Continued)

*Primary Examiner* — Jeffrey S Parkin
(74) *Attorney, Agent, or Firm* — Fox Rothschild LLP

(57) ABSTRACT

Embodiments of the present invention are directed to compositions and methods for anti-HIV (anti-CD4 binding site) broadly neutralizing antibodies having improved potency and breadth for neutralizing a range of HIV strains. Combinations of broadly neutralizing antibodies can also improve potency over a single antibody composition.

6 Claims, 46 Drawing Sheets
(1 of 46 Drawing Sheet(s) Filed in Color)
Specification includes a Sequence Listing.

(56) References Cited

OTHER PUBLICATIONS

Akers, Michael J. et al.; "Formulation Development of Protein Dosage Forms"; Development and Manufacture of Protein Pharmaceuticals; 2002; Pharm. Biotechnol. 14; pp. 47-127.
Bruggemann, Marianne et al.; "Designer Mice: The Production of Human Antibody Repertoires in Transgenic Animals"; Generation of Antibodies by Cell and Gene Immortalization; Year in Immuno.; 1993; vol. 7; pp. 33-40.
Casadevall, Arturo; "Antibodies for defense against biological attack"; Nature Biotechnology; vol. 20; Feb. 2002; p. 114.
Casson, Lawrence P., et al., "Random Mutagenesis of Two Complementarity Determining Region Amino Acids Yields an Unexpectedly High Frequency of Antibodies with Increased Affinity for Both Cognate Antigen and Autoantigen," J. Exp. Med., vol. 182, Sep. 1995, pp. 743-750.
Diskin, Ron, et al., "Restricting HIV-1 pathways for escape using rationally designed anti-HIV-1 antibodies," Journal of Experimental Medicine, vol. 210, May 27, 2013, pp. 1235-1249.
Diskin, Ron et al.; "Structure of a Glade C HIV-1 gp120 bound to CD4 and CD4-induced antibody reveals anti-CD4 polyreactivity"; Nature Structural & Molecular Biology; vol. 17; No. 5; May 2010; pp. 608-613.
Diskin, Ron et al.; "Increasing the Potency and Breadth of an HIV Antibody by Using Structure-Based Rational Design"; Science; vol. 334; Dec. 2, 2011; pp. 1289-1293.
Igarashi, Tatsuhiko et al.; "Human immunodeficiency virus type 1 neutralizing antibodies accelerate clearance of cell-free virions from blood plasma"; Nature Medicine; vol. 5, No. 2; Feb. 1999; pp. 211-216.
Jakobovits, Aya et al.; "Germ-line transmission and expression of a human-derived yeast artificial chromosome"; Letters to Nature; vol. 362; Mar. 18, 1993; pp. 255-258.
Jakobovits, Aya et al.; "Analysis of homozygous mutant chimeric mice: Deletion of the immunoglobulin heavy-chain joining region blocks B-cell development and antibody production"; Proc. Natl. Acad. Sci. USA; Genetics; vol. 90; Mar. 1993; pp. 2551-2555.
Jones, Peter T. et al.; "Replacing the complementarity-determining regions in a human antibody with those from a mouse"; Nature; vol. 321; May 29, 1986; pp. 522-525.
Keller, Margaret A. et al.; "Passive Immunity in Prevention and Treatment of Infectious Diseases"; Clinical Microbiology Reviews; 2000; vol. 13; No. 4; pp. 602-614.
Klein, Florian et al., "HIV therapy by a combination of broadly neutralizing antibodies in humanized mice," Nature, vol. 492, Dec. 5, 2012, pp. 118-122.
McGoff and Scher, 2000, Solution Formulation of Proteins/Peptides: In McNally, E.J., ed. Protein Formulation and Delivery. New York, NY: Marcel Dekker; pp. 139-158.
Montefiori, David C.; "Evaluating Neutralizing Antibodies Against HIV, SIV, and SHIV in Luciferase Reporter Gene Assays"; Basic Protocol 1; Detection and Analysis of HIV; Current Protocols in Immunology; Chapter 12; Unit 12.11; 2004; 17pp.
Mouquet, Hugo, et al., "Enhanced HIV-1 neutralization by antibody heteroligation," PNAS, vol. 109, No. 3, Jan. 17, 2012, pp. 875-880.
Nakamura, Kyle J., "Coverage of primary mother-to-child HIV transmission isolates by second-generation broadly neutralizing antibodies," AIDS, vol. 27, 2013, pp. 337-346.
Neumann, Thomas et al., "T20-insensitive HIV-1 from naïve patients exhibits high viral fitness in a novel dual-color competition assay on primary cells," Virology, vol. 333, 2005, pp. 251-262.
Reichmann, Lutz et al.; "Reshaping human antibodies for therapy"; Nature; vol. 332; Mar. 24, 1988; pp. 323-327.
Sambrook, J., et al. (2001) Molecular Cloning, A Laboratory Manual, Cold Spring Harbor Press, Plainview, N.Y.
Sather, D. Noah. et al.; "Broadly Neutralizing Antibodies Developed by an HIV-Positive Elite Neutralizer Exact a Replication Fitness Cost on the Contemporaneous Virus"; Journal of Virology; vol. 86; No. 23; Dec. 2012; pp. 12676-12685.
Scheid, Johannes F. et al., "A method for identification of HIV gp140 binding memory B cells in human blood," Journal of Immunological Methods, vol. 343, 2009, pp. 65-67.
Scheid, Johannes F. et al.; "Sequence and Structural Convergence of Broad and Potent HIV Antibodies That Mimic CD4 Binding"; Science; vol. 333; Sep. 16, 2011; pp. 1633-1637.
Shibata, Riri et al.; "Neutralizing antibody directed against the HIV-1 envelope glycoprotein can completely block HIV-1/SIV chimeric virus infections of macaque monkeys"; Nature Medicine; vol. 5; No. 2; Feb. 1999; pp. 204-210.
Verhoeyen, Martine et al.; "Reshaping Human Antibodies: Grafting an Antilysozyme Activity"; Science; vol. 239; 1988; pp. 1534-1536.
Walker, Laura M. et al.; "Broad and Potent Neutralizing Antibodies from an African Donor Reveal a New HIV-1 Vaccine Target"; Science; vol. 326; Oct. 9, 2009; pp. 285-289.
Walker, Laura M. et al.; "Broad neutralization coverage of HIV by multiple highly potent antibodies"; Nature; 2011; 6pp.
Weins, Gregory D., et al., "Mutation of a Single Conserved Residue in VH Complementarity-Determining Region 2 Results in a Severe Ig Secretion Defect," Journal of Immunology, 2001, 167(3), pp. 2179-2186.
West, Jr., Anthony P. et al., "Structural basis for germ-line gene usage of a potent class of antibodies targeting the CD4-binding site of HIV-1 gp120"; PNAS; Jun. 27, 2012; pp. E2083-E2090.
Wu, Xueling et al.; "Rational Design of Envelope Identifies Broadly Neutralizing Human Monoclonal Antibodies to HIV-1"; Science; vol. 329; Aug. 13, 2010; pp. 856-861.
Zhou, Tongqing et al.; "Structural Basis for Broad and Potent Neutralization of HIV-1 by Antibody VRC01"; Science; vol. 329; Aug. 13, 2010; pp. 811-817.
Written Opinion and International Search Report issued in corresponding PCT Application No. PCT/US2013/047183; mailed Oct. 24, 2013; 13pp.
Caskey et al., "Broadly neutralizing anti-HIV-1 monoclonal antibodies in the clinic", Nature Medicine, vol. 25, 2019, pp. 547-553.
Dashti et al., "Broadly Neutralizing Antibodies against HIV: Back to Blood", Trends in Molecular Medicine, vol. 25, No. 3, 2019.
McCoy, "The expanding array of HIV broadly neutralizing antibodies", Retrovirology, 2018, 15:70.
Parsons et al., "Importance of Fc-mediated functions of anti-HIV-1 broadly neutralizing antibodies", Retrovirology, 2018, 15:58.
Possas et al., "HIV cure: global overview of bNAbs' patents and related scientific publications", Expert Opinion on Therapeutic Patents, 2018, vol. 28, No. 7, pp. 551-560.
Sok et al., "Recent progress in broadly neutralizing antibodies to HIV", Nature Immunology, 2018, vol. 19, pp. 1179-1188.
Liu et al., "Broadly neutralizing antibodies for HIV-1: effecacies, challenges and opportunities", Emerging Microbes & Infections, 2020, vol. 9.
Mahomed et al., "Clinical Trials of Broadly Neutralizing Monoclonal Antibodies for Human Immunodeficiency Virus Prevention: A Review", The Journal of Infectious Diseases, 2021, 13;223(3), pp. 370-380.

\* cited by examiner

FIG. 1

| Mutant | Heavy chain | | Light chain | |
|---|---|---|---|---|
| 45-46m2 | G54W | | S28Y | |
| 45-46m4 | G54W | | S28Y | Y89N |
| 45-46m5 | G54W | | S28Y | Y89S |
| 45-46m6 | G54W | | S28Y | Y89T |
| 45-46m7 | G54W | W47V | S28Y | |
| 45-46m8 | G54W | W47A | S28Y | |
| 45-46m9 | G54W | W47L | S28Y | |
| 45-46m16 | G54W | W102H | S28Y | |
| 45-46m17 | G54W | W102N | S28Y | |
| 45-46m18 | G54W | W102S | S28Y | |
| 45-46m20 | G54W | W102F | S28Y | |
| 45-46m21 | G54W | W102L | S28Y | |
| 45-46m22 | G54W | W102T | S28Y | |

| Mutant | Heavy chain | | Light chain | |
|---|---|---|---|---|
| 45-46m23 | G54W | W102C | S28Y | |
| 45-46m24 | G54W | W47F | S28Y | |
| 45-46m25 | G54W | W47I | S28Y | |
| 45-46m26 | G54W | W47H | S28Y | |
| 45-46m28 | G54W | W47T | S28Y | |
| 45-46m29 | G54W | W102A | S28Y | |
| 45-46m30 | G54W | Y100N | S28Y | |
| 45-46m31 | G54W | Y100S | S28Y | |
| 45-46m32 | G54W | Y100K | S28Y | |
| 45-46m34 | G54W | | S28Y | Y89A |
| 45-46m35 | G54W | | S28Y | Y89G |
| 45-46m36 | G54W | | S28Y | Y89D |

FIG. 3

| Virus ID | Clade | NIH45-46 | NIH45-46[G54W] | 45-46m2 | 45-46m7 |
|---|---

FIG. 5B

| Virus ID | VRC01 | NIH45-46$^{G54W}$ | 45-46m2 | 45-46m7 |
|---|---|---|---|---|
| VC10042.y19.72 | >50 | 5.8 | 0.66 | 2.32 |
| VC10042.y19.101 | >50 | 7.9 | <0.39 | 1.06 |
| VC10042.y19.113 | >50 | 7.4 | <0.39 | 0.64 |
| VC10042.y19.205 | >50 | 6.9 | 0.46 | 0.69 |
| VC10042.y22.01 | >50 | 4.65 | 1.22 | 1.13 |
| VC10042.y22.02 | >50 | >50 | 2.2 | 12.36 |
| VC10042.y22.03 | >50 | 2.67 | 1.21 | 1.11 |
| VC10042.y22.04 | >50 | >50 | 3.37 | 14.45 |
| VC10042.y22.05 | >50 | >50 | 2.21 | 8.83 |
| VC10042.y22.06 | >50 | 12.7 | 0.47 | 0.61 |
| VC10042.y22.07 | >50 | >50 | 2.74 | 10.54 |
| VC10042.y22.08 | 1.71 | 9.73 | <0.39 | <0.39 |

| IC$_{50}$ values (μg/ml) | >50 | 10-50 | 1-10 | 0.1-1 | <0.1 |

Bound to NIH45-46
Bound to 45-46m2

| Envelope | Antibody | | | | |
|---|---|---|---|---|---|
| | NIH45-46$^{G54W}$ | 45-46m2 | 45-46m7 | 45-46m25 | 45-46m28 |
| YU-2 | 0.008 | 0.005 | 0.009 | 0.005 | 0.003 |
| YU-2$^{N279K}$ | >50 | 20 | 2.41 | 2.59 | 0.65 |
| YU-2$^{N279H}$ | >50 | 0.452 | 0.245 | Not Tested | Not Tested |
| YU-2$^{N280D}$ | >50 | 0.435 | 0.139 | 0.190 | 0.096 |
| YU-2$^{N280Y}$ | >50 | 2.23 | 0.005 | 0.004 | 0.009 |
| YU-2$^{A281T}$ | ~0.1/>50* | ~0.1/>50* | ~0.1/>50* | ~0.1/>50* | ~0.1/>50* |
| YU-2$^{R456W}$ | 5.67 | 0.032 | 0.035 | 0.075 | 0.059 |
| YU-2$^{G458D}$ | 28 | 0.004 | 0.001 | 0.002 | 0.003 |
| YU-2$^{G459D}$ | 0.01 | 0.007 | 0.003 | 0.003 | 0.003 |

FIG. 12A

| Strain | 279 | Glycosylation Potential |
|---|---|---|
| YU2 | NFTNNAKTI | --- |
| YU2-A281T | NFTNNTKTI | 0.6096 |
| YU2-A281S | NFTNNSKTI | 0.5402 |
| CY122 | NFTNDSKII | 0.4922 |
| 06CM-U14842 | SDSNTSGDL | 0.4431 |
| 99CMA121 | NITNNSKNI | 0.5188 |

FIG. 12B

IC$_{50}$ values (µg/ml)

| Strain | NIH45-46$^{G54W}$ | 45-46m2 | 45-46m7 |
|---|---|---|---|
| YU2$^{N276S}$ | 0.004 | 0.006 | 0.003 |
| YU2$^{T278A}$ | 0.001 | 0.001 | 0.001 |

FIG. 15

IC$_{50}$ Values (µg/ml)

| Virus ID | Clade* | NIH45-46 | NIH45-46 | 45-46m2 | 45-46m7 | 45-46m25 | 45-46m28 |
|---|---|---|---|---|---|---|---|
| T278-50 | CRF02_AG | >50 | >50 | >50 | >50 | >50 | >50 |
| 89-F1_2_25 | CD | >50 | >50 | >50 | >50 | >50 | >50 |
| 6540.v4.c1 | AC | >50 | >50 | >50 | >50 | >50 | |
| Ce1172_H1 | C (T/F) | >50 | >50 | >50 | >50 | >50 | >50 |
| 620345.c01 | CRF01_AE | >50 | >50 | >50 | >50 | >50 | >50 |
| X2088_c9 | G | >50 | >50 | >50 | >50 | >50 | |
| Du422.1 | C | >50 | >50 | 8.473 | 1.647 | 2.572 | |
| 3817.v2.c59 | CD | >50 | >50 | 5.138 | >50 | >50 | >50 |
| CAP210.2.00.E8 | C | >50 | >50 | 1.945 | | | |
| CAP45.2.00.G3 | C | >50 | | | | 1.456 | |
| 6545.v4.c1 | AC | >50 | | | | 4.636 | |
| 211-9 | CRF02_AG | >50 | | | | | 8.414 |
| Du172.17 | C | >50 | 3.65 | | | 3.548 | |
| 3016.v5.c45 | D | >50 | 1.47 | | | | |
| T250-4 | CRF02_AG | >50 | 1.33 | 1.554 | | 8.488 | |
| 246F C1G | C (T/F) | >50 | | | | | |
| CNE20 | BC | 7.83 | | | | | |
| CNE21 | BC | 6.01 | | | | | |
| HIV-16845-2.22 | C | 5 | | | | | |
| C2101.c01 | CRF01_AE | 4.24 | | | | | |
| ZM247v1(Rev-) | C (T/F) | 2.94 | | | | | |
| ZM233M.PB6 | C | 2.5 | | | | | |
| C1080.c03 | CRF01_AE | 2.48 | | | | | |
| THRO4156.18 | B | 1.91 | | | | | |
| 3103.v3.c10 | ACD | 1.77 | | | | | |
| 231966.c02 | D | 1.64 | | | | | |
| TRO.11 | B | 1.61 | | | | | |
| T251-18 | CRF02_AG | 1.35 | | | | | |
| Ce1176_A3 | C (T/F) | | | | | | |
| BJOX010000.06.2 | CRF01_AE (T/F) | | | 1.382 | 1.137 | 1.133 | |
| QH0692.42 | B | | | | | | |
| T255-34 | CRF02_AG | | | | | | |
| ZM135M.PL10a | C | | | | | | |
| AC10.0.29 | B | | | | | | |
| T257-31 | CRF02_AG | | | | | | |
| 6240_08_TA5_4622 | B (T/F) | | | | | | |
| CNE58 | BC | | | | | | |
| Ce0393_C3 | C (T/F) | | | | | | |
| R1166.c01 | CRF01_AE | | | | | | |
| CNE30 | BC | | | | | | |
| 235-47 | CRF02_AG | | | | | | |
| CNE17 | BC | | | | | | |
| BJOX009000.02.4 | CRF01_AE | | | | | | |
| 928-28 | CRF02_AG | | | | | | |
| X2131_C1_B5 | G | | | | | | |
| 9004SS_A3_4 | A (T/F) | | | | | | |
| BJOX025000.01.1 | CRF01_AE (T/F) | | | | | | |
| ZM53M.PB12 | C | | | | | | |
| ZM214M.PL15 | C | | | | | | |
| Ce703010054_2A2 | C (T/F) | | | | | | |
| CAAN5342.A2 | B | | | | | | |
| ZM197M.PB7 | C | | | | | | |
| Ce704809221_1B3 | C (T/F) | | | | | | |
| 703010201E5(Rev-) | C (T/F) | | | | | | |
| 6535.3 | B | | | | | | |
| SC05_6C11_2344 | B (T/F) | | | | | | |
| Q23.17 | A | | | | | | |
| C4118.c09 | CRF01_AE | | | | | | |
| PVO.4 | B | | | | | | |
| 1054_07_TC4_1499 | B (T/F) | | | | | | |
| 191955_A11 | A (T/F) | | | | 1.22 | 3.063 | |
| Ce2010_F5 | C (T/F) | | | | | | |
| ZM109F.PB4 | C | | | | | | |

IC$_{50}$ values (µg/ml): >50 | 10-50 | 1-10 | 0.1-1 | 0.01-0.1 | <0.01

FIG. 16

IC₈₀ Values (µg/ml)

| Virus ID | Virus ID | NIH45-46 | NIH45-46^G54W | 45-46m2 | 45-46m7 | 45-46m25 | 45-46m28 |
|---|---|---|---|---|---|---|---|
| Ce1172_H1 | C (T/F) | >50 | >50 | >50 | >50 | >50 | >50 |
| 620345.c01 | CRF01_AE | >50 | >50 | >50 | >50 | >50 | >50 |
| X2088_c9 | G | >50 | >50 | >50 | >50 | >50 | >50 |
| T278-50 | CRF02_AG | >50 | >50 | >50 | >50 | >50 | >50 |
| 89-F1_2_25 | CD | >50 | >50 | >50 | >50 | >50 | >50 |
| 6540.v4.c1 | AC | >50 | >50 | >50 | >50 | >50 | >50 |
| 6545.v4.c1 | AC | >50 | >50 | >50 | | | 4.532 |
| Du422.1 | C | >50 | >50 | >50 | | | 4.841 |
| 3817.v2.c59 | CD | >50 | >50 | >50 | >50 | >50 | >50 |
| CAP210.2.00.E8 | C | >50 | >50 | 9.052 | >50 | >50 | >50 |
| 211-9 | CRF02_AG | >50 | >50 | | >50 | >50 | >50 |
| CAP45.2.00.G3 | C | >50 | >50 | | 8.308 | | 1.274 |
| T250-4 | CRF02_AG | >50 | | | >50 | >50 | >50 |
| Du172.17 | C | >50 | | 0.125 | 7.854 | | 5.092 |
| 3016.v5.c45 | D | >50 | | | | | |
| 246F_C1G | C (T/F) | >50 | 2.446 | 0.14 | 0.275 | 0.225 | 0.203 |
| CNE20 | BC | >50 | 0.48 | | | | |
| BJOX028000.10.3 | CRF01_AE (T/F) | >50 | | | | | |
| X1632_S2_B10 | G | >50 | Not Tested | | | | |
| CNE21 | BC | | 0.16 | | | | |
| C2101.c01 | CRF01_AE | | 0.17 | 0.169 | 0.255 | 0.346 | 0.33 |
| ZM247v1(Rev-) | C (T/F) | | 2.6 | 0.827 | 0.897 | | 0.115 |
| HIV-16845-2.22 | C | | 2.1 | 1.44 | 1.074 | 1.582 | 1.211 |
| ZM233M.PB6 | C | | 0.11 | | 0.129 | 0.197 | 0.141 |
| C1080.c03 | CRF01_AE | | 0.94 | 0.599 | 1.166 | 1.233 | 1.541 |
| BJOX025000.01.1 | CRF01_AE (T/F) | 10 | 0.135 | 0.211 | 0.372 | 0.33 | 0.336 |
| 231966.c02 | D | 9.64 | 0.11 | | | | |
| THRO4156.18 | B | 8.22 | 1.81 | 2.736 | 3.263 | 3.271 | 4.789 |
| TRO.11 | B | 7.49 | 0.13 | | 0.156 | 0.153 | 0.13 |
| BJOX010000.06.2 | CRF01_AE (T/F) | 6.37 | 4.499 | 5.037 | 4.897 | 4.963 | 4.009 |
| 3103.v3.c10 | ACD | 6.15 | 0.56 | 0.594 | 1.125 | 1.305 | 0.907 |
| T251-18 | CRF02_AG | 3.66 | 0.92 | 1.426 | 1.526 | 1.616 | 1.1 |
| T255-34 | CRF02_AG | 3.442 | 0.168 | 0.274 | 0.282 | 0.249 | |
| Ce1176_A3 | C (T/F) | 3.17 | 0.45 | 0.467 | 1.338 | 1.429 | 1.13 |
| ZM135M.PL10a | C | 2.79 | 0.15 | 0.163 | 0.281 | 0.311 | 0.216 |
| CNE58 | BC | 2.08 | | | | | |
| AC10.0.29 | B | 1.93 | 0.63 | 0.554 | 0.632 | 0.773 | 0.469 |
| QH0692.42 | B | 1.71 | 1.12 | 0.822 | 1.586 | 1.834 | 1.286 |
| 6240.08.TA5.4622 | B (T/F) | 1.55 | 0.803 | 0.823 | 1.136 | 0.75 | 0.813 |
| 235-47 | CRF02_AG | 1.49 | | | | | |
| T257-31 | CRF02_AG | 1.38 | 0.46 | 0.471 | 0.884 | 0.899 | 0.579 |
| R1166.c01 | CRF01_AE | 1.21 | 0.91 | 1.01 | 1.044 | 1.086 | 0.982 |
| BJOX009000.02.4 | CRF01_AE | 1.16 | 0.564 | 0.621 | 0.949 | 0.909 | 0.911 |
| CNE30 | BC | 1.067 | | 0.31 | 0.41 | 0.492 | 0.419 |
| Ce0393_C3 | C (T/F) | 0.996 | | 0.151 | 0.183 | 0.184 | 0.153 |
| C4118.c09 | CRF01_AE | 0.91 | | | 0.154 | 0.129 | 0.136 |
| X2131_C1_B5 | G | 0.88 | 0.24 | 0.145 | 0.131 | 0.145 | |
| Ce704809221_1B3 | C (T/F) | 0.88 | 0.21 | 0.464 | 0.331 | 0.343 | 0.269 |
| CNE17 | BC | 0.734 | 0.127 | 0.254 | 0.327 | 0.333 | 0.238 |
| 9004SS_A3_4 | A (T/F) | 0.65 | 0.26 | 0.136 | 0.292 | 0.286 | 0.265 |
| 928-28 | CRF02_AG | 0.64 | 0.26 | 0.159 | 0.49 | 0.41 | 0.369 |
| 7030102001E5(Rev-) | C (T/F) | 0.63 | 0.228 | 0.229 | 0.301 | 0.389 | 0.249 |
| ZM53M.PB12 | C | 0.61 | 0.15 | 0.257 | 0.299 | 0.319 | 0.241 |
| MS208.A1 | A | 0.6 | 0.17 | | 0.186 | 0.181 | 0.127 |
| ZM214M.PL15 | C | 0.59 | 0.15 | 0.259 | 0.394 | 0.543 | 0.571 |
| ZM197M.P87 | C | 0.55 | 0.15 | 0.274 | 0.368 | 0.346 | 0.23 |
| 6535.3 | B | 0.54 | 0.13 | | 0.375 | 0.401 | 0.28 |
| Ce703010054_2A2 | C (T/F) | 0.508 | | 0.144 | 0.155 | 0.115 | |
| Q23.17 | A | 0.5 | | | | | |
| 191821_E6_1 | D (T/F) | 0.48 | | 0.12 | 0.221 | 0.218 | 0.232 |
| 1056_10_TA11_1826 | B (T/F) | 0.447 | 0.15 | 0.299 | 0.586 | 0.559 | 0.524 |
| ZM109F.PB4 | C | 0.47 | | | | | |
| 191955_A11 | A (T/F) | 0.43 | | | 9.265 | | 4.935 |
| PVO.4 | B | 0.41 | 0.15 | 0.2 | 0.156 | 0.17 | 0.138 |
| CNE5 | CRF01_AE | 0.41 | 0.116 | 0.137 | 0.233 | 0.398 | 0.204 |

| IC₈₀ values (µg/ml) | >50 | 10-50 | 1-10 | 0.1-1 | 0.01-0.1 | <0.01 |

|  | 45-46m2/93TH057 |
|---|---|
| Data collection | |
| Wavelength (Å) | 0.953 |
| Space group | $P2_12_12_1$ |
| Cell dimensions | |
| $a, b, c$ (Å) | 69.3, 70.5, 232.2 |
| $\alpha, \beta, \gamma$ (°) | 90.0, 90.0, 90.0 |
| Resolution (Å) | 34.85-2.82 (2.89-2.82) |
| $R_{meas}$ (%) | 9.9 (96.8) |
| $R_{mrgd\text{-}F}$ (%) | 14.4 (99.0) |
| $CC_{1/2}$ † | 99.7 (73.6) |
| $I/\sigma I$ | 11.0 (2.1) |
| Completeness (%) | 98.4 (99.3) |
| Multiplicity | 3.8 |
| Reflections | 106875 |
| Unique reflections | 27846 |
| Refinement | |
| Resolution (Å) | 34.85-2.82 |
| No. reflections | 27841 |
| $R_{work} / R_{free}$ | 19.3 / 23.1 |
| No. atoms | |
| Protein | 5998 |
| Carbohydrates | 242 |
| Water | 23 |
| *B*-factors | |
| Protein | 76.3 |
| Carbohydrates | 115 |
| Water | 51 |
| Ramachandran | |
| Favored (%) | 95.63 |
| Allowed (%) | 4.1 |
| Outlier (%) | 0.26 |
| r.m.s. deviations | |
| Bond lengths (Å) | 0.007 |
| Bond angles (°) | 1.027 |

FIG. 18

| Virus | Clade | 45-46m2 | | 45-46m2 45-46m7 | | 45-46m2 45-46m7 PG9 | | 45-46m2 45-46m7 10-1074 | |
|---|---|---|---|---|---|---|---|---|---|
| | | IC$_{50}$ | IC$_{80}$ | IC$_{50}$ | IC$_{80}$ | IC$_{50}$ | IC$_{80}$ | IC$_{50}$ | IC$_{80}$ |
| T278-50 | CRF02_AG | >50 | >50 | >50 | >50 | 9.359 | >50 | 4.598 | 49.446 |
| 89-F1_2_25 | CD | >50 | >50 | >50 | >50 | 1.881 | >50 | >50 | >50 |
| 6540.v4.c1 | AC | >50 | >50 | >50 | >50 | 0.204 | 1.004 | >50 | >50 |
| Ce1172_H1 | C (T/F) | >50 | >50 | >50 | >50 | 0.148 | 0.548 | >50 | >50 |
| 620345.c01 | CRF01_AE | >50 | >50 | >50 | >50 | >50 | >50 | >50 | >50 |
| X2088_c9 | G | >50 | >50 | >50 | >50 | <0.002 | >50 | <0.001 | 0.006 |
| 6545.v4.c1 | AC | 9.214 | >50 | 7.283 | >50 | 0.106 | 0.424 | 1.358 | 17.500 |
| Du422.1 | C | 3.837 | 28.001 | 16.614 | 14.226 | 0.144 | 0.677 | 18.500 | 47.900 |
| CAP210.2.00.E8 | C | 1.866 | 8.872 | 2.729 | >50 | 0.212 | 0.735 | 1.601 | 7.407 |
| T250-4 | CRF02_AG | 1.512 | 22.805 | 5.608 | 1.650 | 0.006 | 0.005 | <0.001 | 0.002 |
| THRO4156.18 | B | 0.762 | 2.016 | 0.446 | 1.599 | 0.384 | 1.245 | 0.346 | 1.525 |
| 3817.v2.c59 | CD | 0.759 | 4.004 | 0.249 | 18.696 | 0.007 | 0.005 | 0.174 | 0.659 |
| BJOX010000.06.2 | CRF01_AE (T/F) | 0.690 | 2.574 | 0.302 | 2.539 | 0.135 | 1.176 | 0.352 | 1.304 |
| R1166.c01 | CRF01_AE | 0.588 | 2.314 | 0.241 | 0.773 | 0.105 | 0.268 | 0.006 | 0.279 |
| T251-18 | CRF02_AG | 0.384 | 1.346 | 0.249 | 0.738 | 0.205 | 0.570 | 0.006 | 0.263 |
| 211-9 | CRF02_AG | 0.351 | 2.239 | 0.438 | 2.894 | 0.166 | 0.489 | 0.157 | 0.157 |
| HIV-16845-2.22 | C | 0.335 | 1.568 | 0.261 | 1.200 | 0.160 | 0.570 | 0.352 | 0.344 |
| 3103.v3.c10 | ACD | 0.306 | 0.767 | 0.170 | 0.445 | 0.114 | 0.303 | 0.006 | 0.006 |
| 6240_08_TA5_4622 | B (T/F) | 0.282 | 0.814 | 0.113 | 0.374 | | 0.232 | | |
| BJOX009000.02.4 | CRF01_AE | 0.256 | 0.872 | 0.123 | 0.581 | 0.126 | 0.452 | 0.115 | 0.314 |
| C1080.c03 | CRF01_AE | 0.245 | 0.854 | 0.109 | 0.523 | 0.005 | | | 0.425 |

| Virus | Clade | 45-46m2 | | 45-46m2 45-46m7 | | 45-46m2 45-46m7 PG9 | | 45-46m2 45-46m7 10-1074 | |
|---|---|---|---|---|---|---|---|---|---|
| | | $IC_{50}$ | $IC_{80}$ | $IC_{50}$ | $IC_{80}$ | $IC_{50}$ | $IC_{80}$ | $IC_{50}$ | $IC_{80}$ |
| 6480.v4.c25 | CD | | | | | | | | |
| PVO.4 | B | | | | | | | | |
| C3347.c11 | CRF01_AE | | | | | | | | |
| P0402_c2_11 | G | | | | | | | | |
| RHPA4259.7 | B | | | | | | | | |
| REJO4541.67 | B | | | | | | | | |
| TRJO4551.58 | B | | | | | | | | |
| CNE20 | BC | | | | | | | | |
| CNE58 | BC | | | | | | | | |
| R2184.c04 | CRF01_AE | | | | | | | | |
| Du156.12 | C | | | | | | | | |
| 1006_11_C3_1601 | B (T/F) | | | | | | | | |
| 1012_11_TC21_3257 | B (T/F) | | | | | | | | |
| 2M249M.PL1 | C | | | | | | | | |
| X1254_c3 | G | | | | | | | | |
| HIV 16055-2.3 | C | | | | | | | | |
| 191084 87-19 | A (T/F) | | | | | | | | |
| 0815.v3.c3 | ACD | | | | | | | | |
| 3415.v1.c1 | A | | | | | | | | |
| 191955_A11 | A (T/F) | | | | | | | | |
| 3301.v1.C24 | AC | | | | | | | | |

FIG. 18 (Cont.)

| Virus | Clade | 45-46m2 | | 45-46m2 45-46m7 | | 45-46m2 45-46m7 PG9 | | 45-46m2 45-46m7 10-1074 | |
|---|---|---|---|---|---|---|---|---|---|
| | | IC50 | IC80 | IC50 | IC80 | IC50 | IC80 | IC50 | IC80 |
| Ce1086_B2 | C (T/F) | 0.001 | 0.001 | 0.001 | 0.001 | <0.001 | 0.001 | <0.001 | 0.001 |
| 3365.v2.c2 | A | 0.001 | 0.001 | <0.001 | 0.001 | <0.001 | 0.001 | <0.001 | 0.001 |
| 6041.v3.c23 | AC | 0.001 | 0.001 | <0.001 | 0.001 | <0.001 | 0.001 | <0.001 | 0.001 |
| Q769.d22 | A | 0.001 | 0.001 | <0.001 | 0.001 | <0.001 | 0.001 | <0.001 | 0.001 |
| BJOX028000.10.3 | CRF01_AE (T/F) | 0.001 | 0.007 | <0.001 | 0.007 | <0.001 | 0.001 | <0.001 | 0.001 |
| X1632_S2_B10 | G | 0.001 | 0.005 | <0.001 | 0.004 | <0.001 | 0.001 | <0.001 | 0.001 |
| WEAU_d15_410_787 | B (T/F) | <0.001 | 0.001 | <0.001 | 0.001 | <0.001 | 0.001 | <0.001 | 0.001 |
| HIV-001428-2.42 | C | <0.001 | 0.001 | <0.001 | 0.001 | <0.001 | 0.001 | <0.001 | 0.001 |
| BF1266.431a | C (T/F) | <0.001 | 0.001 | <0.001 | 0.001 | 0.001 | 0.007 | <0.001 | 0.001 |
| CNE19 | BC | <0.001 | 0.005 | <0.001 | 0.005 | <0.001 | 0.005 | <0.001 | 0.004 |
| CNE52 | BC | <0.001 | 0.001 | <0.001 | 0.001 | <0.001 | 0.001 | <0.001 | 0.001 |
| CNE53 | BC | <0.001 | 0.001 | <0.001 | 0.001 | <0.001 | 0.001 | <0.001 | 0.001 |
| Q259.d2.17 | A | <0.001 | 0.001 | <0.001 | 0.001 | <0.001 | 0.001 | <0.001 | 0.001 |
| Q842.d12 | A | <0.001 | 0.001 | <0.001 | 0.001 | <0.001 | 0.001 | <0.001 | 0.001 |
| 263-8 | CRF02_AG | <0.001 | 0.002 | <0.001 | 0.002 | <0.001 | 0.002 | <0.001 | 0.002 |
| 235-47 | CRF02_AG | <0.001 | 0.005 | <0.001 | 0.005 | <0.001 | 0.005 | <0.001 | 0.005 |

| IC50 and IC80 values (µg/ml) | >50 | 10-50 | 1-10 | 0.1-1 | 0.01-0.1 | <0.01 |
|---|---|---|---|---|---|---|

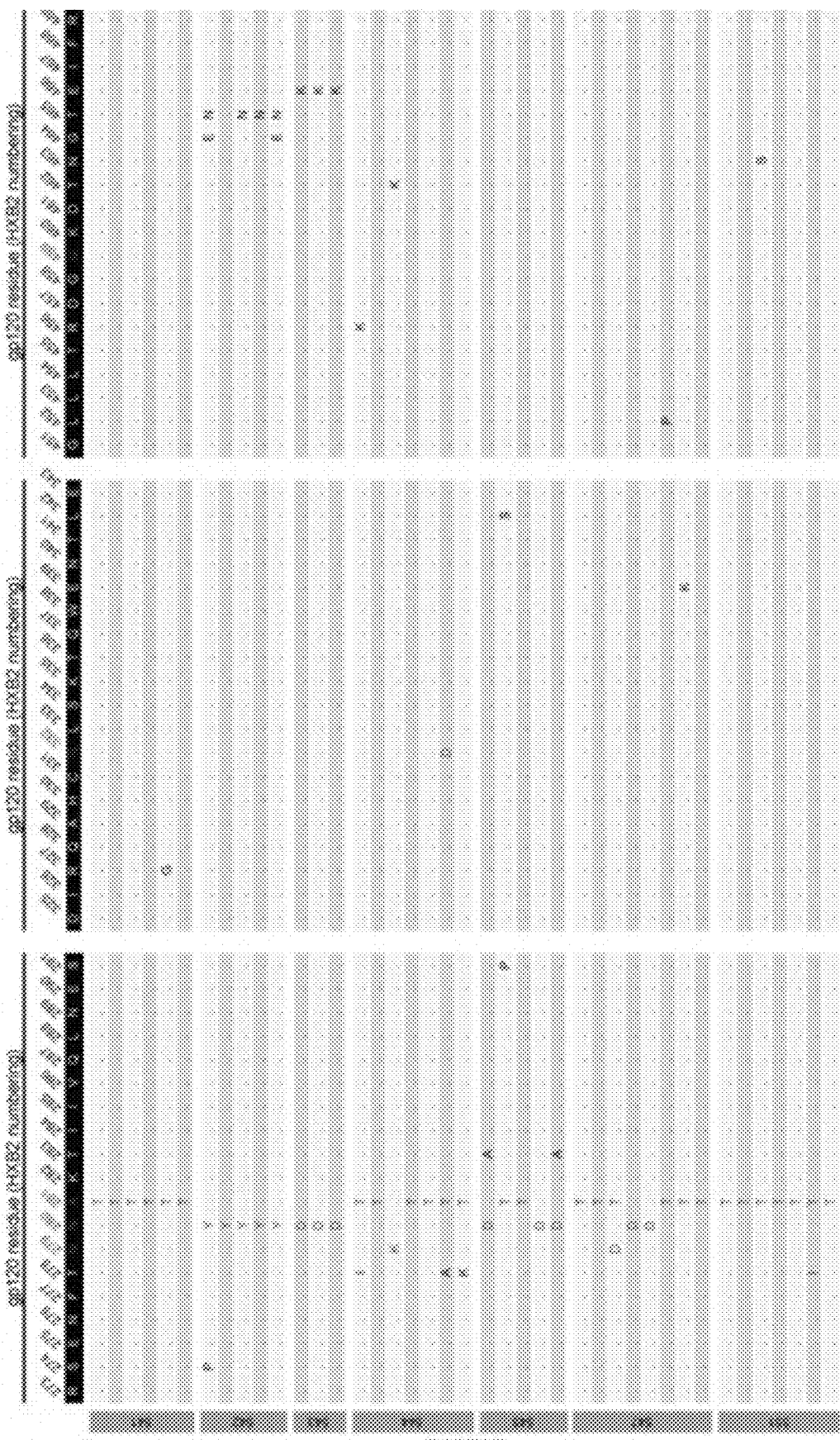

FIG. 20A

Sequence alignment of heavy chain variable regions showing antibody sequences including VH1-2*02, 3BNC13, 3BNC16, 3BNC18, 3BNC72, 3BNC66, 3BNC142, 3BNC53, 3BNC42, 3BNC102, 3ANC3, 3BNC108, 3BNC55, 3BNC89, VRC03*, 3BNC91, 3BNC104, 3BNC62, 3BNC95, 3BNC176, 3BNC117, 3BNC60, 12A12, VRC-PG04, VRC-H15, VRC-H12, VRC-H5, NIH45-46, VRC01, VRC-CH31, VRC-CH30, VRC-CH32, VRC-CH33, VRC-CH34, aligned against IGHJ2*01, with position markers at 50, 58, 71, and 100B.

FIG. 20B

SEQUENCE LISTING

<160> NUMBER OF SEQ ID NOS: 85

<210> SEQ ID NO 1
<211> LENGTH: 104
<212> TYPE: PRT
<213> ORGANISM: Homo sapiens

<400> SEQUENCE: 1

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 2
<211> LENGTH: 49
<212> TYPE: PRT
<213> ORGANISM: Homo sapiens

<400> SEQUENCE: 2

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly

<210> SEQ ID NO 3
<211> LENGTH: 104
<212> TYPE: PRT
<213> ORGANISM: Homo sapiens

<400> SEQUENCE: 3

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Arg Asn Leu Glu Ser Gly Asp
65                  70                  75                  80

Phe Gly Leu Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 4
<211> LENGTH: 121
<212> TYPE: PRT
<213> ORGANISM: Homo sapiens

<400> SEQUENCE: 4

-continued

Gln Val Gln Leu Val Gln Ser Gly Gly Gln Met Lys Lys Pro Gly Glu
1               5                   10                  15

Ser Met Arg Ile Ser Cys Gln Ala Ser Gly Tyr Glu Phe Ile Asp Cys
            20                  25                  30

Thr Leu Asn Trp Val Arg Leu Ala Pro Gly Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ala Asp Asp Thr Ala Val Tyr Tyr Cys
                85                  90                  95

Thr Arg Gly Lys Asn Cys Asp Tyr Asn Trp Asp Phe Glu His Trp Gly
            100                 105                 110

Arg Gly Thr Pro Val Thr Val Ser Ser
        115                 120

<210> SEQ ID NO 5
<211> LENGTH: 107
<212> TYPE: PRT
<213> ORGANISM: Homo sapiens

<400> SEQUENCE: 5

Glu Ile Val Leu Thr Gln Ser Pro Ala Thr Leu Ser Leu Ser Pro Gly
1               5                   10                  15

Glu Thr Ala Ile Ile Ser Cys Arg Thr Ser Gln Ser Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Ala Asp Tyr Asn Leu Ser Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg Thr Val Ala
            100                 105

<210> SEQ ID NO 6
<211> LENGTH: 125
<212> TYPE: PRT
<213> ORGANISM: Homo sapiens

<400> SEQUENCE: 6

Gln Val Arg Leu Ser Gln Ser Gly Gly Gln Met Lys Lys Pro Gly Glu
1               5                   10                  15

Ser Met Arg Leu Ser Cys Arg Ala Ser Gly Tyr Glu Phe Leu Asn Cys
            20                  25                  30

Pro Ile Asn Trp Ile Arg Leu Ala Pro Gly Arg Pro Glu Trp Met
        35                  40                  45

Gly Trp Leu Lys Pro Arg Gly Gly Ala Val Asn Tyr Ala Arg Lys Phe
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ser Asp Asp Thr Ala Val Tyr Phe Cys
                85                  90                  95

```
Thr Arg Gly Lys Tyr Cys Thr Ala Arg Asp Tyr Tyr Asn Trp Asp Phe
            100                 105                 110

Glu His Trp Gly Arg Gly Ala Pro Val Thr Val Ser Ser
            115                 120             125

<210> SEQ ID NO 7
<211> LENGTH: 103
<212> TYPE: PRT
<213> ORGANISM: Homo sapiens

<400> SEQUENCE: 7

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
                20                  25                  30

Gln Gln Arg Arg Gly Lys Ala Pro Lys Leu Leu Ile Tyr Asp Gly Ser
            35                  40                  45

Lys Leu Glu Arg Gly Val Pro Ala Arg Phe Ser Gly Arg Arg Trp Gly
        50                  55                  60

Gln Glu Tyr Asn Leu Thr Ile Asn Asn Leu Gln Pro Glu Asp Val Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala
            100

<210> SEQ ID NO 8
<211> LENGTH: 123
<212> TYPE: PRT
<213> ORGANISM: Homo sapiens

<400> SEQUENCE: 8

Gln Val His Leu Ser Gln Ser Gly Ala Ala Val Thr Lys Pro Gly Ala
1               5                   10                  15

Ser Val Arg Val Ser Cys Glu Ala Ser Gly Tyr Lys Ile Ser Asp His
                20                  25                  30

Phe Ile His Trp Trp Arg Gln Ala Pro Gly Gln Gly Leu Gln Trp Val
            35                  40                  45

Gly Trp Ile Asn Pro Lys Thr Gly Gln Pro Asn Asn Pro Arg Gln Phe
        50                  55                  60

Gln Gly Arg Val Ser Leu Thr Arg Gln Ala Ser Trp Asp Phe Asp Thr
65                  70                  75                  80

Tyr Ser Phe Tyr Met Asp Leu Lys Ala Val Arg Ser Asp Asp Thr Ala
                85                  90                  95

Ile Tyr Phe Cys Ala Arg Gln Arg Ser Asp Phe Trp Asp Phe Asp Val
            100                 105                 110

Trp Gly Ser Gly Thr Gln Val Thr Val Ser Ser
            115                 120

<210> SEQ ID NO 9
<211> LENGTH: 103
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15
```

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Arg Trp Gly
50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Val Val Pro Gly Thr Arg Leu
                85                  90                  95

Asp Leu Lys Arg Thr Val Ala
            100

<210> SEQ ID NO 10
<211> LENGTH: 123
<212> TYPE: PRT
<213> ORGANISM: Homo sapiens

<400> SEQUENCE: 10

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Leu Arg Ser Asp Asp Thr Ala
                85                  90                  95

Val Tyr Phe Cys Ala Arg Gln Arg Ser Asp Tyr Trp Asp Phe Asp Val
                100                 105                 110

Trp Gly Ser Gly Thr Gln Val Thr Val Ser Ser
            115                 120

<210> SEQ ID NO 11
<211> LENGTH: 103
<212> TYPE: PRT
<213> ORGANISM: Homo sapiens

<400> SEQUENCE: 11

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Thr Gly Val Pro Ser Arg Phe Thr Gly Arg Arg Trp Gly
50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala
            100

<210> SEQ ID NO 12
<211> LENGTH: 123
<212> TYPE: PRT
<213> ORGANISM: Homo sapiens

<400> SEQUENCE: 12

Gln Val Arg Leu Leu Gln Ser Gly Ala Ala Val Thr Lys Pro Gly Ala
1               5                   10                  15

Ser Val Arg Val Ser Cys Glu Ala Ser Gly Tyr Glu Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
    50                  55                  60

Gln Gly Arg Val Ser Leu Thr Arg Gln Ala Ser Trp Asp Phe Asp Ser
65                  70                  75                  80

Tyr Ser Phe Tyr Met Asp Leu Lys Ala Leu Arg Ser Asp Asp Thr Gly
                85                  90                  95

Val Tyr Phe Cys Ala Arg Gln Arg Ser Asp Tyr Trp Asp Phe Asp Val
            100                 105                 110

Trp Gly Ser Gly Thr Gln Val Thr Val Ser Ser
        115                 120

<210> SEQ ID NO 13
<211> LENGTH: 103
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Arg Trp Gly
    50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala
            100

<210> SEQ ID NO 14
<211> LENGTH: 123
<212> TYPE: PRT
<213> ORGANISM: Homo sapiens

<400> SEQUENCE: 14

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Leu Phe

```
                     50                  55                  60
Gln Gly Arg Val Ser Leu Thr Arg His Ala Ser Trp Asp Phe Asp Thr
 65                  70                  75                  80

Phe Ser Phe Tyr Met Asp Leu Lys Ala Val Arg Ser Asp Asp Thr Ala
                     85                  90                  95

Val Tyr Phe Cys Ala Arg Gln Arg Ser Asp Tyr Trp Asp Phe Asp Val
                100                 105                 110

Trp Gly Ser Gly Thr Gln Val Thr Val Ser Ser
            115                 120
```

<210> SEQ ID NO 15
<211> LENGTH: 103
<212> TYPE: PRT
<213> ORGANISM: Homo sapiens

<400> SEQUENCE: 15

```
Asp Ile Gln Met Thr Gln Ser Pro Ser Ser Leu Ser Ala Ser Val Gly
 1                   5                  10                  15

Asp Thr Val Thr Ile Thr Cys Gln Ala Asn Gly Tyr Leu Asn Trp Tyr
                     20                  25                  30

Gln Gln Arg Arg Gly Lys Ala Pro Lys Leu Leu Ile Tyr Asp Gly Ser
                 35                  40                  45

Lys Leu Glu Arg Gly Val Pro Ser Arg Phe Ser Gly Arg Arg Trp Gly
 50                  55                  60

Gln Glu Tyr Asn Leu Thr Ile Asn Asn Leu Gln Ala Glu Asp Ile Ala
 65                  70                  75                  80

Thr Tyr Phe Cys Gln Val Tyr Glu Phe Ala Val Pro Gly Thr Arg Leu
                     85                  90                  95

Asp Leu Lys Arg Thr Val Ala
            100
```

<210> SEQ ID NO 16
<211> LENGTH: 123
<212> TYPE: PRT
<213> ORGANISM: Homo sapiens

<400> SEQUENCE: 16

```
Gln Val Gln Leu Leu Gln Ser Gly Ala Ala Val Thr Lys Pro Gly Ala
 1                   5                  10                  15

Ser Val Arg Val Ser Cys Glu Ala Ser Gly Tyr Asn Ile Arg Asp Tyr
                     20                  25                  30

Phe Ile His Trp Trp Arg Gln Ala Pro Gly Gln Gly Leu Gln Trp Val
                 35                  40                  45

Gly Trp Ile Asn Pro Lys Thr Gly Gln Pro Asn Asn Pro Arg Gln Phe
 50                  55                  60

Gln Gly Arg Val Ser Leu Thr Arg His Ala Ser Trp Asp Phe Asp Thr
 65                  70                  75                  80

Phe Ser Phe Tyr Met Asp Leu Lys Gly Leu Arg Ser Asp Asp Thr Ala
                     85                  90                  95

Ile Tyr Phe Cys Ala Arg Gln Arg Ser Asp Tyr Trp Asp Phe Asp Val
                100                 105                 110

Trp Gly Ser Gly Thr Gln Val Thr Val Ser Ser
            115                 120
```

<210> SEQ ID NO 17
<211> LENGTH: 107
<212> TYPE: PRT

<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gln Ala Gly Gln Gly Ile Gly Ser Ser
            20                  25                  30

Leu Gln Trp Tyr Gln Gln Lys Pro Gly Lys Ala Pro Lys Leu Leu Val
        35                  40                  45

His Gly Ala Ser Asn Leu His Arg Gly Val Pro Ser Arg Phe Ser Gly
    50                  55                  60

Ser Gly Phe His Thr Thr Phe Ser Leu Thr Ile Ser Gly Leu Gln Arg
65                  70                  75                  80

Asp Asp Phe Ala Thr Tyr Phe Cys Ala Val Leu Glu Phe Phe Gly Pro
                85                  90                  95

Gly Thr Lys Val Glu Ile Lys Arg Thr Val Ala
            100                 105

<210> SEQ ID NO 18
<211> LENGTH: 122
<212> TYPE: PRT
<213> ORGANISM: Homo sapiens

<400> SEQUENCE: 18

Ser Gln His Leu Val Gln Ser Gly Thr Gln Val Lys Lys Pro Gly Ala
1               5                   10                  15

Ser Val Arg Ile Ser Cys Gln Ala Ser Gly Tyr Ser Phe Thr Asp Tyr
            20                  25                  30

Val Leu His Trp Trp Arg Gln Ala Pro Gly Gln Gly Leu Glu Trp Met
        35                  40                  45

Gly Trp Ile Lys Pro Val Tyr Gly Ala Arg Asn Tyr Ala Arg Arg Phe
    50                  55                  60

Gln Gly Arg Ile Asn Phe Asp Arg Asp Ile Tyr Arg Glu Ile Ala Phe
65                  70                  75                  80

Met Asp Leu Ser Gly Leu Arg Ser Asp Asp Thr Ala Leu Tyr Phe Cys
                85                  90                  95

Ala Arg Asp Gly Ser Gly Asp Asp Thr Ser Trp His Leu Asp Pro Trp
            100                 105                 110

Gly Gln Gly Thr Leu Val Ile Val Ser Ala
        115                 120

<210> SEQ ID NO 19
<211> LENGTH: 102
<212> TYPE: PRT
<213> ORGANISM: Homo sapiens

<400> SEQUENCE: 19

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
        35                  40                  45

Thr Ser Lys Arg Ala Ser Gly Ile Pro Asp Arg Phe Ser Gly Ser Gln
    50                  55                  60

Phe Gly Lys Gln Tyr Thr Leu Thr Ile Thr Arg Met Glu Pro Glu Asp
65                  70                  75                  80

```
Phe Ala Arg Tyr Tyr Cys Gln Gln Leu Glu Phe Phe Gly Gln Gly Thr
                85                  90                  95

Arg Leu Glu Ile Arg Arg
            100
```

<210> SEQ ID NO 20
<211> LENGTH: 125
<212> TYPE: PRT
<213> ORGANISM: Homo sapiens

<400> SEQUENCE: 20

```
Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
                20                  25                  30

Glu Leu Ile His Trp Val Arg Gln Ala Pro Gly Gln Gly Leu Glu Trp
            35                  40                  45

Ile Gly Trp Val Lys Thr Val Thr Gly Ala Val Asn Phe Gly Ser Pro
        50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Tyr Thr Gly Gly Gln Gly Trp Tyr Phe
                100                 105                 110

Asp Leu Trp Gly Arg Gly Thr Leu Ile Val Val Ser Ser
            115                 120                 125
```

<210> SEQ ID NO 21
<211> LENGTH: 103
<212> TYPE: PRT
<213> ORGANISM: Homo sapiens

<400> SEQUENCE: 21

```
Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
                20                  25                  30

Leu Asn Trp Tyr Gln Gln Lys Pro Gly Lys Ala Pro Lys Leu Leu Val
            35                  40                  45

Ser Asp Ala Ser Ile Leu Glu Gly Gly Val Pro Ser Arg Phe Ser Gly
        50                  55                  60

Ser Gly Phe His Gln Asn Phe Ser Leu Thr Ile Ser Ser Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100
```

<210> SEQ ID NO 22
<211> LENGTH: 131
<212> TYPE: PRT
<213> ORGANISM: Homo sapiens

<400> SEQUENCE: 22

```
Gln Val Gln Leu Val Gln Ser Gly Ala Ala Val Arg Lys Pro Gly Ala
1               5                   10                  15
```

```
Ser Val Thr Val Ser Cys Lys Phe Ala Glu Asp Asp Tyr Ser Pro
            20                  25                  30

His Trp Val Asn Pro Ala Pro Glu His Tyr Ile His Phe Leu Arg Gln
            35                  40                  45

Ala Pro Gly Gln Gln Leu Glu Trp Leu Ala Trp Met Asn Pro Thr Asn
 50                      55                      60

Gly Ala Val Asn Tyr Ala Trp Gln Leu His Gly Arg Leu Thr Ala Thr
 65                  70                  75                  80

Arg Asp Gly Ser Met Thr Thr Ala Phe Leu Glu Val Arg Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Leu
            115                 120                 125

Val Ser Ser
    130
```

```
<210> SEQ ID NO 23
<211> LENGTH: 103
<212> TYPE: PRT
<213> ORGANISM: Homo sapiens

<400> SEQUENCE: 23
```

```
Asp Ile Gln Met Thr Gln Ser Pro Ser Ser Leu Ser Ala Ser Leu Gly
 1                   5                  10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
            35                  40                  45

Ser Asp Ala Ser Thr Leu Glu Gly Gly Val Pro Ser Arg Phe Ser Gly
 50                      55                      60

Ser Gly Phe His Gln Asn Phe Ser Leu Thr Ile Ser Ser Leu Gln Ala
 65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100
```

```
<210> SEQ ID NO 24
<211> LENGTH: 131
<212> TYPE: PRT
<213> ORGANISM: Homo sapiens

<400> SEQUENCE: 24
```

```
Gln Val Gln Leu Val Gln Ser Gly Ala Ala Val Arg Lys Pro Gly Ala
 1                   5                  10                  15

Ser Val Thr Val Ser Cys Lys Phe Ala Glu Asp Asp Tyr Ser Pro
            20                  25                  30

Tyr Trp Val Asn Pro Ala Pro Glu His Phe Ile His Phe Leu Arg Gln
            35                  40                  45

Ala Pro Gly Gln Gln Leu Glu Trp Leu Ala Trp Met Asn Pro Thr Asn
 50                      55                      60

Gly Ala Val Asn Tyr Ala Trp Tyr Leu Asn Gly Arg Val Thr Ala Thr
 65                  70                  75                  80

Arg Asp Arg Ser Met Thr Thr Ala Phe Leu Glu Val Lys Ser Leu Arg
                85                  90                  95
```

-continued

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 25
<211> LENGTH: 103
<212> TYPE: PRT
<213> ORGANISM: Homo sapiens

<400> SEQUENCE: 25

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Pro Gly Arg Ala Pro Lys Leu Leu Val
        35                  40                  45

Ser Asp Ala Ser Ile Leu Glu Gly Gly Val Pro Thr Arg Phe Ser Gly
    50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 26
<211> LENGTH: 131
<212> TYPE: PRT
<213> ORGANISM: Homo sapiens

<400> SEQUENCE: 26

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Phe Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Lys Pro Thr Asn
    50                  55                  60

Gly Ala Val Asn Tyr Ala Trp Gln Leu Gln Gly Arg Val Thr Val Thr
65                  70                  75                  80

Arg Asp Arg Ser Gln Thr Thr Ala Phe Leu Glu Val Lys Asn Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Ile Ser Ala
    130

<210> SEQ ID NO 27
<211> LENGTH: 103
<212> TYPE: PRT
<213> ORGANISM: Homo sapiens -continued

<400> SEQUENCE: 27

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Arg Gly Arg Ala Pro Arg Leu Leu Val
        35                  40                  45

Ser Asp Ala Ser Val Leu Glu Gly Gly Val Pro Ser Arg Phe Ser Gly
    50                  55                  60

Ser Gly Phe His Gln Asn Phe Ser Leu Thr Ile Ser Thr Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 28
<211> LENGTH: 131
<212> TYPE: PRT
<213> ORGANISM: Homo sapiens

<400> SEQUENCE: 28

Gln Val Gln Leu Val Gln Ser Gly Ala Ala Val Arg Lys Pro Gly Ala
1               5                   10                  15

Ser Ile Ser Val Ser Cys Lys Phe Ala Asp Ala Asp Asp Tyr Ser Pro
            20                  25                  30

His Trp Met Asn Pro Ala Pro Glu His Tyr Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Tyr Leu Asn Gly Arg Val Thr Ala Thr
65                  70                  75                  80

Arg Asp Arg Ser Met Thr Thr Ala Phe Leu Glu Val Arg Ser Leu Arg
                85                  90                  95

Ser Asp Asp Thr Ala Val Tyr Tyr Cys Ala Arg Ala Gln Lys Arg Ala
            100                 105                 110

Arg Ser Glu Trp Ala Tyr Ala His Trp Gly Gln Gly Thr Pro Val Val
        115                 120                 125

Val Ser Ser
        130

<210> SEQ ID NO 29
<211> LENGTH: 103
<212> TYPE: PRT
<213> ORGANISM: Homo sapiens

<400> SEQUENCE: 29

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
        35                  40                  45

Ser Asp Ala Ser Ile Leu Glu Gly Gly Val Pro Ser Arg Phe Ser Gly
    50                  55                  60

Ser Gly Phe His Gln Asn Phe Ser Leu Thr Ile Ser Ser Leu Gln Pro

```
              65                  70                  75                  80
Glu Asp Val Ala Thr Tyr Phe Cys Gln Gln Tyr Glu Thr Phe Gly Gln
                    85                  90                  95

Gly Thr Lys Val Asp Ile Lys
            100

<210> SEQ ID NO 30
<211> LENGTH: 131
<212> TYPE: PRT
<213> ORGANISM: Homo sapiens

<400> SEQUENCE: 30

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Asp Trp Ser Pro
                20                  25                  30

His Trp Val Asn Pro Ala Pro Glu His Tyr Ile His Phe Leu Arg Gln
                35                  40                  45

Ala Pro Gly Gln Gln Leu Glu Trp Leu Ala Trp Met Asn Pro Thr Asn
            50                  55                  60

Gly Ala Val Asn Tyr Ala Trp Gln Leu Asn Gly Arg Leu Thr Ala Thr
65                  70                  75                  80

Arg Asp Thr Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
                100                 105                 110

Arg Ser Glu Trp Ala Tyr Ala His Trp Gly Gln Gly Thr Pro Val Val
            115                 120                 125

Val Ser Ser
        130

<210> SEQ ID NO 31
<211> LENGTH: 103
<212> TYPE: PRT
<213> ORGANISM: Homo sapiens

<400> SEQUENCE: 31

Glu Ile Val Leu Thr Gln Ser Pro Gly Ile Leu Ser Leu Ser Pro Gly
1               5                   10                  15

Glu Thr Ala Thr Leu Phe Cys Lys Ala Ser Gln Gly Gly Asn Ala Met
                20                  25                  30

Thr Trp Tyr Gln Lys Arg Gly Gln Val Pro Arg Leu Leu Ile Tyr
                35                  40                  45

Asp Thr Ser Arg Arg Ala Ser Gly Val Pro Asp Arg Phe Val Gly Ser
            50                  55                  60

Gly Ser Gly Thr Asp Phe Phe Leu Thr Ile Asn Lys Leu Asp Arg Glu
65                  70                  75                  80

Asp Phe Ala Val Tyr Tyr Cys Gln Gln Phe Glu Phe Phe Gly Leu Gly
                85                  90                  95

Ser Glu Leu Glu Val His Arg
            100

<210> SEQ ID NO 32
<211> LENGTH: 130
<212> TYPE: PRT
<213> ORGANISM: Homo sapiens

<400> SEQUENCE: 32
```

```
Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
            20                  25                  30

Ser Ile His Trp Val Arg Leu Ile Pro Asp Lys Gly Phe Glu Trp Ile
        35                  40                  45

Gly Trp Ile Lys Pro Leu Trp Gly Ala Val Ser Tyr Ala Arg Gln Leu
    50                  55                  60

Gln Gly Arg Val Ser Met Thr Arg Gln Leu Ser Gln Asp Pro Asp Asp
65                  70                  75                  80

Pro Asp Trp Gly Val Ala Tyr Met Glu Phe Ser Gly Leu Thr Pro Ala
                85                  90                  95

Asp Thr Ala Glu Tyr Phe Cys Val Arg Arg Gly Ser Cys Asp Tyr Cys
            100                 105                 110

Gly Asp Phe Pro Trp Gln Tyr Trp Gly Gln Gly Thr Val Val Val Val
            115                 120                 125

Ser Ser
130

<210> SEQ ID NO 33
<211> LENGTH: 104
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Lys Val Thr Ile Thr Cys Gln Thr Ser Ala Gly Tyr Leu Asn Trp
            20                  25                  30

Tyr Gln Gln Arg Arg Gly Arg Ala Pro Lys Leu Leu Met Tyr Asp Gly
        35                  40                  45

Ser Arg Leu Val Thr Gly Val Pro Ser Arg Phe Ser Gly Arg Arg Trp
    50                  55                  60

Gly Thr Gln Tyr Asn Leu Thr Ile Gly Ser Leu Gln Pro Glu Asp Ile
65                  70                  75                  80

Ala Thr Tyr Tyr Cys Gln Val Tyr Glu Phe Phe Gly Pro Gly Thr Arg
                85                  90                  95

Leu Asp Leu Lys Ser Thr Val Ala
            100

<210> SEQ ID NO 34
<211> LENGTH: 119
<212> TYPE: PRT
<213> ORGANISM: Homo sapiens

<400> SEQUENCE: 34

Gln Val Gln Leu Val Gln Ser Gly Thr Ala Val Lys Arg Pro Gly Ala
1               5                   10                  15

Ser Val Arg Val Ser Cys Gln Ala Ser Gly Tyr Thr Phe Thr Asp Tyr
            20                  25                  30

Phe Ile Tyr Trp Trp Arg Gln Ala Pro Gly Gln Gly Leu Glu Trp Leu
        35                  40                  45

Gly Trp Ile Asn Pro Leu Thr Ser Gln Pro Ser Tyr Pro Ser Arg Phe
    50                  55                  60

Gln Gly Arg Leu Thr Leu Thr Arg Asp Thr Phe Asp Glu Met Leu Tyr
65                  70                  75                  80
```

```
Met Asp Leu Arg Gly Leu Arg Ser Asp Asp Thr Gly Ile Tyr Phe Cys
                85                  90                  95

Ala Arg Arg His Ser Asp Tyr Cys Asp Phe Asp Ile Trp Gly Ser Gly
            100                 105                 110

Thr Gln Ile Ile Val Ser Ser
        115
```

<210> SEQ ID NO 35
<211> LENGTH: 103
<212> TYPE: PRT
<213> ORGANISM: Homo sapiens

<400> SEQUENCE: 35

```
Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Arg Trp Gly
    50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Ala Val Pro Gly Thr Arg Leu
                85                  90                  95

Asp Leu Lys Arg Thr Val Ala
            100
```

<210> SEQ ID NO 36
<211> LENGTH: 123
<212> TYPE: PRT
<213> ORGANISM: Homo sapiens

<400> SEQUENCE: 36

```
Gln Val Gln Leu Leu Gln Ser Gly Ala Val Val Thr Lys Pro Gly Ala
1               5                   10                  15

Ser Val Arg Val Ser Cys Glu Ala Ser Gly Tyr Lys Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Gln Thr Gly Gln Pro Asn Ile Pro Arg Pro Phe
    50                  55                  60

Gln Gly Arg Val Thr Leu Thr Arg His Ala Ser Trp Asp Phe Asp Thr
65                  70                  75                  80

Phe Ser Phe Tyr Met Asp Leu Lys Ala Leu Arg Ser Asp Asp Thr Ala
                85                  90                  95

Ile Tyr Phe Cys Ala Arg Arg Arg Ser Asp Tyr Cys Asp Phe Asp Val
            100                 105                 110

Trp Gly Ser Gly Thr His Val Thr Val Ser Ser
        115                 120
```

<210> SEQ ID NO 37
<211> LENGTH: 107
<212> TYPE: PRT
<213> ORGANISM: Homo sapiens

<400> SEQUENCE: 37

```
Asp Ile Gln Met Thr Gln Ser Pro Ser Ser Leu Ser Ala Ser Ile Gly
1               5                   10                  15

Asp Arg Val Asn Ile Thr Cys Gln Ala Ser Arg Asp Thr Gly Ser Ala
            20                  25                  30

Leu Asn Trp Tyr Gln Gln Lys Val Gly Arg Pro Pro Arg Leu Leu Ile
        35                  40                  45

Ser Ala Val Ser Asn Leu Gly Ala Gly Val Pro Ser Arg Phe Ser Gly
    50                  55                  60

Arg Arg Ser Gly Thr Gln Ser Thr Leu Thr Ile Asn Thr Leu Gln Pro
65                  70                  75                  80

Glu Asp Ile Ala Thr Tyr Phe Cys Gln His Tyr Glu Phe Phe Gly Pro
                85                  90                  95

Gly Thr Lys Val Asp Ile Lys Arg Thr Val Ala
            100                 105
```

<210> SEQ ID NO 38
<211> LENGTH: 125
<212> TYPE: PRT
<213> ORGANISM: Homo sapiens

<400> SEQUENCE: 38

```
Glu Val Gln Leu Val Gln Ser Gly Ser Asp Val Arg Lys Pro Gly Ala
1               5                   10                  15

Thr Val Thr Val Ser Cys Lys Ala Asp Glu Asp Glu Asp Phe Thr
            20                  25                  30

Ala Tyr Asn Tyr Phe Met His Trp Val Arg Gln Ala Pro Gly His Gly
        35                  40                  45

Leu Glu Trp Ile Gly Trp Ile Asn Pro Arg Thr Gly Gln Pro Asn His
    50                  55                  60

Ala Lys Gln Phe Gln Gly Arg Val Thr Leu Thr Arg Glu Arg Ser Thr
65                  70                  75                  80

Ser Thr Val Phe Met Lys Leu Thr Asn Leu Arg Leu Asp Asp Thr Ala
                85                  90                  95

Val Tyr Phe Cys Ala Arg Pro Leu Arg Gly Gly Asp Thr Trp His Tyr
            100                 105                 110

His Ser Trp Gly Arg Gly Thr Ser Leu Thr Val Ser Ser
            115                 120                 125
```

<210> SEQ ID NO 39
<211> LENGTH: 104
<212> TYPE: PRT
<213> ORGANISM: Homo sapiens

<400> SEQUENCE: 39

```
Asp Ile Gln Met Thr Gln Ser Pro Ser Ser Leu Ser Ala Ser Val Gly
1               5                   10                  15

Asp Lys Val Thr Ile Thr Cys Gln Thr Ser Ala Gly Tyr Leu Asn Trp
            20                  25                  30

Tyr Gln Gln Arg Arg Gly Arg Ala Pro Lys Leu Leu Met Tyr Asp Gly
        35                  40                  45

Ser Arg Leu Val Thr Gly Val Pro Ser Arg Phe Ser Gly Arg Arg Trp
    50                  55                  60

Gly Thr Gln Tyr Asn Leu Thr Ile Gly Ser Leu Gln Pro Glu Asp Val
65                  70                  75                  80

Ala Thr Tyr Tyr Cys Gln Val Tyr Glu Phe Phe Gly Pro Gly Thr Arg
                85                  90                  95
```

Leu Asp Leu Lys Arg Thr Val Ala
                100

<210> SEQ ID NO 40
<211> LENGTH: 119
<212> TYPE: PRT
<213> ORGANISM: Homo sapiens

<400> SEQUENCE: 40

Gln Val Gln Leu Val Gln Ser Gly Thr Ala Val Lys Arg Pro Gly Ala
1               5                   10                  15

Ser Val Arg Val Ser Cys Gln Ala Ser Gly Tyr Thr Phe Ile Asp His
            20                  25                  30

Phe Ile Tyr Trp Trp Arg Gln Ala Pro Gly Gln Gly Leu Glu Trp Leu
        35                  40                  45

Gly Trp Ile Asn Pro Leu Thr Ser Gln Pro Ser Tyr Pro Ser Arg Phe
    50                  55                  60

Gln Gly Arg Leu Thr Leu Thr Arg Asp Thr Phe Asp Glu Met Leu Tyr
65                  70                  75                  80

Met Asp Leu Arg Gly Leu Arg Ser Asp Asp Thr Gly Ile Tyr Phe Cys
                85                  90                  95

Ala Arg Arg His Ser Asp Tyr Cys Asp Phe Asp Ile Trp Gly Ser Gly
            100                 105                 110

Thr Gln Ile Ile Val Ser Ser
        115

<210> SEQ ID NO 41
<211> LENGTH: 122
<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
1               5                   10                  15

Asp Arg Val Thr Ile Asn Cys Gln Ala Gly Gln Gly Ile Gly Ser Ser
            20                  25                  30

Leu Asn Trp Tyr Gln Lys Lys Pro Gly Arg Ala Pro Lys Leu Leu Val
        35                  40                  45

His Gly Ala Ser Asn Leu Gln Arg Gly Val Pro Ser Arg Phe Ser Gly
    50                  55                  60

Ser Gly Phe His Thr Thr Phe Thr Leu Thr Ile Ser Ser Leu Gln Pro
65                  70                  75                  80

Asp Asp Val Ala Thr Tyr Phe Cys Ala Val Phe Gln Trp Phe Gly Pro
                85                  90                  95

Gly Thr Lys Val Asp Ile Lys Arg Thr Val Ala Ala Pro Ser Val Phe
            100                 105                 110

Ile Phe Pro Pro Ser Asp Glu Gln Leu Lys
        115                 120

<210> SEQ ID NO 42
<211> LENGTH: 127
<212> TYPE: PRT
<213> ORGANISM: Homo sapiens

<400> SEQUENCE: 42

Ser Gln His Leu Val Gln Ser Gly Thr Gln Val Lys Lys Pro Gly Ala
1               5                   10                  15

Ser Val Arg Val Ser Cys Gln Ala Ser Gly Tyr Thr Phe Thr Asn Tyr

```
                    20                  25                  30

Ile Leu His Trp Trp Arg Gln Ala Pro Gly Gln Gly Leu Glu Trp Met
            35                  40                  45

Gly Leu Ile Lys Pro Val Phe Gly Ala Val Asn Tyr Ala Arg Gln Phe
        50                  55                  60

Gln Gly Arg Ile Gln Leu Thr Arg Asp Ile Tyr Arg Glu Ile Ala Phe
65                  70                  75                  80

Leu Asp Leu Ser Gly Leu Arg Ser Asp Thr Ala Val Tyr Tyr Cys
                85                  90                  95

Ala Arg Asp Glu Ser Gly Asp Asp Leu Lys Trp His Leu His Pro Trp
                100                 105                 110

Gly Gln Gly Thr Gln Val Ile Val Ser Pro Ala Ser Thr Lys Gly
                115                 120                 125

<210> SEQ ID NO 43
<211> LENGTH: 101
<212> TYPE: PRT
<213> ORGANISM: Homo sapiens

<400> SEQUENCE: 43

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
            35                  40                  45

Thr Ser Lys Arg Ala Ser Gly Ile Pro Asp Arg Phe Ser Gly Ser Gln
        50                  55                  60

Phe Gly Lys Gln Tyr Thr Leu Thr Ile Thr Arg Met Glu Pro Glu Asp
65                  70                  75                  80

Phe Ala Gly Tyr Tyr Cys Gln Gln Val Glu Phe Phe Gly Gln Gly Thr
                85                  90                  95

Arg Leu Glu Ile Arg
            100

<210> SEQ ID NO 44
<211> LENGTH: 125
<212> TYPE: PRT
<213> ORGANISM: Homo sapiens

<400> SEQUENCE: 44

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
            35                  40                  45

Ile Gly Trp Val Lys Thr Val Thr Gly Ala Val Asn Phe Gly Ser Pro
        50                  55                  60

Asn Phe Arg His Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Arg Gly Gly Gln Gly Trp Tyr Phe
                100                 105                 110

Asp Leu Trp Gly Arg Gly Thr Leu Ile Val Val Ser Ser
```

-continued

```
            115                 120                 125
```

<210> SEQ ID NO 45
<211> LENGTH: 128
<212> TYPE: PRT
<213> ORGANISM: Homo sapiens

<400> SEQUENCE: 45

```
Gln Val Gln Leu Val Gln Ser Gly Gly Gly Val Lys Lys Pro Gly Thr
1               5                   10                  15

Ser Ala Ser Phe Ser Cys Arg Thr Ser Asp Asp Ile Tyr Asp Asn Glu
            20                  25                  30

Phe Phe Asp Ser Ala Phe Met His Trp Val Arg Leu Ile Pro Gly Gln
        35                  40                  45

Arg Pro Glu Trp Met Gly Trp Met Asn Pro Arg Ser Gly Ala Val Asn
    50                  55                  60

Tyr Ala Arg Gln Leu Gln Pro Arg Val Ser Met Tyr Arg Asp Arg Asp
65                  70                  75                  80

Leu Ser Thr Ala Tyr Met Glu Phe Lys Ser Leu Thr Ser Ala Asp Thr
                85                  90                  95

Gly Thr Tyr Phe Cys Ala Arg Lys Lys Arg Gly Asp Gly Phe Asn Leu
            100                 105                 110

Tyr Phe Asp Leu Trp Gly Arg Gly Ser Gln Val Ile Val Ser Ser Ala
        115                 120                 125
```

<210> SEQ ID NO 46
<211> LENGTH: 126
<212> TYPE: PRT
<213> ORGANISM: Homo sapiens

<400> SEQUENCE: 46

```
Gln Val Gln Leu Val Gln Ser Gly Ser Ala Met Lys Lys Pro Gly Ala
1               5                   10                  15

Ser Val Arg Val Ser Cys Trp Thr Ser Glu Asp Ile Phe Asp Thr Thr
            20                  25                  30

Glu Leu Ile His Trp Val Arg Gln Ala Pro Gly Gln Gly Leu Glu Trp
        35                  40                  45

Ile Gly Trp Val Lys Ala Val Ser Gly Ala Val Asn Tyr Gly Ser Leu
    50                  55                  60

Asp Phe Arg His Arg Val Ser Leu Thr Arg Asp Arg Asp Leu Ser Thr
65                  70                  75                  80

Ala His Met Asp Ile Arg Gly Leu Thr Gln Asp Asp Thr Ala Thr Tyr
                85                  90                  95

Phe Cys Ala Arg Gln Lys Phe Ala Arg Gly Asp Gln Gly Trp Phe Phe
            100                 105                 110

Asp Leu Trp Gly Arg Gly Thr Leu Ile Val Val Ser Ser Ala
        115                 120                 125
```

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcctcaataa agcttgcctt ga                                           22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggcgccactg ctagagattt t                                              21

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aagtagtgtg tgcccgtctg ttrtktgact                                     30

<210> SEQ ID NO 50
<211> LENGTH: 115
<212> TYPE: PRT
<213> ORGANISM: Homo sapiens

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ile Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Trp Tyr Phe Asp Leu Trp Gly Arg Gly Thr Leu Val Thr
            100                 105                 110

Val Ser Ser
        115

<210> SEQ ID NO 51
<211> LENGTH: 119
<212> TYPE: PRT
<213> ORGANISM: Homo sapiens

<400> SEQUENCE: 51

Gln Val Gln Leu Val Gln Ser Gly Ala Ala Leu Lys Lys Pro Gly Ala
1               5                   10                  15

Ser Leu Arg Ile Ser Cys Leu Thr Tyr Gly Tyr Lys Phe Thr Asp His
            20                  25                  30

Leu Ile Tyr Trp Trp Arg Gln Ala Pro Gly Gln Gly Leu Glu Trp Ile
        35                  40                  45

Gly Trp Ile Lys Pro Glu Thr Gly Gln Pro Ser Tyr Ser Tyr Arg Phe
    50                  55                  60

Gln Gly Arg Val Ser Leu Thr Arg Asp Thr Phe Glu Glu Ile Val Phe

```
                65                  70                  75                  80
Met Asp Leu Arg Gly Leu Arg Ser Asp Thr Ala Ile Tyr Phe Cys
                    85                  90                  95

Ala Arg Arg His Ser Asp Tyr Cys Asp Phe Asp Val Trp Gly Ser Gly
                100                 105                 110

Ser Gln Val Ile Val Ser Ser
                115

<210> SEQ ID NO 52
<211> LENGTH: 119
<212> TYPE: PRT
<213> ORGANISM: Homo sapiens

<400> SEQUENCE: 52

Gln Val Gln Leu Val Gln Ser Gly Ala Ala Leu Lys Lys Pro Gly Ala
1               5                   10                  15

Ser Leu Arg Ile Ser Cys Gln Thr Tyr Gly Tyr Lys Phe Thr Asp His
                20                  25                  30

Leu Ile Tyr Trp Trp Arg Gln Ala Pro Gly Gln Gly Leu Glu Trp Ile
                35                  40                  45

Gly Trp Ile Lys Pro Glu Thr Gly Gln Pro Ser Tyr Ser Tyr Arg Phe
            50                  55                  60

Gln Gly Arg Val Ser Leu Thr Arg Asp Thr Phe Glu Glu Ile Val Phe
65                  70                  75                  80

Met Asp Leu Arg Gly Leu Arg Ser Asp Thr Ala Ile Tyr Phe Cys
                    85                  90                  95

Ala Arg Arg His Ser Asp Tyr Cys Asp Phe Asp Val Trp Gly Gly Gly
                100                 105                 110

Ser Gln Val Ile Val Ser Ser
                115

<210> SEQ ID NO 53
<211> LENGTH: 119
<212> TYPE: PRT
<213> ORGANISM: Homo sapiens

<400> SEQUENCE: 53

Gln Val Gln Leu Val Gln Ser Gly Ala Ala Leu Lys Lys Pro Gly Ala
1               5                   10                  15

Ser Leu Arg Ile Ser Cys Gln Thr Tyr Gly Tyr Lys Phe Thr Asp His
                20                  25                  30

Leu Ile Tyr Trp Trp Arg Gln Ala Pro Gly Gln Gly Leu Glu Trp Ile
                35                  40                  45

Gly Trp Ile Lys Pro Glu Thr Gly Gln Pro Ser Tyr Ser Tyr Arg Phe
            50                  55                  60

Gln Gly Arg Val Ser Leu Thr Arg Asp Thr Phe Glu Glu Ile Val Phe
65                  70                  75                  80

Met Asp Leu Arg Gly Leu Arg Ser Asp Thr Ala Ile Tyr Phe Cys
                    85                  90                  95

Ala Arg Arg His Ser Asp Tyr Cys Asp Phe Asp Val Trp Gly Ser Gly
                100                 105                 110

Ser Gln Val Leu Val Ser Ser
                115

<210> SEQ ID NO 54
<211> LENGTH: 119
<212> TYPE: PRT
```

-continued

<213> ORGANISM: Homo sapiens

<400> SEQUENCE: 54

Gln Val Gln Leu Val Gln Ser Gly Ala Ala Leu Lys Lys Pro Gly Ala
1               5                   10                  15

Ser Leu Arg Ile Ser Cys Gln Thr Tyr Gly Tyr Lys Phe Thr Asp His
            20                  25                  30

Leu Ile Tyr Trp Trp Arg Gln Ala Pro Gly Gln Gly Leu Glu Trp Met
        35                  40                  45

Gly Trp Ile Lys Pro Glu Thr Gly Gln Pro Ser Tyr Ser Tyr Arg Phe
    50                  55                  60

Gln Gly Arg Val Ser Leu Thr Arg Asp Thr Phe Glu Glu Ile Val Phe
65                  70                  75                  80

Met Asp Leu Arg Gly Leu Arg Ser Asp Asp Thr Ala Ile Tyr Phe Cys
                85                  90                  95

Ala Arg Arg His Ser Asp Tyr Cys Asp Phe Asp Val Trp Gly Ser Gly
            100                 105                 110

Ser Gln Val Ile Val Ser Ser
        115

<210> SEQ ID NO 55
<211> LENGTH: 119
<212> TYPE: PRT
<213> ORGANISM: Homo sapiens

<400> SEQUENCE: 55

Gln Val Gln Leu Val Gln Ser Gly Ala Ala Leu Lys Lys Pro Gly Ala
1               5                   10                  15

Ser Leu Arg Ile Ser Cys Gln Thr Tyr Gly Tyr Lys Phe Thr Asp His
            20                  25                  30

Leu Ile Tyr Trp Trp Arg Gln Ala Pro Gly Gln Gly Leu Glu Trp Ile
        35                  40                  45

Gly Trp Ile Lys Pro Glu Thr Gly Gln Pro Ser Tyr Ser Tyr Arg Phe
    50                  55                  60

Gln Gly Arg Val Ser Leu Thr Arg Asp Thr Phe Glu Glu Ile Ala Phe
65                  70                  75                  80

Met Asp Leu Arg Gly Leu Arg Ser Asp Asp Thr Ala Ile Tyr Phe Cys
                85                  90                  95

Ala Arg Arg His Thr Asp Tyr Cys Val Phe Asp Val Trp Gly Ser Gly
            100                 105                 110

Ser Gln Ile Ile Val Ser Ser
        115

<210> SEQ ID NO 56
<211> LENGTH: 119
<212> TYPE: PRT
<213> ORGANISM: Homo sapiens

<400> SEQUENCE: 56

Gln Val Gln Leu Val Gln Ser Gly Ala Ala Leu Lys Lys Pro Gly Ala
1               5                   10                  15

Ser Val Arg Ile Ser Cys Gln Ala Tyr Gly Tyr Lys Phe Thr Asp His
            20                  25                  30

Leu Ile Tyr Trp Trp Arg Gln Ala Pro Gly Gln Gly Leu Glu Trp Ile
        35                  40                  45

Gly Trp Ile Lys Pro Glu Thr Gly Gln Pro Ser Tyr Ser Tyr Lys Phe
    50                  55                  60

```
Gln Gly Arg Val Thr Leu Thr Arg Asp Thr Phe Glu Ile His Phe
 65                  70                  75                  80

Met Asp Leu Arg Gly Leu Arg Tyr Asp Asp Thr Ala Thr Tyr Phe Cys
                 85                  90                  95

Ala Arg Arg His Ser Asp Tyr Cys Asp Phe Asp Val Trp Gly Ser Gly
                100                 105                 110

Ser Gln Val Ser Val Ser Ser
            115

<210> SEQ ID NO 57
<211> LENGTH: 119
<212> TYPE: PRT
<213> ORGANISM: Homo sapiens

<400> SEQUENCE: 57

Gln Val Gln Leu Val Gln Ser Gly Ala Ala Leu Lys Lys Pro Gly Ala
  1               5                  10                  15

Ser Val Arg Ile Ser Cys Gln Ala Tyr Gly Tyr Lys Phe Thr Asp His
                 20                  25                  30

Leu Ile Tyr Trp Trp Arg Gln Ala Pro Gly Gln Gly Leu Glu Trp Ile
             35                  40                  45

Gly Trp Ile Lys Pro Glu Thr Gly Gln Pro Ser Tyr Ala Tyr Lys Phe
 50                  55                  60

Gln Gly Arg Val Thr Leu Thr Arg Asp Thr Phe Glu Ile His Phe
 65                  70                  75                  80

Met Asp Leu Arg Gly Val Arg Asn Asp Asp Thr Ala Thr Tyr Phe Cys
                 85                  90                  95

Ala Arg Arg His Ser Asp Tyr Cys Asp Phe Asp Val Trp Gly Ser Gly
                100                 105                 110

Ser Gln Val Ile Val Ser Ser
            115

<210> SEQ ID NO 58
<211> LENGTH: 119
<212> TYPE: PRT
<213> ORGANISM: Homo sapiens

<400> SEQUENCE: 58

Gln Val Gln Leu Val Gln Ser Gly Ala Ala Leu Lys Lys Pro Gly Ala
  1               5                  10                  15

Ser Val Arg Ile Ser Cys Gln Ala Tyr Gly Tyr Lys Phe Thr Asp Tyr
                 20                  25                  30

Leu Ile His Trp Trp Arg Gln Ala Pro Gly Gln Gly Leu Glu Trp Ile
             35                  40                  45

Gly Trp Ile Lys Pro Glu Thr Gly Gln Pro Ser Tyr Ser Tyr Lys Phe
 50                  55                  60

Gln Gly Arg Val Thr Leu Thr Arg Asp Thr Phe Glu Ile Leu Phe
 65                  70                  75                  80

Met Asp Leu Arg Gly Leu Arg Ser Asp Thr Ala Ile Tyr Phe Cys
                 85                  90                  95

Ala Arg Arg His Ser Asp Tyr Cys Asp Phe Asp Val Trp Gly Ser Gly
                100                 105                 110

Ser Gln Val Ile Val Ser Ser
            115

<210> SEQ ID NO 59
```

```
<211> LENGTH: 127
<212> TYPE: PRT
<213> ORGANISM: Homo sapiens

<400> SEQUENCE: 59

Gln Pro Gln Leu Val Gln Ser Gly Ser Gly Ala Glu Val Lys Lys Pro
1               5                   10                  15

Gly Ala Ser Val Arg Ile Ser Cys Glu Ala Ser Glu Tyr Asn Val Phe
                20                  25                  30

Asp His Phe Met Gln Trp Val Arg Gln Ala Pro Gly Gln Gly Leu Glu
            35                  40                  45

Trp Met Gly Trp Ile Asn Pro Arg Gly Gly Tyr Pro Ser Tyr Ser Pro
50                  55                  60

Arg Phe Gln Gly Arg Leu Thr Phe Thr Arg Gln Pro Ser Trp Asp Asp
65                  70                  75                  80

Ser Ser Val Thr Phe His Met Glu Leu Arg Gly Leu Arg His Asp Asp
                85                  90                  95

Thr Ala Val Tyr Tyr Cys Ala Arg Pro His Ser Pro Asp Ala Trp
            100                 105                 110

Ser Leu Asp Val Trp Gly Arg Gly Thr Leu Val Thr Val Ser Ser
        115                 120                 125

<210> SEQ ID NO 60
<211> LENGTH: 123
<212> TYPE: PRT
<213> ORGANISM: Homo sapiens

<400> SEQUENCE: 60

Gln Val Gln Leu Val Gln Ser Gly Ala Asp Val Lys Lys Pro Gly Ala
1               5                   10                  15

Ser Val Thr Val Ser Cys Lys Thr Asp Glu Asp Glu Asp Phe Arg
                20                  25                  30

Ala His Leu Val Gln Trp Met Arg Gln Ala Pro Gly Gln Arg Leu Glu
            35                  40                  45

Trp Val Gly Trp Ile Lys Pro Gln Thr Gly Gln Pro Ser Tyr Ala Gln
50                  55                  60

Lys Phe Gln Gly Arg Val Thr Leu Thr Arg Glu Val Ser Thr Ser Thr
65                  70                  75                  80

Val Phe Leu Gln Leu Arg Asn Leu Arg Ser Asp Asp Thr Ala Val Tyr
                85                  90                  95

Tyr Cys Ala Arg Pro Arg Gly Gly Arg Asp Asn Trp Ser Phe His Val
            100                 105                 110

Trp Gly Arg Gly Thr Leu Val Thr Val Ser Ser
        115                 120

<210> SEQ ID NO 61
<211> LENGTH: 119
<212> TYPE: PRT
<213> ORGANISM: Homo sapiens

<400> SEQUENCE: 61

Gln Val Gln Leu Val Gln Ser Gly Thr Ala Val Lys Lys Pro Gly Ala
1               5                   10                  15

Ser Val Arg Val Ser Cys Gln Ala Ser Gly Tyr Thr Phe Thr Asp Tyr
                20                  25                  30

Phe Ile Tyr Trp Trp Arg Gln Ala Pro Gly Gln Gly Leu Glu Trp Leu
            35                  40                  45
```

Gly Trp Ile Asn Pro Arg Thr Ser Gln Pro Ser Tyr Pro Tyr Arg Phe
    50                  55                  60

Gln Gly Arg Val Thr Leu Thr Arg Asp Ile Phe Glu Glu Met Leu Tyr
65                  70                  75                  80

Met Asp Leu Arg Gly Leu Arg Ser Asp Thr Gly Ile Tyr Phe Cys
                85                  90                  95

Ala Arg Arg His Ser Asp Tyr Cys Asp Phe Asp Ile Trp Gly Ser Gly
                100                 105                 110

Thr Gln Ile Ile Val Ser Ser
        115

<210> SEQ ID NO 62
<211> LENGTH: 127
<212> TYPE: PRT
<213> ORGANISM: Homo sapiens

<400> SEQUENCE: 62

Gln Val Gln Leu Val Pro Ser Gly Ser Gly Val Lys Lys Pro Gly Ala
1               5                   10                  15

Ser Val Arg Val Ser Cys Trp Thr Ser Glu Asp Ile Phe Glu Arg Thr
                20                  25                  30

Glu Leu Ile His Trp Val Arg Gln Ala Pro Gly Gln Gly Leu Glu Trp
            35                  40                  45

Ile Gly Trp Val Lys Thr Val Thr Gly Ala Val Asn Phe Gly Ser Leu
    50                  55                  60

Asp Phe Arg His Arg Ile Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Ser Arg Tyr Thr Gly Gly Gln Gly
                100                 105                 110

Trp Tyr Phe Asp Leu Trp Gly Arg Gly Thr His Ile Val Val Ser
            115                 120                 125

<210> SEQ ID NO 63
<211> LENGTH: 94
<212> TYPE: PRT
<213> ORGANISM: Homo sapiens

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp
                85                  90

<210> SEQ ID NO 64
<211> LENGTH: 95
<212> TYPE: PRT
<213> ORGANISM: Homo sapiens

```
<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser
                85                  90                  95

<210> SEQ ID NO 65
<211> LENGTH: 94
<212> TYPE: PRT
<213> ORGANISM: Homo sapiens

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu
                85                  90

<210> SEQ ID NO 66
<211> LENGTH: 104
<212> TYPE: PRT
<213> ORGANISM: Homo sapiens

<400> SEQUENCE: 66

Asp Ile Gln Met Thr Gln Ser Pro Ser Ser Leu Ser Ala Ser Val Gly
1               5                   10                  15

Asp Thr Val Thr Ile Thr Cys Gln Thr Asn Lys Gly Tyr Leu Asn Trp
            20                  25                  30

Tyr Gln Gln Arg Arg Gly Arg Ala Pro Lys Leu Leu Met Tyr Asp Gly
        35                  40                  45

Ser Lys Leu Val Thr Gly Val Pro Ser Arg Leu Ser Gly Arg Arg Trp
50                  55                  60

Gly Thr Gln Tyr Asn Leu Thr Ile Gly Ser Leu Gln Pro Glu Asp Ile
65                  70                  75                  80

Ala Thr Tyr Tyr Cys Gln Val Tyr Glu Phe Phe Gly Pro Gly Thr Arg
                85                  90                  95

Leu Asp Leu Lys Arg Thr Val Ala
            100

<210> SEQ ID NO 67
<211> LENGTH: 104
<212> TYPE: PRT
```

<213> ORGANISM: Homo sapiens

<400> SEQUENCE: 67

Asp Ile Gln Met Thr Gln Ser Pro Ser Ser Leu Ser Ala Ser Val Gly
1               5                   10                  15

Asp Thr Val Thr Ile Thr Cys Gln Thr Asn Lys Gly Tyr Leu Asn Trp
            20                  25                  30

Tyr Gln Gln Lys Arg Gly Arg Ala Pro Lys Leu Leu Met Tyr Asp Gly
        35                  40                  45

Ser Lys Leu Val Thr Gly Val Pro Ser Arg Leu Ser Gly Arg Arg Trp
    50                  55                  60

Gly Thr Gln Tyr Asn Leu Thr Ile Gly Ser Leu Gln Pro Glu Asp Ile
65                  70                  75                  80

Ala Thr Tyr Tyr Cys Gln Val Tyr Glu Phe Phe Gly Pro Gly Thr Arg
                85                  90                  95

Leu Asp Leu Lys Arg Thr Val Ala
            100

<210> SEQ ID NO 68
<211> LENGTH: 104
<212> TYPE: PRT
<213> ORGANISM: Homo sapiens

<400> SEQUENCE: 68

Asp Ile Gln Met Thr Gln Ser Pro Ser Ser Leu Ser Ala Ser Val Gly
1               5                   10                  15

Asp Thr Val Thr Ile Thr Cys Gln Thr Asn Lys Gly Tyr Leu Asn Trp
            20                  25                  30

Tyr Gln Gln Arg Arg Gly Arg Ala Pro Lys Leu Leu Met Tyr Asp Gly
        35                  40                  45

Ser Lys Leu Val Thr Gly Val Pro Ser Arg Leu Ser Gly Arg Arg Trp
    50                  55                  60

Gly Thr Gln Tyr Asn Leu Thr Ile Gly Ser Leu Gln Pro Glu Asp Ile
65                  70                  75                  80

Ala Thr Tyr Tyr Cys Gln Val Tyr Glu Phe Phe Gly Pro Gly Thr Arg
                85                  90                  95

Leu Asp Leu Lys Arg Thr Val Ala
            100

<210> SEQ ID NO 69
<211> LENGTH: 104
<212> TYPE: PRT
<213> ORGANISM: Homo sapiens

<400> SEQUENCE: 69

Asp Ile Gln Met Thr Gln Ser Pro Ser Ser Leu Ser Ala Ser Val Gly
1               5                   10                  15

Asp Thr Val Thr Ile Thr Cys Gln Thr Asn Lys Gly Tyr Leu Asn Trp
            20                  25                  30

Tyr Gln Gln Arg Arg Gly Arg Ala Pro Lys Leu Leu Met Tyr Asp Gly
        35                  40                  45

Ser Lys Leu Val Thr Gly Val Pro Ser Arg Leu Ser Gly Arg Arg Trp
    50                  55                  60

Gly Thr Gln Tyr Asn Leu Thr Ile Gly Ser Leu Gln Pro Glu Asp Ile
65                  70                  75                  80

Ala Thr Tyr Tyr Cys Gln Val Tyr Glu Phe Phe Gly Pro Gly Thr Arg
                85                  90                  95

-continued

```
Leu Asp Leu Lys Arg Thr Val Ala
            100

<210> SEQ ID NO 70
<211> LENGTH: 104
<212> TYPE: PRT
<213> ORGANISM: Homo sapiens

<400> SEQUENCE: 70

Asp Ile Gln Met Thr Gln Ser Pro Ser Ser Leu Ser Ala Ser Val Gly
1               5                   10                  15

Asp Thr Val Thr Ile Thr Cys Gln Thr Asn Lys Gly Tyr Leu Asn Trp
            20                  25                  30

Tyr Gln Gln Arg Arg Gly Arg Ala Pro Lys Leu Leu Met Tyr Asp Gly
        35                  40                  45

Ser Lys Leu Val Thr Gly Val Pro Ser Arg Leu Ser Gly Arg Arg Trp
    50                  55                  60

Gly Thr Gln Tyr Asn Leu Thr Ile Gly Ser Leu Gln Pro Glu Asp Ile
65                  70                  75                  80

Ala Thr Tyr Tyr Cys Gln Val Tyr Glu Phe Phe Gly Pro Gly Thr Arg
                85                  90                  95

Leu Asp Leu Lys Arg Thr Val Ala
            100

<210> SEQ ID NO 71
<211> LENGTH: 104
<212> TYPE: PRT
<213> ORGANISM: Homo sapiens

<400> SEQUENCE: 71

Asp Ile Gln Met Thr Gln Ser Pro Ser Ser Leu Ser Ala Ser Val Gly
1               5                   10                  15

Asp Thr Val Thr Ile Thr Cys His Thr Asn Lys Gly Tyr Leu Asn Trp
            20                  25                  30

Tyr Gln Gln Arg Arg Gly Arg Ala Pro Lys Leu Leu Met Phe Asp Gly
        35                  40                  45

Ser Lys Leu Val Thr Gly Val Pro Ser Arg Phe Ser Gly Arg Arg Trp
    50                  55                  60

Gly Thr Gln Tyr Asn Leu Thr Ile Gly Ser Leu Gln Pro Glu Asp Ile
65                  70                  75                  80

Ala Thr Tyr Tyr Cys Gln Val Tyr Glu Val Phe Gly Pro Gly Thr Arg
                85                  90                  95

Leu Asp Leu Lys Arg Thr Val Ala
            100

<210> SEQ ID NO 72
<211> LENGTH: 104
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Thr Val Thr Ile Thr Cys His Thr Asn Lys Gly Tyr Leu Asn Trp
            20                  25                  30

Tyr Gln Gln Arg Arg Gly Arg Ala Pro Lys Leu Leu Met Phe Asp Gly
        35                  40                  45
```

-continued

Ser Lys Leu Val Thr Gly Val Pro Ser Arg Phe Ser Gly Arg Arg Trp
    50                  55                  60

Gly Thr Gln Tyr Asn Leu Thr Ile Gly Ser Leu Gln Pro Glu Asp Ile
65                  70                  75                  80

Ala Thr Tyr Tyr Cys Gln Val Tyr Glu Val Phe Gly Pro Gly Thr Arg
                85                  90                  95

Leu Asp Leu Lys Arg Thr Val Ala
            100

<210> SEQ ID NO 73
<211> LENGTH: 104
<212> TYPE: PRT
<213> ORGANISM: Homo sapiens

<400> SEQUENCE: 73

Asp Ile Gln Met Thr Gln Ser Pro Ser Ser Leu Ser Ala Ser Val Gly
1               5                   10                  15

Asp Thr Val Thr Ile Thr Cys Gln Thr Thr Lys Gly Tyr Leu Asn Trp
            20                  25                  30

Tyr Gln Gln Arg Arg Gly Arg Ala Pro Lys Leu Leu Met Phe Asp Gly
        35                  40                  45

Ser Lys Leu Val Thr Gly Val Pro Ser Arg Phe Ser Gly Arg Arg Trp
    50                  55                  60

Gly Thr Gln Tyr Asn Leu Thr Ile Gly Ser Leu Gln Pro Glu Asp Leu
65                  70                  75                  80

Ala Thr Tyr Tyr Cys Gln Val Tyr Glu Phe Phe Gly Pro Gly Thr Arg
                85                  90                  95

Leu Asp Leu Lys Arg Thr Val Ala
            100

<210> SEQ ID NO 74
<211> LENGTH: 107
<212> TYPE: PRT
<213> ORGANISM: Homo sapiens

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Ser Asn Ser
            20                  25                  30

Leu Asn Trp Tyr Gln Gln Lys Pro Gly Lys Ala Pro Arg Leu Leu Ile
        35                  40                  45

Tyr Gly Thr Ser Thr Leu Gln Arg Gly Val Pro Ser Arg Phe Ser Gly
    50                  55                  60

Ser Gly Ser Gly Thr Arg Phe Thr Val Thr Ile Asn Ser Leu Gln Pro
65                  70                  75                  80

Glu Asp Ile Ala Thr Tyr Phe Cys Gln His Asn Glu Phe Phe Gly Arg
                85                  90                  95

Gly Thr Lys Val Asp Ile Lys Arg Thr Val Ala
            100                 105

<210> SEQ ID NO 75
<211> LENGTH: 108
<212> TYPE: PRT
<213> ORGANISM: Homo sapiens

<400> SEQUENCE: 75

Asp Ile Gln Met Thr Gln Ser Pro Ser Ser Val Ser Ala Ser Val Gly

```
                1               5                   10                  15
            Asp Arg Val Thr Ile Thr Cys Gln Ala Ser Arg Asp Thr Asp Asn Ser
                            20                  25                  30

Leu Thr Trp Tyr Gln Gln Lys Pro Gly Arg Pro Pro Lys Leu Leu Ile
                        35                  40                  45

Tyr His Val Val Asn Leu Gly Pro Gly Val Pro Ser Arg Phe Ser Gly
                        50                  55                  60

Ser Ala Ser Ser Ala Thr Gln Ser Thr Leu Ile Ile Ser Asp Phe Gln
            65                  70                  75                  80

Pro Asp Asp Val Ala Thr Tyr Phe Cys Gln Asn Tyr Glu Phe Phe Gly
                            85                  90                  95

Pro Gly Thr Lys Val Glu Ile Lys Arg Thr Val Ala
                        100                 105

<210> SEQ ID NO 76
<211> LENGTH: 103
<212> TYPE: PRT
<213> ORGANISM: Homo sapiens

<400> SEQUENCE: 76

Asp Ile Gln Met Thr Gln Ser Pro Ser Ser Leu Ser Ala Arg Val Gly
            1               5                   10                  15

Asp Lys Val Thr Ile Thr Tyr Gln Thr Ser Ala Gly Tyr Leu Asn Trp
                            20                  25                  30

Tyr Gln Gln Arg Arg Gly Arg Ala Pro Lys Leu Leu Met Tyr Asp Gly
                        35                  40                  45

Ser Arg Leu Val Thr Gly Ala Pro Ser Arg Phe Ser Gly Arg Arg Trp
                        50                  55                  60

Gly Thr Gln Tyr Asn Leu Thr Ile Gly Ser Leu Gln Pro Glu Asp Ile
            65                  70                  75                  80

Ala Thr Tyr Tyr Cys Gln Val Tyr Glu Phe Phe Gly Pro Gly Thr Arg
                            85                  90                  95

Leu Asp Leu Lys Arg Thr Val
                        100

<210> SEQ ID NO 77
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: (5)..(5)
<223> OTHER INFORMATION: Xaa can be Ile or Leu
<220> FEATURE:
<221> NAME/KEY: VARIANT
<222> LOCATION: (6)..(6)
<223> OTHER INFORMATION: Xaa can be Asn or Asp

<400> SEQUENCE: 77

Gly Tyr Glu Phe Xaa Xaa Cys
            1               5

<210> SEQ ID NO 78
<211> LENGTH: 6
<212> TYPE: PRT
<213> ORGANISM: Artificial
<220> FEATURE:
<223> OTHER INFORMATION: Synthetic

<400> SEQUENCE: 78
```

```
Lys Pro Arg Gly Gly Ala
1               5

<210> SEQ ID NO 79
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: (3)..(3)
<223> OTHER INFORMATION: Xaa can be Asn or Tyr
<220> FEATURE:
<221> NAME/KEY: VARIANT
<222> LOCATION: (5)..(5)
<223> OTHER INFORMATION: Xaa can be Asp or Thr

<400> SEQUENCE: 79

Gly Lys Xaa Cys Xaa Tyr Asn Trp Asp Phe Glu His
1               5                   10

<210> SEQ ID NO 80
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: (3)..(3)
<223> OTHER INFORMATION: Xaa can be Asn or Tyr
<220> FEATURE:
<221> NAME/KEY: VARIANT
<222> LOCATION: (5)..(5)
<223> OTHER INFORMATION: Xaa can be Asp or Thr

<400> SEQUENCE: 80

Gly Lys Xaa Cys Xaa Ala Arg Asp Tyr Tyr Asn Trp Asp Phe Glu His
1               5                   10                  15

<210> SEQ ID NO 81
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: (5)..(5)
<223> OTHER INFORMATION: Xaa can be Ser or Tyr

<400> SEQUENCE: 81

Arg Thr Ser Gln Xaa Gly Ser Leu Ala
1               5

<210> SEQ ID NO 82
<211> LENGTH: 7
<212> TYPE: PRT
<213> ORGANISM: Artificial
<220> FEATURE:
<223> OTHER INFORMATION: Synthetic

<400> SEQUENCE: 82

Ser Gly Ser Thr Arg Ala Ala
1               5

<210> SEQ ID NO 83
<211> LENGTH: 5
```

```
<212> TYPE: PRT
<213> ORGANISM: Artificial
<220> FEATURE:
<223> OTHER INFORMATION: Synthetic

<400> SEQUENCE: 83

Gln Gln Tyr Glu Phe
1               5

<210> SEQ ID NO 84
<211> LENGTH: 107
<212> TYPE: PRT
<213> ORGANISM: Homo sapiens

<400> SEQUENCE: 84

Glu Ile Val Leu Thr Gln Ser Pro Ala Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Ala Asp Tyr Asn Leu Ser Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg Thr Val Ala
            100                 105

<210> SEQ ID NO 85
<211> LENGTH: 125
<212> TYPE: PRT
<213> ORGANISM: Homo sapiens

<400> SEQUENCE: 85

Gln Val Arg Leu Ser Gln Ser Gly Gly Gln Met Lys Lys Pro Gly Glu
1               5                   10                  15

Ser Met Arg Leu Ser Cys Arg Ala Ser Gly Tyr Glu Phe Leu Asn Cys
            20                  25                  30

Pro Ile Asn Trp Ile Arg Leu Ala Pro Gly Arg Arg Pro Glu Trp Met
        35                  40                  45

Gly Trp Leu Lys Pro Arg Trp Gly Ala Val Asn Tyr Ala Arg Lys Phe
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ser Asp Asp Thr Ala Val Tyr Phe Cys
                85                  90                  95

Thr Arg Gly Lys Tyr Cys Thr Ala Arg Asp Tyr Tyr Asn Trp Asp Phe
            100                 105                 110

Glu His Trp Gly Arg Gly Ala Pro Val Thr Val Ser Ser
        115                 120                 125
```

HIV-1 GP120 CD4 BINDING SITE ANTIBODIES TARGETING HIV ESCAPE MUTANTS

CROSS-REFERENCE TO RELATED APPLICATION(S)

This application is a continuation of U.S. application Ser. No. 15/835,319 filed on Dec. 7, 2017, now U.S. patent Ser. No. 11/149,081, which is a continuation of U.S. patent application Ser. No. 13/924,469, filed Jun. 21, 2013, now U.S. Pat. No. 9,879,068, which claims priority to and the benefit of U.S. Provisional Application Ser. No. 61/662,594, filed Jun. 21, 2012. The entire contents of these applications are incorporated herein by reference in their entirety.

STATEMENT REGARDING FEDERALLY SPONSORED RESEARCH OR DEVELOPMENT

This invention was made with government support under Grant No. AI100148 and Grant No. AI100663 awarded by the National Institutes of Health. The government has certain rights in the invention.

INCORPORATION BY REFERENCE

The instant application contains a Sequence Listing which has been submitted in ASCII format via EFS-Web and is hereby incorporated by reference in its entirety. Said ASCII copy, amended on Sep. 30, 2023, is named 070413.20601_SeqList.txt and is 78,400 bytes in size.

TECHNICAL FIELD

This application is directed to a gp120 anti-CD4 binding site (anti-CD4bs) antibody composition that has improved potency and breadth against the human immunodeficiency virus, (HIV) which causes acquired immunodeficiency syndrome (AIDS).

BACKGROUND

Three decades after the emergence of HIV there is still no vaccine, and AIDS remains a threat to global public health. However, some HIV-infected individuals eventually develop broadly neutralizing antibodies (bNAbs), i.e., antibodies that neutralize a large panel of HIV viruses and that can delay viral rebound in HIV patients. Such antibodies are relevant to vaccine development, as evidenced by the prevention of infection observed after passive transfer to macaques.

The NIH$^{45-46}$ antibody that was isolated in a screen using single cell cloning techniques (Scheid et al., 2009, *J. Immunol Methods* 343:65-67; Scheid et al., 2011, Science 333:1633-1637, the entire contents of both of which are herein incorporated by reference), is a more potent clonal variant of VRC01, a bNAb directed against the CD4 binding site (CD4bs) of gp120 (Wu et al., 2010, *Science* 329:856-861; and Zhou et al., 2010, *Science* 329:811-817, the entire contents of both of which are herein incorporated by reference). Enhancing the efficacy of bNAbs, and in particular, designing bNAbs that retain potency against escape mutants selected during exposure to bNAbs, would facilitate their use as therapeutics.

SUMMARY

In some embodiments, a composition includes an isolated anti-CD4 binding site (anti-CD4bs) potent VRC01-like (PVL) antibody having a heavy chain and a light chain, the heavy chain including a first substitution at a position equivalent to Phe43 of a CD4 receptor protein, the heavy chain substitution being selected from the group consisting of glycine, histidine, arginine, glutamine, asparagine, lysine, glutamic acid, and aspartic acid; and a second substitution of tryptophan at position 47 of the heavy chain, selected from valine, isoleucine, and threonine; and the light chain including a substitution of tyrosine at position 28 of the light chain for serine.

In some embodiments a method of preventing or treating an HIV infection or an HIV-related disease includes administering a therapeutically effective amount of a composition, the composition including an isolated anti-CD4 binding site (anti-CD4bs) potent VRC01-like (PVL) antibody having a heavy chain and a light chain, the heavy chain including a first substitution at a position equivalent to Phe43 of a CD4 receptor protein, the heavy chain substitution being selected from the group consisting of glycine, histidine, arginine, glutamine, asparagine, lysine, glutamic acid, and aspartic acid; and a second substitution of tryptophan at position 47 of the heavy chain, selected from valine, isoleucine, and threonine; and the light chain including a substitution of tyrosine at position 28 of the light chain for serine.

In some embodiments, a method of preventing or treating an HIV infection or an HIV-related disease, the method comprising administering a therapeutically effective amount of at least two antibodies, the first antibody comprising the composition described above and the second antibody comprising 10-1074 antibody or PG9 antibody.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

Figure 1B:
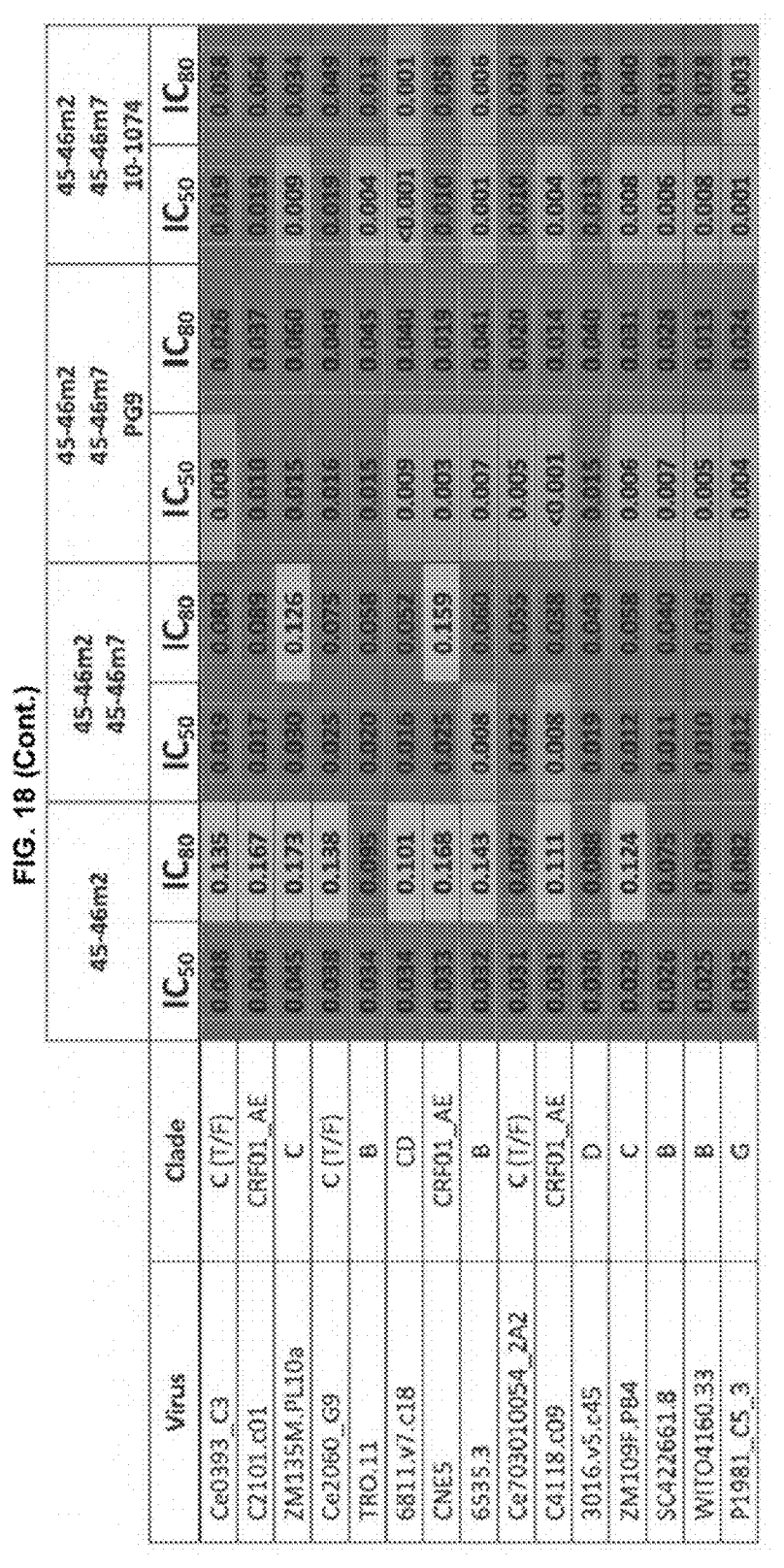

FIG. 1 is a table listing NIH45-46m mutants, according to embodiments of the present invention.

Figure 3:
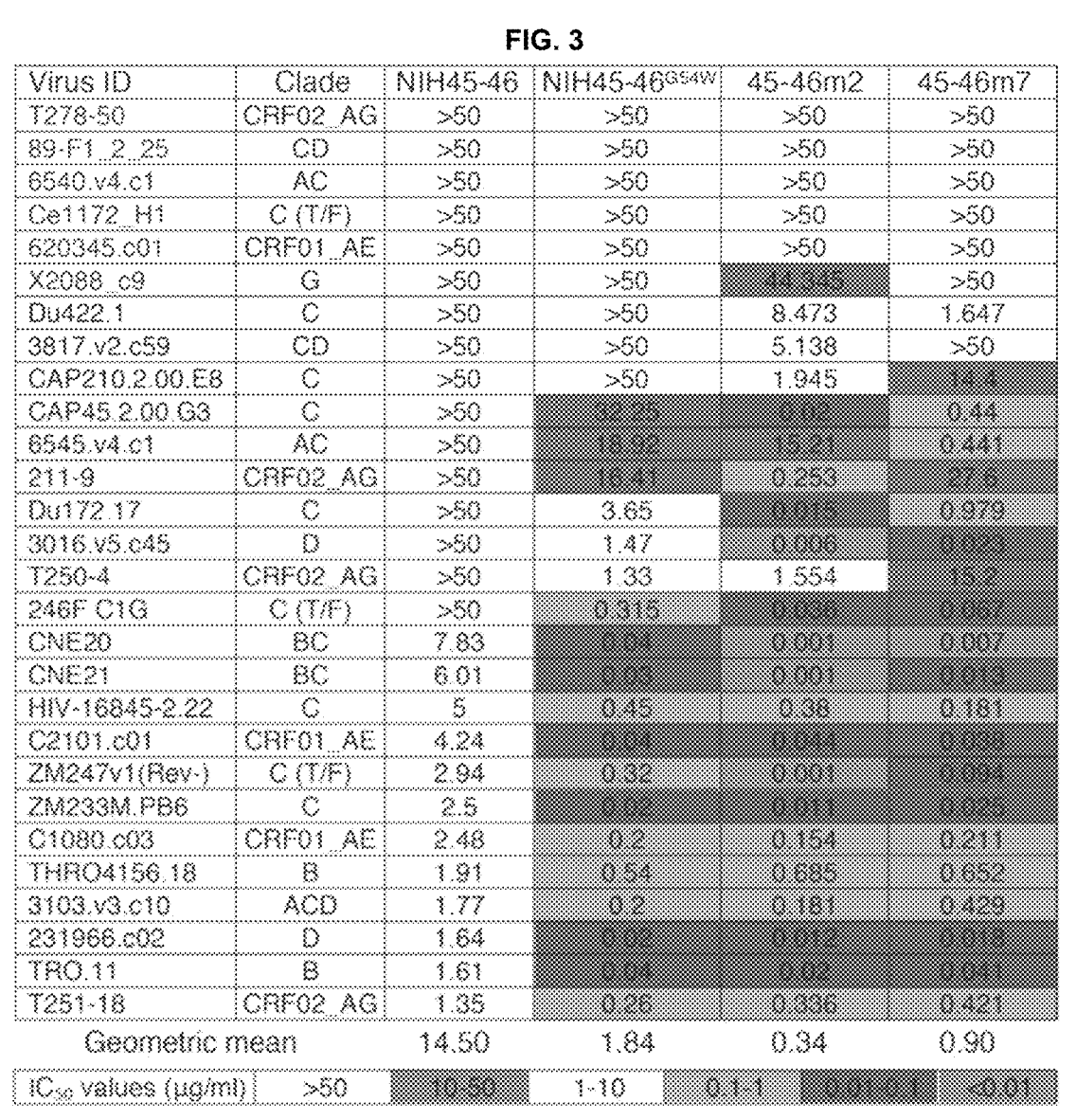

FIG. 3 is a table showing $IC_{50}$ values (μg/ml) for NIH45-46, NIH45-46$^{G54W}$, 45-46m2 and 45-46m7 against 28 strains that are resistant to, or poorly neutralized by, NIH45-46. Strains marked in blue have an altered N/DNGG motif. $IC_{50}$s were derived from curves generated from data points obtained in duplicate or triplicate, according to embodiments of the present invention.

FIG. 5B is table of IC50 values (μg/ml) for NIH45-46$^{G54W}$, 45-46m2, and 45-46m7 against viral clones from patient VC10042, in which the reported IC50 values represent the average of two independent experiments, each with two replicates, according to embodiments of the present invention.

FIG. 9 is a table listing average IC$_{50}$ values (μg/ml) derived from in vitro neutralization assays for 45-4m antibodies against YU-2 mutants, in which three or more independent neutralization assays were performed for each mutant, according to embodiments of the present invention.

FIG. 10 is a table listing the IC50 values (μg/ml) derived from in vitro neutralization assays for selected 45-4m antibodies against YU-2 mutant strains, in which five independent neutralization assays were performed for each mutant, according to embodiments of the present invention.

FIG. 12A shows a sequence alignment of YU-2, the two YU-2 Ala281$_{gp120}$ mutants, and the three known HIV strains with a potential N-linked glycosylation site at Asn279$_{gp120}$, in which the glycosylation potential for Asn279$_{gp120}$ was calculated for each strain using NetNGlyc 1.0 Server, according to embodiments of the present invention.

FIG. 12B shows replication profiles of YU-2 escape mutants from two independent experiments comparing the replication of various YU-2 escape mutants to YU-2 WT in PBMC cell culture, in which levels of virus in the supernatant were determined by measuring p24 levels at various time points after inoculation, and each value represents the average of two replicates each from two independent experiments, according to embodiments of the present invention.

FIG. 14A is the analysis for HIV-1$_{YU2}$-infected humanized mice treated with a combination of two [45-46m2+45-46m7, labeled 45-46m2/m7] bNAbs and FIG. 14B is the analysis for HIV-1$_{YU2}$-infected humanized mice treated with a combination of three [45-46m2/m7+10-1074] bNAbs and the sequences of gp 120s from escape mutant viruses were determined; where individual gp120 nucleotide sequences are represented by horizontal gray bars with silent mutations indicated in green and replacement mutations in red; and shaded vertical lines indicate regions that allowed escape from NIH45-46$^{G54W}$ (amino acid positions 280 and 459) and from 10-1074 (amino acid position 332); and all substitutions are relative to HIV-1$_{YU2}$ (acc. number M93258) and numbered according to HXB2, according to embodiments of the present invention.

FIG. 16 is a table of IC80 values for NIH45-46$^{G54W}$, 45-46m2, and 45-46m7, 45-46m25 and 45-46m28 antibodies tested against the indicated viral strains, according to embodiments of the present invention.

FIG. 17 is a table of the crystallographic data collection and refinement statistics for the 45-46m2/93TH057 crystal structure, according to embodiments of the present invention.

FIG. 18 is a table of IC$_{50}$ and IC$_{80}$ values for 45-46m2 antibody, 45-46m2/45-46m7 combined antibodies, 45-46m2/45-46m7/PG9 combined antibodies, and 45-46m2/45-46m7/10-1074 combined antibodies tested against the indicated viral strains, according to embodiments of the present invention.

FIGS. 19A-19B show mutation analysis of gp120 sequences during antibody therapy in which env sequences were cloned from mice treated with a combination of 45-46m2 and 45-46m7 as shown in FIG. 19A or 45-46m2, 45-46m7 and 10-1074, as shown in FIG. 19B, where dots indicate no change compared with the parental YU-2 sequence and mutations are indicated with a single-letter amino acid code; the three regions of Env that can potentially harbor escape mutations are shown; and the N/DNGG motif and position 332 (site of 10-1074-induced mutations) are highlighted in red, according to embodiments of the present invention.

Figure 20B:
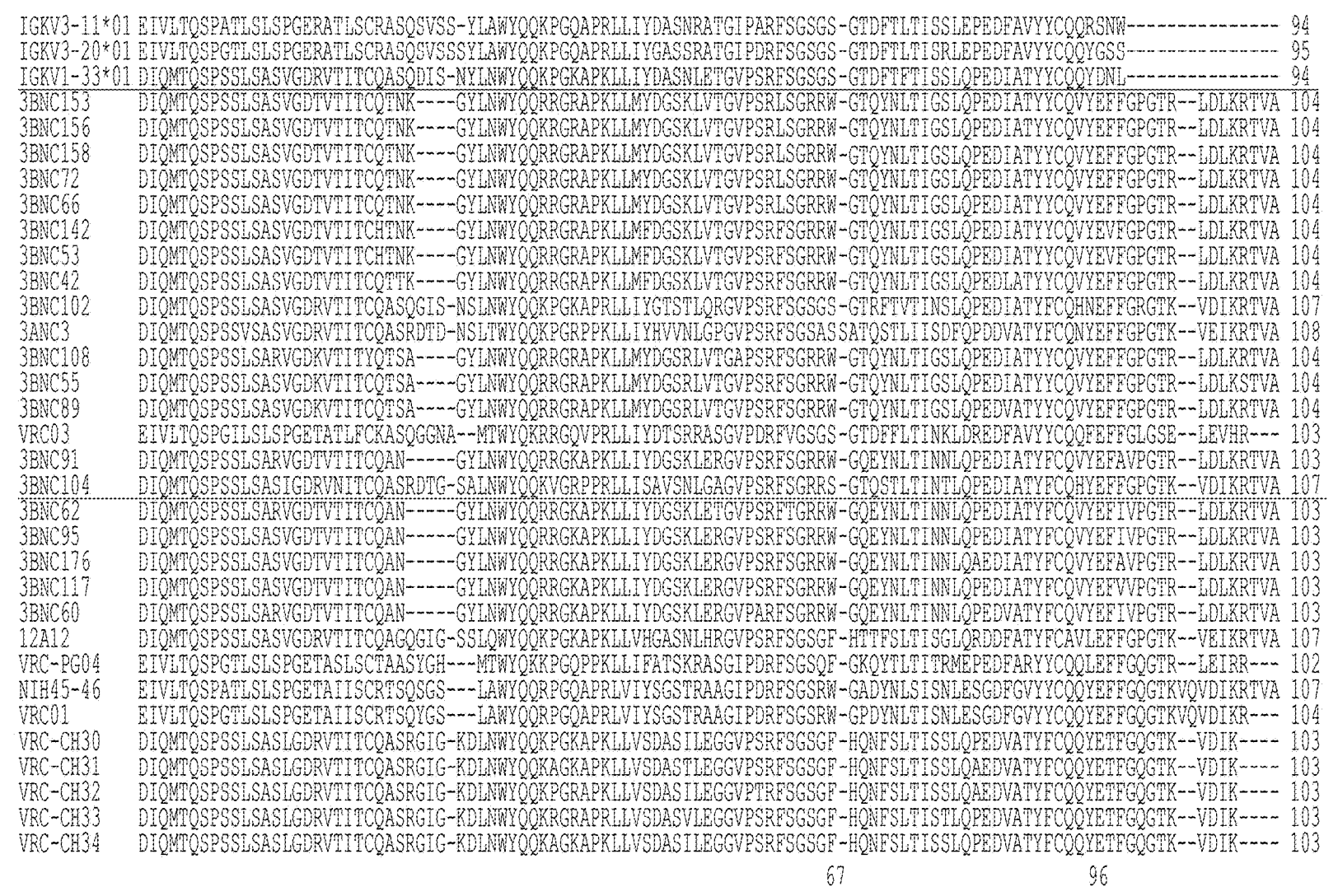

FIG. 20A shows an alignment of the heavy chains of PVL antibodies, their less potent relatives, and their germ-line precursor (SEQ ID NOs: 2, 6, 8, 10, 12, 14, 16, 18, 20, 22, 24, 26, 28, 30, 32, 34, 36, 38, 40, 45, 46, and 50-62), according to embodiments of the present invention.

FIG. 20B shows an alignment of the light chains of PVL antibodies, their less potent relatives, and their germ-line precursors (SEQ ID NOs: 1, 5, 7, 9, 11, 13, 15, 17, 19, 21, 23, 25, 27, 29, 31, 33, 35, 37, 39, and 63-76), according to embodiments of the present invention.

DETAILED DESCRIPTION

Structure-based design was previously used to create the NIH45-46$^{G54W}$ antibody, a single amino acid change from the NIH45-46 antibody, which was previously the single most potent and broadly neutralizing anti-HIV-1 antibody described to date as disclosed in US Patent Publication 2012/0288502 to Diskin et al., 2010, *Nature structural & molecular biology* 17:608-613; Diskin et al., 2011, *Science* 334:1289-1293; Nakamura et al., 2013, *AIDS* 27:337-346; and Sather et al., 2012, *J Virol* 86:12676-12685 the entire contents of all of which are herein incorporated by reference). The NIH45-46$^{G54W}$ antibody belongs to the PVL (Potent VRC01-Like) family of antibodies that target the CD4bs on the HIV-1 trimeric spike complex. The NIH45-46$^{G54W}$ antibody was further substituted in the light chain with a tyrosine (Y) replacing the serine(S) at position 28. The resulting double substituted (i.e., "double mutant") antibody is referred to as NIH45-46$^{G54W(HC)S28Y(LC)}$ or as 45-46m2. This 45-46m2 antibody showed improved potency over NIH45-46$^{G54W}$ as disclosed in U.S. patent application Ser. No. 13/714,398, the entire contents of which are herein incorporated by reference.

Figure 11:
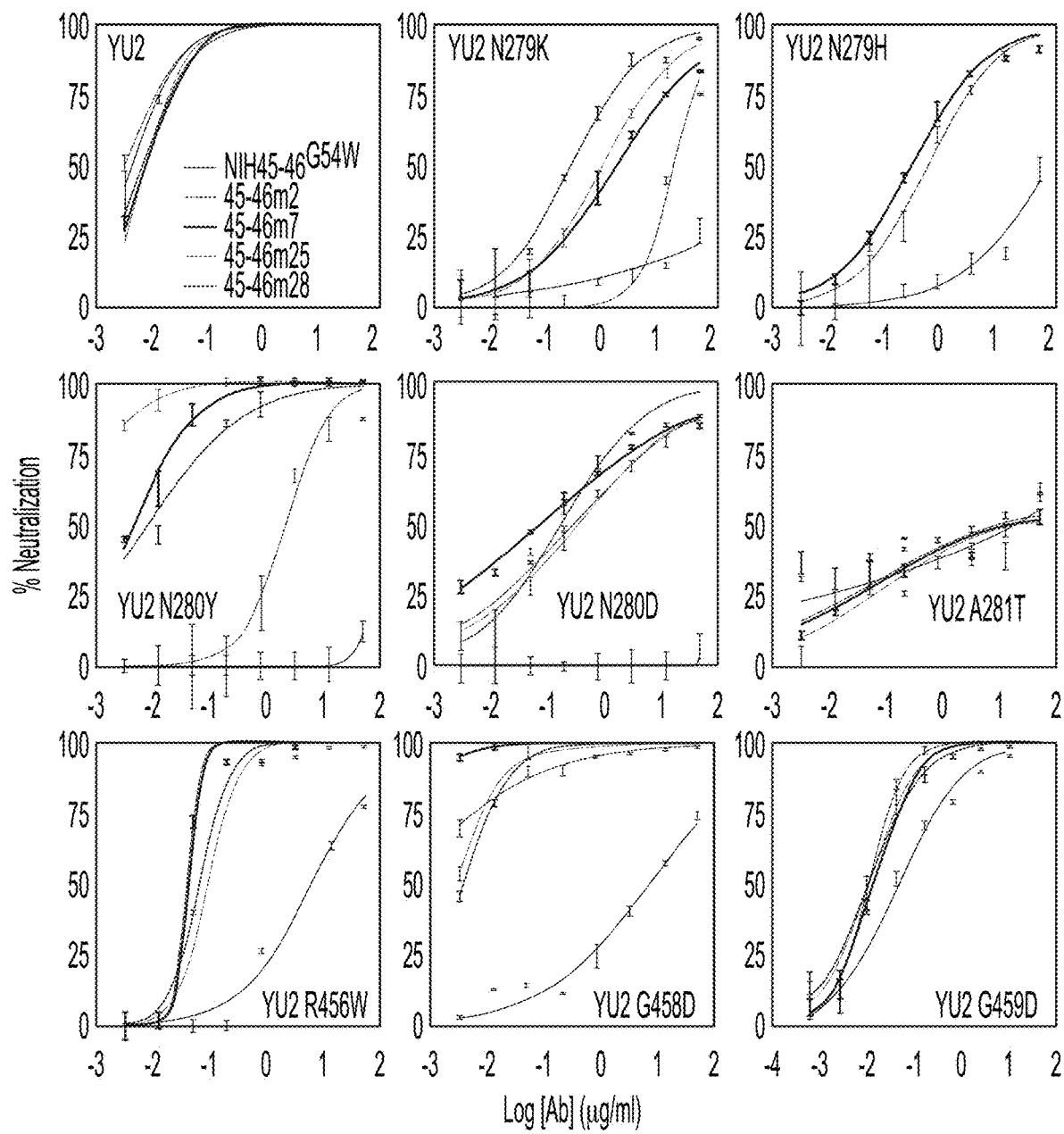
FIG. 11 shows neutralization curves for selected YU-2 mutant strains, as indicated, where the error bars represent standard deviation from the mean, according to embodiments of the present invention.

Nonetheless, a small group of HIV-1 clones are naturally resistant to neutralization by NIH45-46$^{G54W}$ (Diskin et al., 2011, *Science* 334:1289-1293, the entire contents of which are herein incorporated by reference) and escape mutants emerge during exposure to NIH45-46$^{G54W}$ (Klein et al., 2012 *Nature* 492:118-122, the entire contents of which are herein incorporated by reference). By replacing the highly conserved Trp47 residue (a germline residue) in the NIH45-46m2 (HC) antibody with different smaller amino acids, antibodies were identified that are capable of neutralizing strains YU-2$^{N279K}$, YU-2$^{N280D}$, and YU-2$^{N280Y}$ (FIGS. 10, 11). Specifically, the "triple" mutants, 45-46m7 (45-46m2+ HC W47V), 45-46m25 (45-46m2+HC W47I), and 45-46m28 (45-46m2+HC W47T), effectively neutralized all YU-2 mutants with the exception of YU-2A28IT, which included a newly introduced potential N-linked glycosylation site at Asn279$_{gp120}$.

In some embodiments, an antibody composition includes one of the triple mutants (45-46m7, 45-46m25, 45-46m28) combined with 45-46m2. In some embodiments, an antibody composition includes one of the triple mutants (45-46m7, 45-46m25, 45-46m28) combined with 45-46m2 and the PG9 antibody or the 10-1074 antibody, as described herein.

Abbreviations for amino acids are used throughout this disclosure and follow the standard nomenclature known in the art. For example, as would be understood by those of ordinary skill in the art, Alanine is Ala or A; Arginine is Arg or R; Asparagine is Asn or N; Aspartic Acid is Asp or D; Cysteine is Cys or C; Glutamic acid is Glu or E; Glutamine is Gln or Q; Glycine is Gly or G; Histidine is His or H; Isoleucine is Ile or I; Leucine is Leu or L; Lysine is Lys or K; Methionine is Met or M; Phenylalanine is Phe or F; Proline is Pro or P; Serine is Ser or S; Threonine is Thr or T; Tryptophan is Trp or W; Tyrosine is Tyr or Y; and Valine is Val or V.

Hydrophobic amino acids are well known in the art. Hydrophobic amino acids include alanine, isoleucine, leucine, methionine, phenylalanine, tryptophan, tyrosine, and valine. In some embodiments of the present invention, an anti-CD4bs PVL antibody has a hydrophobic amino acid substituted at a position equivalent to Phe43 of the CD4 receptor protein, wherein the hydrophobic amino acid is alanine, isoleucine, leucine, methionine, phenylalanine, tryptophan, tyrosine, or valine. In other embodiments, an anti-CD4bs PVL antibody has a hydrophobic amino acid substituted at the position equivalent to Phe43 of CD4 receptor protein, wherein the hydrophobic amino acid is tryptophan, phenylalanine, or tyrosine.

In addition to the hydrophobic acids, other amino acids that may be substituted at the Phe43-equivalent position of CD4 in the heavy chain of a PVL antibody, include glycine, histidine, arginine, glutamine, asparagine, glutamic acid, aspartic acid, lysine, and serine.

Throughout this disclosure and in embodiments of the present invention, the term "antibody" (Ab) as used herein includes monoclonal antibodies, polyclonal antibodies, multispecific antibodies (for example, bispecific antibodies and polyreactive antibodies), and antibody fragments. Thus, the term "antibody" and "isolated antibody" are used interchangeably herein to refer to an isolated antibody according to embodiments of the present invention. An antibody in any context within this specification is meant to include, but is not limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from the NH2 terminus to the COOH terminus as follows: FWR1, CDR1, FWR2, CDR2, FWR3, CDR3, FWR4. The variable regions of the heavy and light chains contain a binding domain that interacts with an antigen while, depending on the isotype, the constant region(s) may mediate the binding of the immunoglobulin to host tissues or factors. CDR1, CDR2, and CDR3 of the light chain are referred to as CDRL1, CDRL2 and CDRL3, respectively. CDR1, CDR2, CDR3 of the heavy chain are referred to as CDRH1, CDRH2, and CDRH3, respectively.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan. The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in close proximity by the FRs and, with the hypervariable regions from the other chain, contribute to the formation of the antigen-binding site of antibodies. The term "hypervariable region" as used herein refers to the amino acid residues of an antibody that are responsible for antigen binding. The hypervariable region generally comprises amino acid residues from a "complementarity determining region" ("CDR").

An antibody of the present invention may be a "humanized antibody". A humanized antibody is considered to be a human antibody that has one or more amino acid residues introduced into it from a source that is non-human. These non-human amino acid residues often are referred to as "import" residues, which typically are taken from an "import" variable region. Humanization may be performed following known methods by substituting import hypervariable region sequences for the corresponding sequences of a human antibody. (See, for example, Jones et al., Nature, 321:522-525 20 (1986); Reichmann et al., Nature, 332:323-327 (1988); Verhoeyen et al., Science, 239:1534-1536 (1988)) the entire contents of all of which are incorporated herein by reference). Accordingly, such "humanized" antibodies are chimeric antibodies in which less than a full intact human variable region has been substituted by the corresponding sequence from a non-human species.

An antibody of the present invention includes an "antibody fragment" which includes a portion of an intact antibody, such as the antigen binding or variable region of the intact antibody. Examples of antibody fragments include, but are not limited to, Fab, Fab', F(ab')2, and Fv fragments; diabodies; linear antibodies; single-chain antibody molecules; and multispecific antibodies formed from antibody fragments. (See, for example, U.S. Pat. No. 5,641,870, the entire content of which is incorporated herein by reference.)

Throughout this disclosure and in embodiments of the present invention, a "potent VRC01-like" ("PVL") antibody of the present invention is an anti-CD4 binding site antibody that has the following conserved heavy chain (HC) and light chain (LC) residues: Arg71HC, Trp50$_{HC}$, Asn58$_{HC}$, Trp100B$_{HC}$, Glu96$_{LC}$, Trp67$_{LC}$/Phe67$_{LC}$, as well as exactly 5 amino acids in CDRL3 domain (using Kabat numbering). (The Kabat numbering system is described in Abhinandan, K. R. and Martin, A. C. R. (2008), "Analysis and improvements to Kabat and structurally correct numbering of antibody variable domains," *Molecular Immunology*, 45:3832-3839, the entire contents of which are herein incorporated by reference.) A PVL antibody of the present invention is any antibody as defined herein, that has the listed PVL features irrespective of the synthesis or derivation of the antibody, irrespective of the other unrestricted domains of the antibody, and irrespective of whether or not other domains of the antibody are present, so long as the antibody has the signature residues and features.

Throughout the disclosure and in embodiments of the present invention, the terms "Phe43-equivalent position" and "Phe43$_{CD4}$ equivalent position" are used interchangeably and refer to an amino acid position within the heavy chain of a PVL antibody that replicates or mimics the binding pocket and interface contributed by Phe43 of the host CD4 receptor when the CD4 receptor protein is complexed with the HIV viral spike protein gp120. As known in the art, assigned amino acid positions of an antibody do not necessarily correspond to the amino acid residue as numbered from the amino-terminus. Following the Kabat antibody residue/position numbering system, the amino acid residue number may be the same as the amino acid position, but is not necessarily so. (See, Abhinandan, K. R. and Martin, A. C. R. (2008) *Molecular Immunology*, 45:3832-3839.) The structure of the antibody peptide determines the position number. The information for determining position number using the Kabat system for each amino acid in a given sequence can be determined using the information found in Abhinandan and Martin, 2008. Using this position numbering system, the Phe43-equivalent position in a PVL antibody heavy chain sequence can be determined, and substituted with a hydrophobic amino acid to create a similar binding pocket as conferred by Phe43 in CD4. Methods for this mutagenesis are well known in the art.

Subsequent heavy chain sequences can be analyzed using the Kabat numbering system to determine the equivalent position to this position 54. Alternatively, the Phe43CD4-equivalent position can also be determined by structural analysis such as x-ray crystallography. Any means of determining the Phe43CD4-equivalent position may be used so long as the Kabat system is followed as applicable.

For example, the Phe43-equivalent position in NIH45-46 is position 54 as determined by x-ray crystallography and shown herein. The native NIH45-46 heavy chain sequence (SEQ ID NO: 6) contains a glycine at position 54 (Gly54). The native 3BNC60 heavy chain sequence (SEQ ID NO: 8) contains a threonine at position 54 (Thr54). As such, these PVL antibodies substituted with a hydrophobic amino acid, glycine, histidine, arginine, glutamine, or asparagine at these Phe-43 equivalent positions mimic the desired contact interface between the CD4 receptor protein and the CD4 binding site of gp 120 (see, e.g., Example 2).

In some embodiments of the present invention, position 54 (Kabat numbering) of the heavy chain of a PVL antibody has a substituted hydrophobic amino acid. Position 54 is determined by analyzing a heavy chain amino acid sequence of a PVL antibody using the Kabat numbering system.

In some embodiments of the present invention, a hydrophobic amino acid is substituted for the "native" amino acid present at the Phe43CD4-equivalent position on the heavy chain of a PVL antibody, where a PVL antibody is an antibody as defined herein having the PVL signature features as described herein, and "native" refers to the amino acid that is present in the PVL antibody prior to substitution. The native amino acid in the heavy chain may also be hydrophobic, and may be substituted with another hydrophobic amino acid, or with glycine, histidine, arginine, glutamine, asparagine, lysine, glutamic acid, or aspartic acid.

In some embodiments of the present invention, non-limiting examples of PVL antibodies include VRC01, VRC02, NIH-45-46, 3BNC60, 3BNC117, 3BNC62, 3BNC95, 3BNC176, 12A21, VRC-PG04, VRC-CH30, VRC-CH31, VRC-CH32, VRC-CH33, VRC-CH34, VRC03 heavy chain (HC) with VRC01 light chain (LC), gVRC-H5 (d74)/VRC-PG04LC, and gVRC-H12 (d74)/VRC-PG04LC, VRC03, VRC01 heavy chain (HC) with VRC03 light chain (LC), 3BNC55, 3BNC91, 3BNC104, 3BNC89, 12A21, and VRC-PG04b as listed below in Table 1.

TABLE 1

Examples of PVL Antibodies

| Antibody Name | Light Chain SEQ ID NO: | Heavy Chain SEQ ID NO: |
|---|---|---|
| VRC01 | 1 | 2 |
| VRC02 | 3 | 4 |
| NIH-45-46 | 5 | 6 |
| 3BNC60 | 7 | 8 |
| 3BNC117 | 9 | 10 |
| 3BNC62 | 11 | 12 |
| 3BNC95 | 13 | 14 |
| 3BNC176 | 15 | 16 |
| 12A12 | 17 | 18 |
| VRC-PG04 | 19 | 20 |
| VRC-CH30 | 21 | 22 |
| VRC-CH31 | 23 | 24 |
| VRC-CH32 | 25 | 26 |
| VRC-CH33 | 27 | 28 |
| VRC-CH34 | 29 | 30 |
| VRC03 | 31 | 32 |
| 3BNC55 | 33 | 34 |
| 3BNC91 | 35 | 36 |
| 3BNC104 | 37 | 38 |
| 3BNC89 | 39 | 40 |
| 12A21 | 41 | 42 |
| VRC-PG04b | 43 | 44 |
| VRC03HC- VRC01LC | 1 | 32 |
| VRC01HC/VRC03LC | 31 | 2 |
| gVRC-H5(d74)/ VRC-PG04LC | 19 | 45 |
| gVRC0H12(D74)/ VRC-PG04LC | 19 | 46 |

In some embodiments of the present invention, a PVL antibody has a heavy chain selected from one of the heavy chains listed above in Table 1 (SEQ ID NOs 2, 4, 6, 8, 10, 12, 14, 16, 18, 20, 22, 24, 26, 28, 30, 32, 34, 36, 38, 40, 42, 44, 45, and 46). Any PVL heavy chain may be matched with a PVL light chain so long as the signature PVL residue features are maintained. In some embodiments, any one of the PVL heavy chains of Table 1 is expressed with any one of the PVL light chains of SEQ ID NOs 1, 3, 5, 7, 9, 11, 13, 15, 17, 19, 21, 23, 25, 27, 29, 31, 33, 35, 37, 39, 41, and 43. In other embodiments, any PVL antibody heavy chain can be combined with any PVL antibody light chain.

In embodiments of the present invention, the terms "nucleic acid" and "polynucleotide" are used interchangeably herein to refer to single-stranded or double-stranded RNA, DNA, or mixed polymers. Polynucleotides can include genomic sequences, extra-genomic and plasmid sequences, and smaller engineered gene segments that express, or can be adapted to express polypeptides.

An "isolated nucleic acid" is a nucleic acid that is substantially separated from other genome DNA sequences as well as proteins or complexes such as ribosomes and polymerases, which naturally accompany a native sequence.

In some embodiments of the present invention, nucleic acid molecules encode part or all of the light and heavy chains of the described inventive antibodies, and fragments thereof. Due to redundancy of the genetic code, variants of these sequences will exist that encode the same amino acid sequences.

The present invention also includes isolated nucleic acid molecules encoding the polypeptides of the heavy and the light chain of the PVL antibodies listed in Table 1. In some embodiments, an isolated nucleic acid molecule encodes for any of the PVL heavy chain and light chain polypeptides including those of SEQ ID NOs 2, 4, 6, 8, 10, 12, 14, 16, 18, 20, 22, 24, 26, 28, 30, 32, 34, 36, 38, 40, 42, 44, 45, and 46, and SEQ ID NOs 1, 3, 5, 7, 9, 11, 13, 15, 17, 19, 21, 23, 25, 27, 29, 31, 33, 35, 37, 39, 41, and 43, respectively, in which the Phe43CD4-equivalent amino acid (i.e., the target amino acid) of the heavy chain is substituted with a hydrophobic amino acid.

Embodiments of the present invention also include vectors and host cells including a nucleic acid encoding a PVL antibody of the present invention, as well as recombinant techniques for the production of polypeptide of the invention. Vectors of the invention include those capable of replication in any type of cell or organism, including, for example, plasmids, phage, cosmids, and mini chromosomes. In some embodiments, vectors comprising a polynucleotide 5 of the described invention are vectors suitable for propagation or replication of the polynucleotide, or vectors suitable for expressing a polypeptide of the described invention. Such vectors are known in the art and commercially available.

In embodiments of the present invention, "vector" includes shuttle and expression vectors. Typically, the plasmid construct will include an origin of replication (for example, the ColE1 origin of replication) and a selectable marker (for example, ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells.

In some embodiments of the present invention, in order to express a polypeptide of the invention, the nucleotide sequences encoding the polypeptide, or functional equivalents, may be inserted into an appropriate expression vector, i.e., a vector that contains the necessary elements for the transcription and translation of the inserted coding sequence. Methods well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (2001) Molecular Cloning, A Laboratory Manual, Cold Spring Harbor Press, Plainview, N.Y., the entire contents of which are incorporated herein by reference.

As used herein, the term "cell" can be any cell, including, but not limited to, eukaryotic cells, such as, but not limited to, mammalian cells or human cells.

In some embodiments of the present invention, the antibodies disclosed herein are produced recombinantly using vectors and methods available in the art. (See, e.g. Sambrook et al., 2001, supra). Human antibodies also can be generated by in vitro activated B cells. (See, for example, U.S. Pat. Nos. 5,567,610 and 5,229,275, the entire contents of both of which are herein incorporated by reference.) Reagents, cloning vectors, and kits for genetic manipulation are available from commercial vendors such as BioRad, Stratagene, Invitrogen, ClonTech and Sigma-Aldrich Co.

In some embodiments of the present invention, human antibodies are produced in transgenic animals (for example, mice) that are capable of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germline mutant mice results in the production of human antibodies upon antigen challenge. See, for example, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669; 5,545,807; and WO 97/17852, the entire contents of all of which are herein incorporated by reference. Such animals can be genetically engineered to produce human antibodies comprising a polypeptide of a PVL antibody according to embodiments of the present invention.

In some embodiments of the present invention, a method includes the preparation and administration of an HIV antibody composition (e.g., a PVL antibody having a hydrophobic amino acid substituted at the Phe43CD4-equivalent position of the PVL heavy chain) that is suitable for administration to a human or non-human primate patient having an HIV infection, or at risk of HIV infection, in an amount and according to a schedule sufficient to induce a protective immune response against HIV, or reduction of the HIV virus, in a human.

In some embodiments of the present invention, a vaccine includes at least one antibody as disclosed herein and a pharmaceutically acceptable carrier. In some embodiments of the present invention, the vaccine is a vaccine including at least one PVL antibody as described herein and a pharmaceutically acceptable carrier. The vaccine can include a plurality of the antibodies having the characteristics described herein in any combination and can further include HIV neutralizing antibodies such as a PVL antibody having the $Phe43_{CD4}$-equivalent residue on the heavy chain substituted with a hydrophobic amino acid.

In some embodiments of the present invention, carriers as used herein include pharmaceutically acceptable carriers, excipients or stabilizers that are nontoxic to a cell or mammal being exposed thereto at the dosages and concentrations employed. Often the physiologically acceptable carrier is an aqueous pH buffered solution. Examples of physiologically acceptable carriers include, but are not limited to, buffers such as phosphate, citrate, and other organic acids; antioxidants including, but not limited to, ascorbic acid; low molecular weight (less than about 10 residues) polypeptides; proteins, such as, but not limited to, serum albumin, gelatin, or immunoglobulins; hydrophilic polymers such as, but not limited to polyvinylpyrrolidone; amino acids such as, but not limited to glycine, glutamine, asparagine, arginine or lysine; monosaccharides, disaccharides, and other carbohydrates including, but not limited to glucose, mannose, or dextrins; chelating agents such as, but not limited to EDTA (ethylenediaminetetraacetic acid); sugar alcohols such as, but not limited to mannitol or sorbitol; salt-forming counterions such as, but not limited to sodium; and/or nonionic surfactants such as, but not limited to TWEEN® (polysorbate); polyethylene glycol (PEG), and PLURONICS® (poloxamers).

In some embodiments of the present invention, the compositions may include a single antibody or a combination of antibodies, which can be the same or different, in order to prophylactically or therapeutically treat the progression of various subtypes of HIV infection after vaccination. Such combinations can be selected according to the desired immunity. When an antibody is administered to an animal or a human, it can be combined with one or more pharmaceutically acceptable carriers, excipients or adjuvants as are known to one of ordinary skill in the art. The composition can further include broadly neutralizing antibodies known in the art, including, for example, a PVL antibody having the Phe43$_{CD4}$-equivalent residue substituted with a hydrophobic amino acid or glycine, histidine, arginine, glutamine, asparagine, lysine, glutamic acid, or aspartic acid, and the serine at position 28 of the light chain substituted with tyrosine (S28Y LC).

In some embodiments of the present invention, an antibody-based pharmaceutical composition includes a therapeutically effective amount of an isolated HIV antibody which provides a prophylactic or therapeutic treatment choice to reduce infection of the HIV virus. The antibody-based pharmaceutical composition according to embodiments of the present invention may be formulated by any number of strategies known in the art (e.g., see McGoff and Scher, 2000, Solution Formulation of Proteins/Peptides: In McNally, E. J., ed. Protein Formulation and Delivery. New York, N.Y.: Marcel Dekker; pp. 139-158; Akers and Defilippis, 2000, Peptides and Proteins as Parenteral Solutions. In: Pharmaceutical Formulation Development of Peptides and Proteins. Philadelphia, Pa.: Taylor and Francis; pp. 145-177; Akers, et al., 2002, Pharm. Biotechnol. 14:47-127, the entire contents of all of which are incorporated herein by reference).

In some embodiments of the present invention, a method for treating a mammal infected with a virus infection, such as, for example, HIV, includes administering to said mammal a pharmaceutical composition including an HIV antibody composition according to an embodiment disclosed herein. According to some embodiments, the method for treating a mammal infected with HIV includes administering to said mammal a pharmaceutical composition that includes an antibody according to an embodiment disclosed herein, or a fragment thereof. The compositions of embodiments of the present invention may include more than one antibody having the characteristics disclosed herein (for example, a plurality or pool of PVL antibodies, each antibody having the Phe43CD4-equivalent residue substituted with a hydrophobic amino acid).

In some embodiments of the present invention, in vivo treatment of human and non-human patients includes administering or providing a pharmaceutical formulation including an HIV antibody according to embodiments of the present invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies can be administered parenterally, when possible, at the target cell site, or intravenously. In some embodiments, a PVL antibody composition according to embodiments as described herein is administered by intravenous or subcutaneous administration.

In some embodiments of the present invention, a therapeutically effective amount of an antibody is administered to a patient. In some embodiments, the amount of antibody administered is in the range of about 0.1 mg/kg to about 50 mg/kg of patient body weight. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

In some embodiments of the present invention, passive immunization using a PVL antibody according to embodiments as disclosed herein, is used as an effective and safe strategy for the prevention and treatment of HIV disease. (See, for example, Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), the entire contents of all of which are herein incorporated by reference).

The following Examples are presented for illustrative purposes only, and do not limit the scope or content of the present application.

EXAMPLES

Reference is made to Diskin et al. 2013, JEM, 210:1235-1249; Diskin et al., 2011, Science, 334:12989-1293; and West et al., 2012, PNAS, (doi: 10.1073/pnas. 1208984109), the entire contents of all of which are incorporated herein by reference. FIGS. 20A and 20B show the heavy chain (SEQ ID NOs. 2, 6, 8, 10, 12, 14, 16, 18, 20, 22, 24, 26, 28, 30, 32, 34, 36, 38, 40, 45, 46, and 50-62) and light chain (SEQ ID NOs. 1, 5, 7, 9, 11, 13, 15, 17, 19, 21, 23, 25, 27, 29, 31, 33, 35, 37, 39, and 63-76) amino acid sequence alignments of several related variant groups of PVL antibodies as presented in FIG. 2 of West et al. with CDRs defined using the Chothia definition of the Abysis database.

Example 1. Targeting Emerging Escape Mutants. To further improve the potency of 45-46m2 against escape mutants in general and against non-consensus N/DNGG motifs in particular, 24 antibody mutants were designed to reduce steric clashes between 45-46m2 and substituted residues in the gp 120 N/DNGG motif (FIG. 1). The neutralization potencies of the new mutant antibodies were evaluated against the panel of YU-2 mutants (FIG. 9-10). Modifying critical somatically-mutated residues in PVL antibodies (Trp $102_{45\text{-}46m2(HC)}$, $Tyr100_{45\text{-}46m2(HC)}$ and $Tyr89_{45\text{-}46m2(LC)}$) (West et al., 2012, supra) to create mutants 45-46m4, m5, m6, m16, m17, m18, m20, m21, m22, m23, m29, m30, m31, m32, m34, m35 and m36 did not improve the neutralization profiles of the antibodies (FIG. 9). However, replacing the highly conserved Trp47$_{45\text{-}46m2(HC)}$ (a germline residue) with different smaller amino acids resulted in antibodies capable of neutralizing YU-2$^{N279K}$, YU-2N$^{280D}$, and YU-2$^{N280Y}$ (FIGS. 10-11). These mutants, 45-46m7, 45-46m25, and 45-46m28 (45-46m2+HC mutations W47V, W47I, and W47T, respectively), effectively neutralized all YU-2 mutants with the exception of YU-2A28IT, which included a newly introduced potential N-linked glycosylation site at Asn279$_{gp120}$.

Figures 12C, 12D:
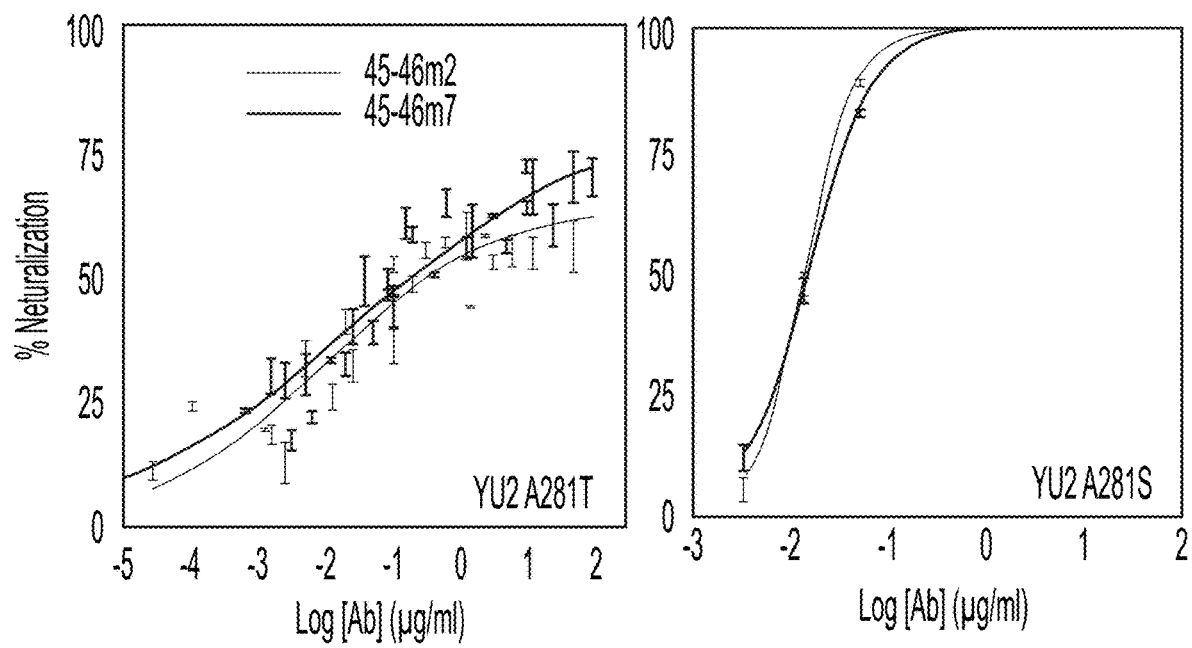
FIG. 12C shows neutralization curves for 45-46m2 and 45-46m7 against YU-2A$^{281T}$ and YU-2$^{4281S}$, in which the curves for YU-2$^{4281T}$ were derived using an extended concentration series, according to embodiments of the present invention.
FIG. 12D is a table of neutralization results of A281T-associated mutations affecting the Asn276$_{gp120}$-linked glycan, according to embodiments of the present invention.

Example 2. Fitness Cost Associated with a Glycan at Asn279$_{gp120}$. To explore the effects of the A281T$_{gp120}$ mutation that abrogated neutralization of the 45-46m antibodies, a previously-described in vitro assay (Sather et al., 2012, *J Virol* 86:12676-12685, the entire contents of which are herein incorporated by reference) was used to compare the relative fitness of YU-2 mutants that either included (YU-2$^{A281T}$) or did not include (YU-2 WT, YU-2$^{N279K}$, and YU-2$^{N280D}$) a potential N-linked glycosylation site (Asn279$_{gp120}$-X-Ser/Thr281$_{gp120}$) (FIG. 12A). Although infectious, YU-2A$^{281T}$ exhibited a disrupted replication profile relative to the other viruses (FIG. 12B), suggesting a fitness cost associated with an Asn279$_{gp120}$-attached glycan. Consistent with this suggestion, only three strains in the Los Alamos Data Base carry a potential N-linked glycosylation site at Asn279$_{gp120}$, all with low predicted glycosylation potentials (FIG. 12A). In addition, unlike the curves for other YU-2 variants, the in vitro neutralization curves for YU-2$^{A281T}$ saturated at about 50%, suggesting the existence of heterogeneous viral populations resulting from incomplete incorporation of N-linked glycan at Asn279$_{gp120}$ (FIG. 11; FIG. 12C).

Available structural information about CD4 binding to gp 120 can be used to rationalize why the viral replication profiles of the YU-2$^{A281T}$ mutant were retarded compared to YU-2 WT (FIG. 12B). The N-linked glycan attached to Asn279$_{gp120}$ that was introduced by the A281T$_{gp120}$ substitution is predicted to exert a fitness cost for HIV-1 by partially blocking the CD4 binding site. Indeed if there was not a fitness cost associated with having a glycan at residue 279, one would not expect the highly correlated amino acid distribution at sites 279 and 281 observed in the Los Alamos database. Specifically, residue 279$_{gp120}$ is usually Asn (51%) or Asp (46%), and this preference is not clade-specific. Residue 281$_{gp120}$ is Thr in about 11% (n=314) of the sequences. However, Thr (T) occurs in only one strain (CH080183_e_p1) that includes Asn at 279$_{gp120}$, a distribution that has less than a 1 in 10$^{100}$ chance of occurring randomly (Fisher Exact test). Furthermore the middle residue of the potential N-linked glycosylation sequence in this strain is proline, which would prevent attachment of an N-glycan to Asn279$_{gp120}$. Additionally, of the 39 strains with Ser281$_{gp120}$, only three have Asn279$_{gp120}$ (CY122, 99CMA121, U14842). An analysis of the glycosylation potential of these three strains (FIG. 12A) using the NetNGlyc 1.0 Server indicates no glycosylation potential (strains CY122 and U14842) or a very low potential (strain 99CMA121) for Asn279$_{gp120}$. The YU-2$^{A281S}$ mutant has a higher glycosylation potential at Asn279$_{gp120}$ compared with the 99CMA121 strain (0.5402 vs. 0.5188; FIG. 12A) but unlike YU-2$^{A281T}$, the YU-2$^{A281S}$ mutant was neutralized well (FIG. 12C), suggesting that an N-glycan was not incorporated at Asn279$_{gp120}$ despite the N-X-S motif.

Figure 2:
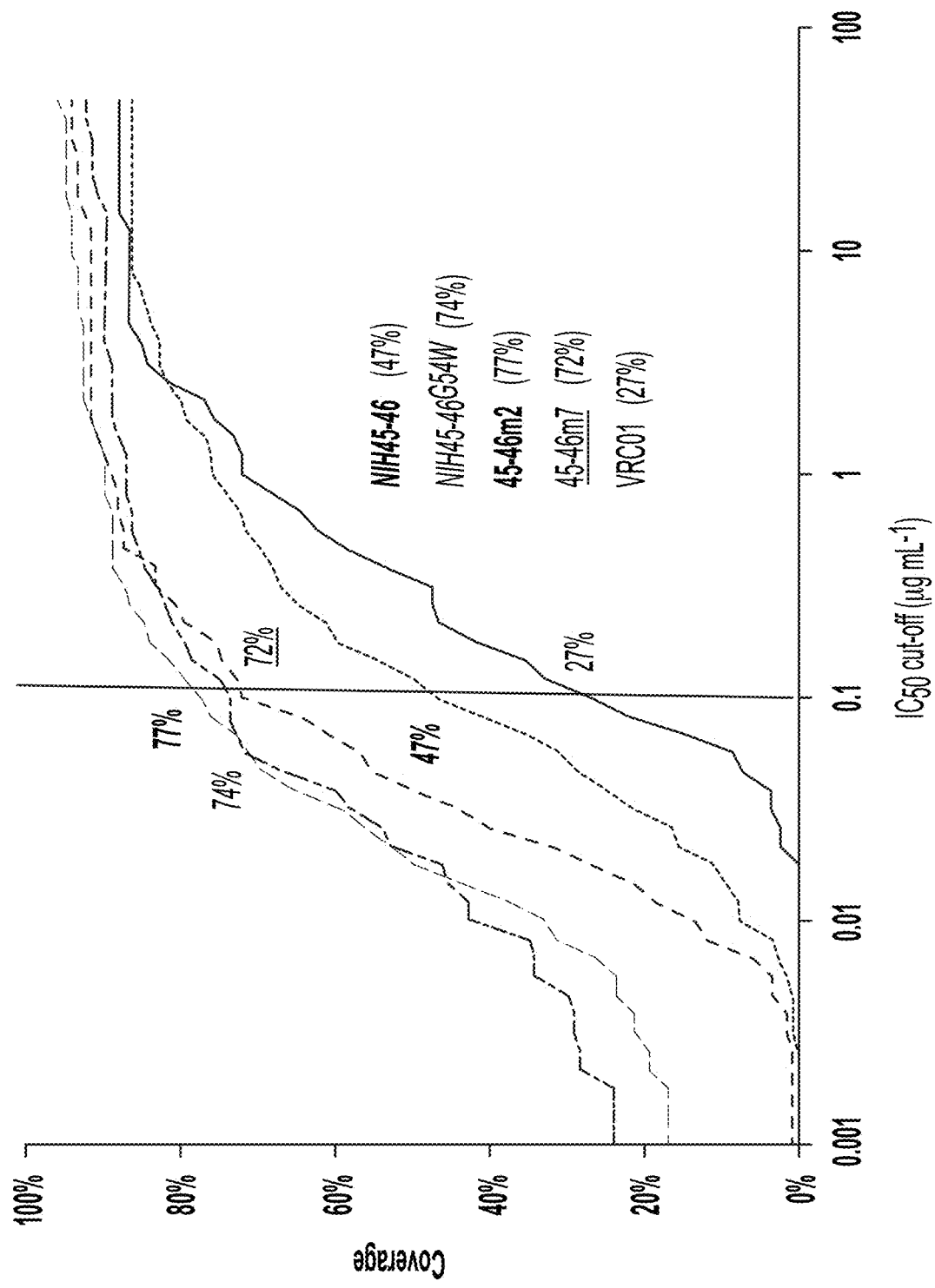
FIG. 2 is a graph of coverage curves showing the cumulative frequency of $IC_{50}$ values up to the concentration shown on the x-axis (plot of the percent of viral strains (y axis) from a panel of 118 HIV strains that were neutralized by NIH45-46, NIH45-46$^{G54W}$, 45-46m2, 46-46m7, and VRC01 at a given IC50 cut-off (x axis)); a vertical line at 0.1 μg/ml designates a theoretical desired potency for a therapeutic reagent, according to embodiments of the present invention.
Figure 4A:
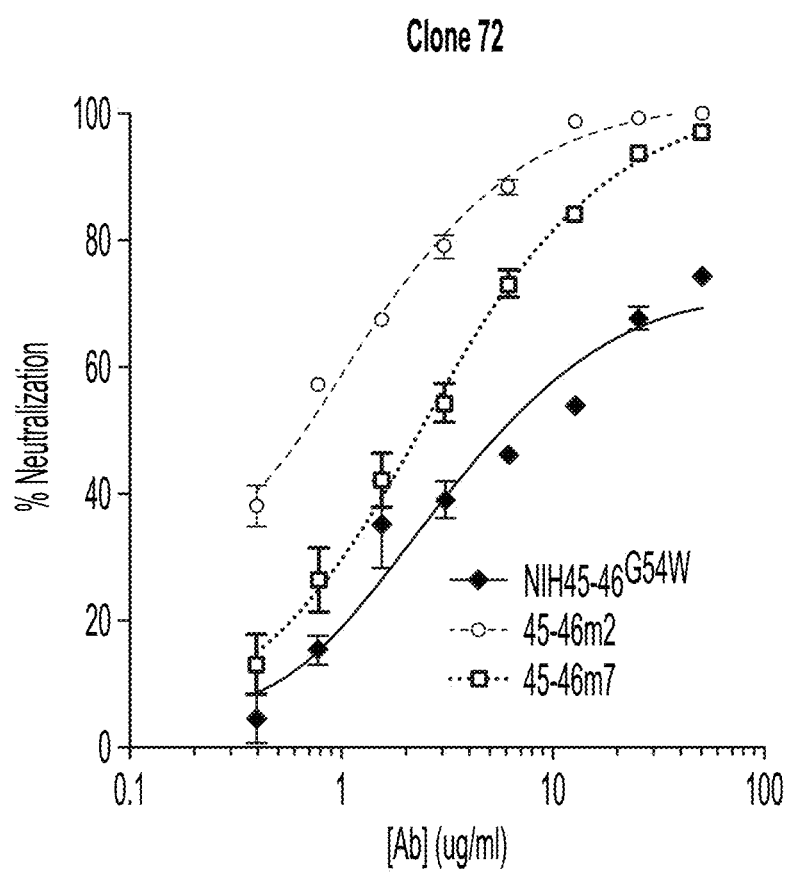
FIGS. 4A-4J are neutralization curves for NIH45-46$^{G54W}$, 45-46m2, and 45-46m7 against 10 viral clones (Clones 72, 113, 205, 01, 02, 03, 05, 06, 08, and 04 in FIGS. 4A-4J, respectively) from patient VC10042 that were isolated 19 years (first three panels) or 22 years (remaining panels) post infection, according to embodiments of the present invention.
Figure 4B:
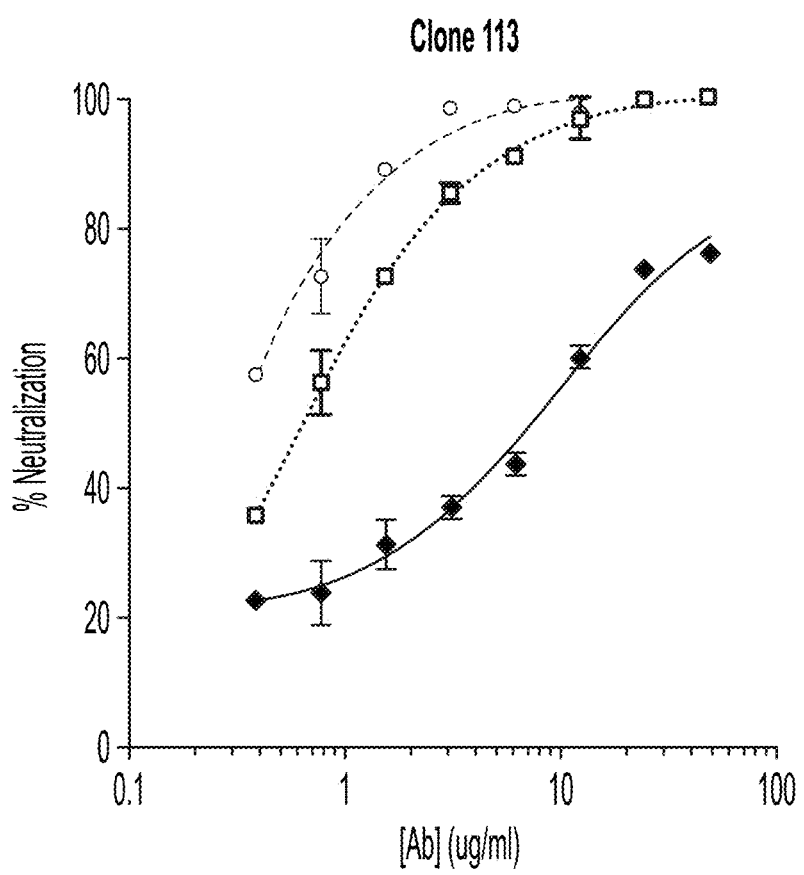
Figure 4C:
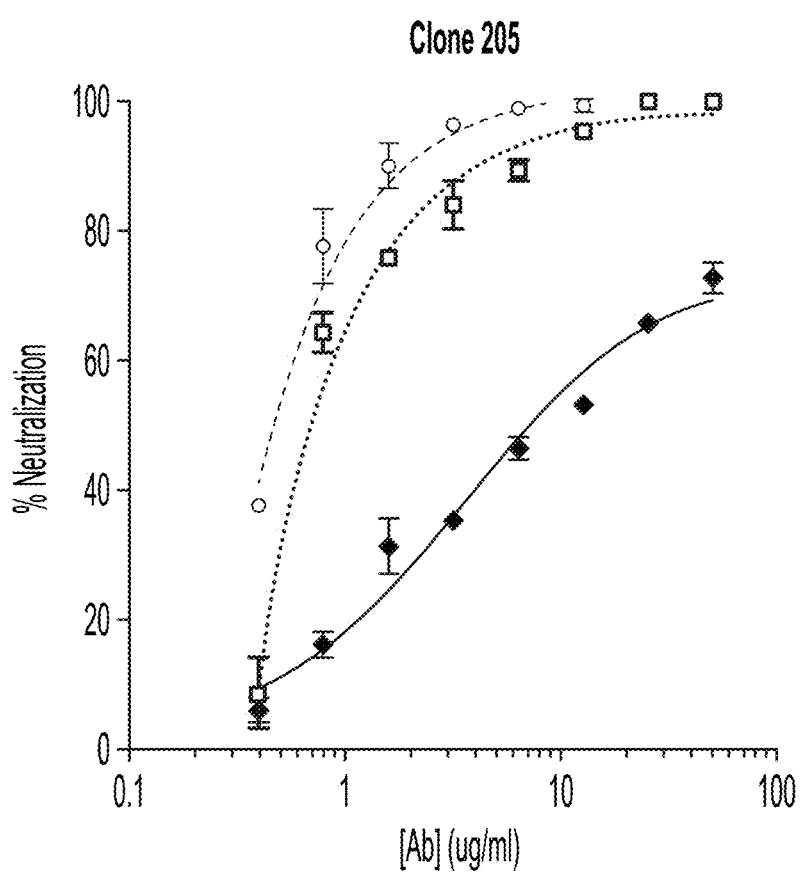
Figure 4D:
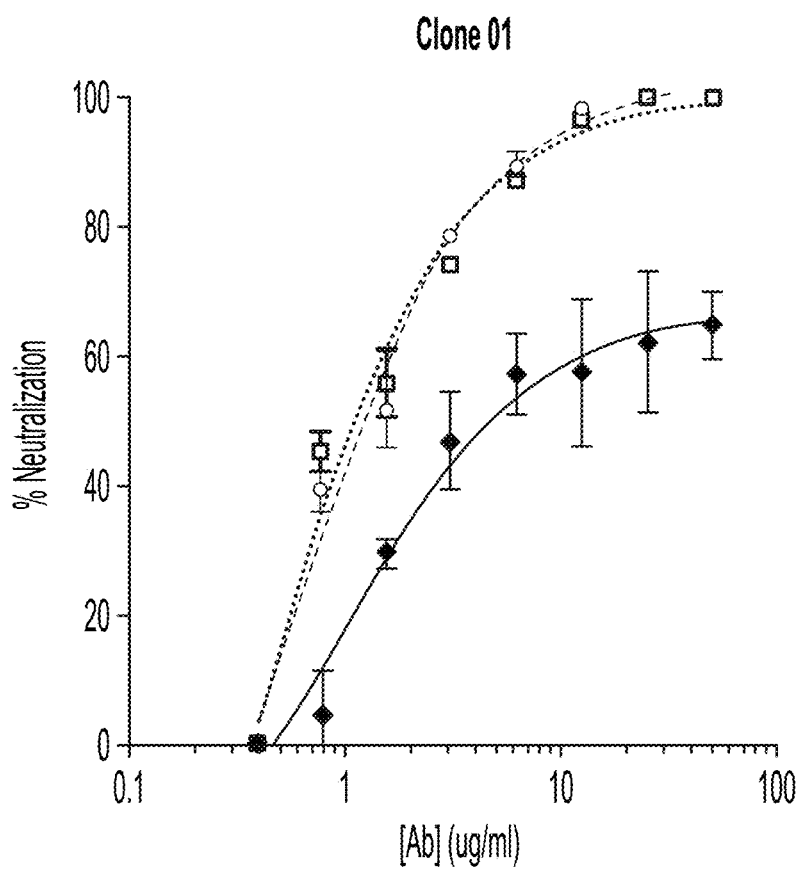
Figure 4E:
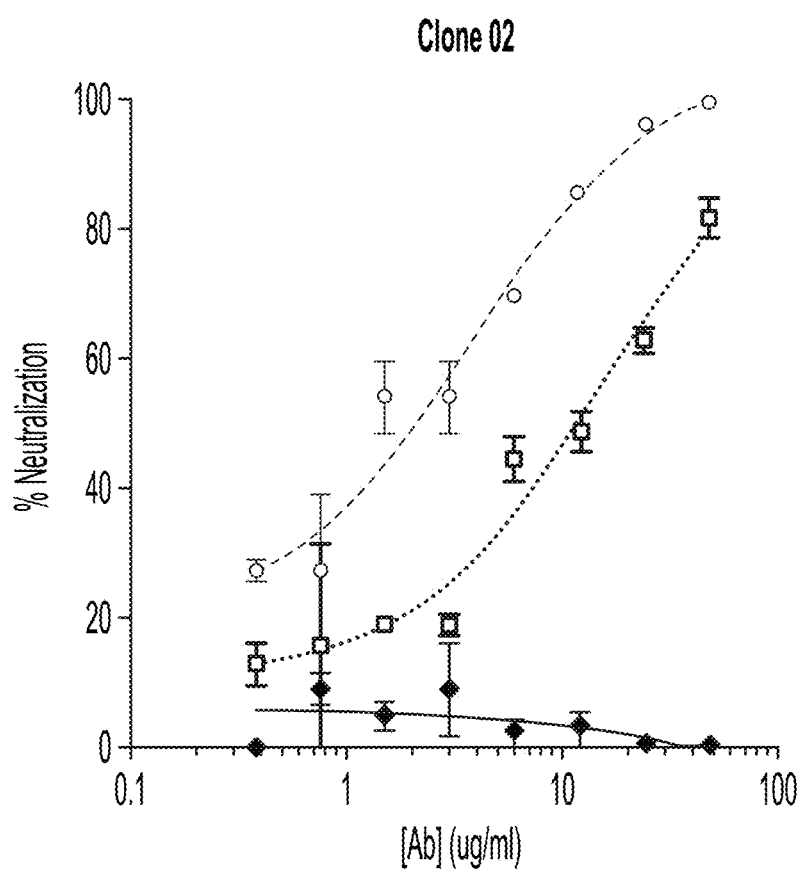
Figure 4F:
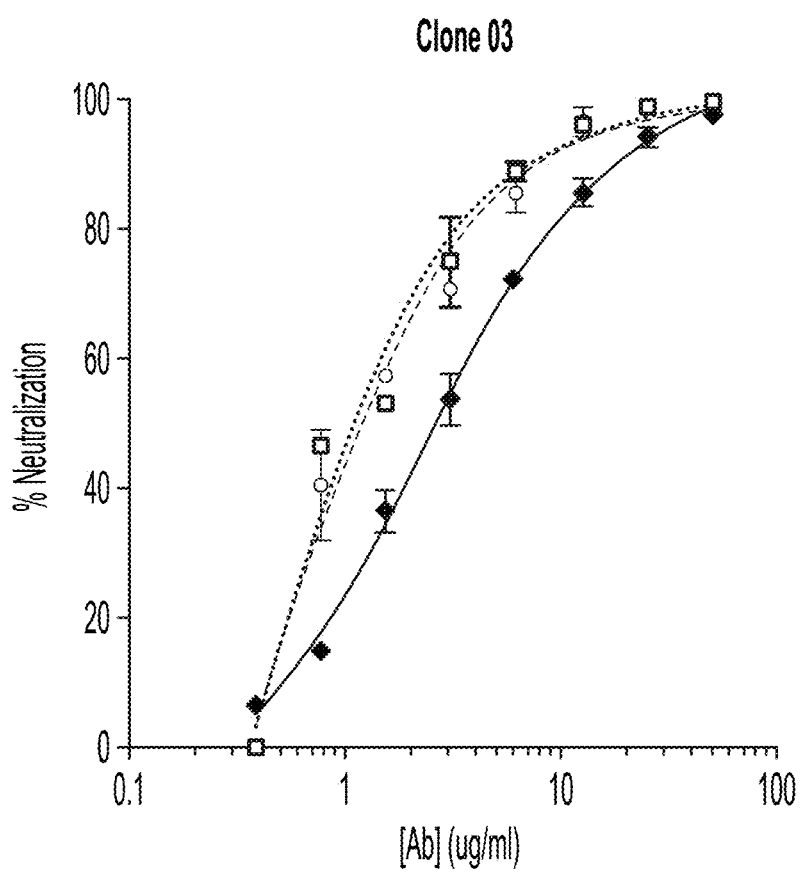
Figure 4G:
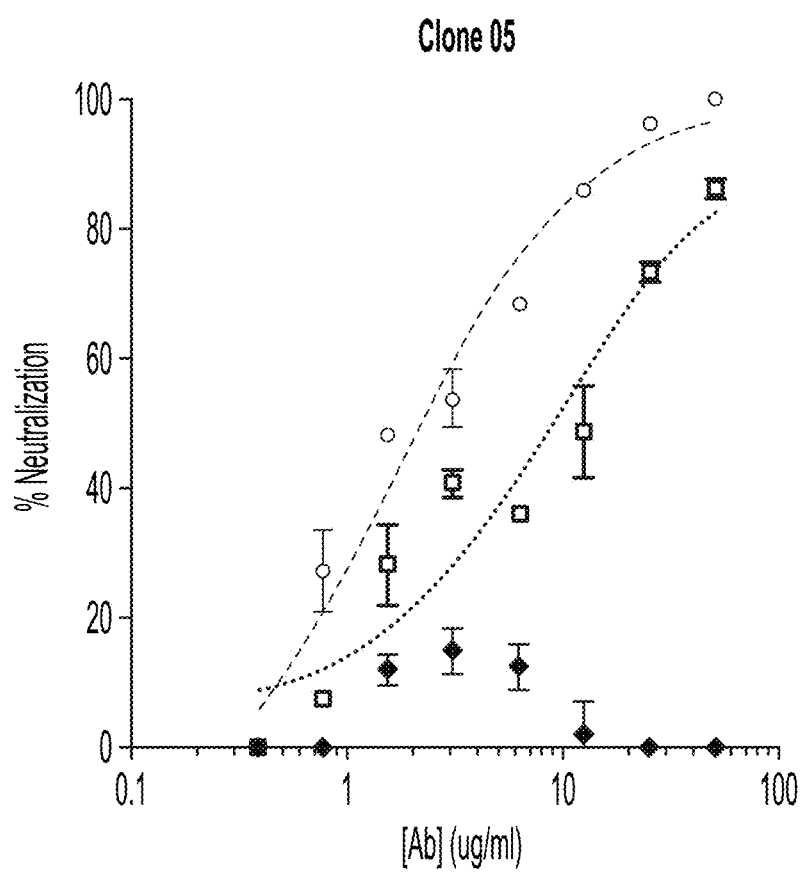
Figure 4H:
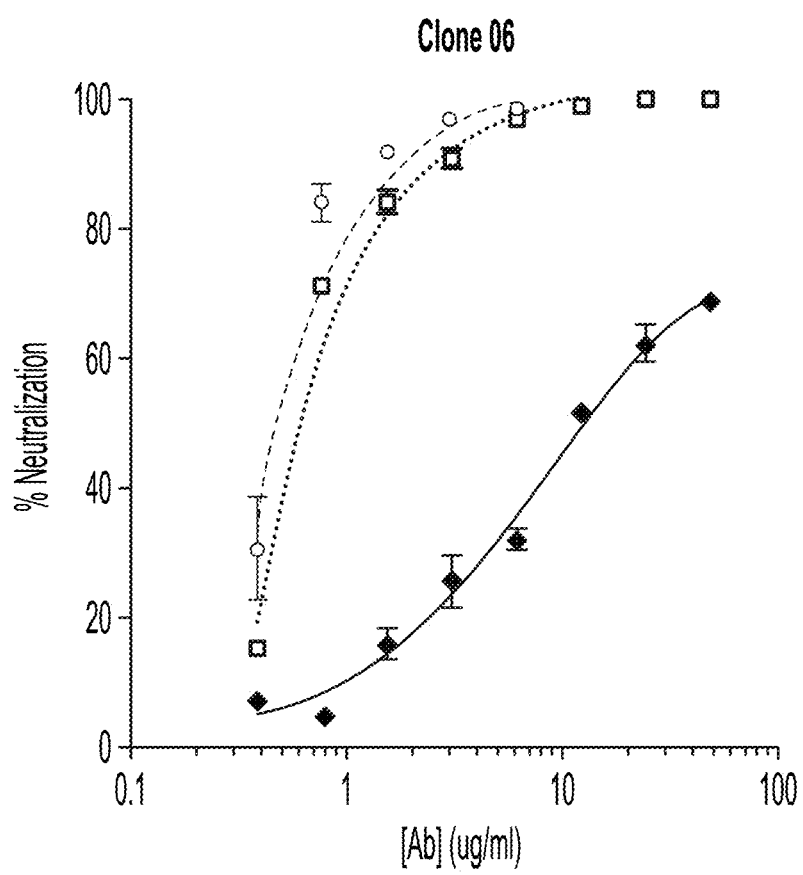
Figure 4I:
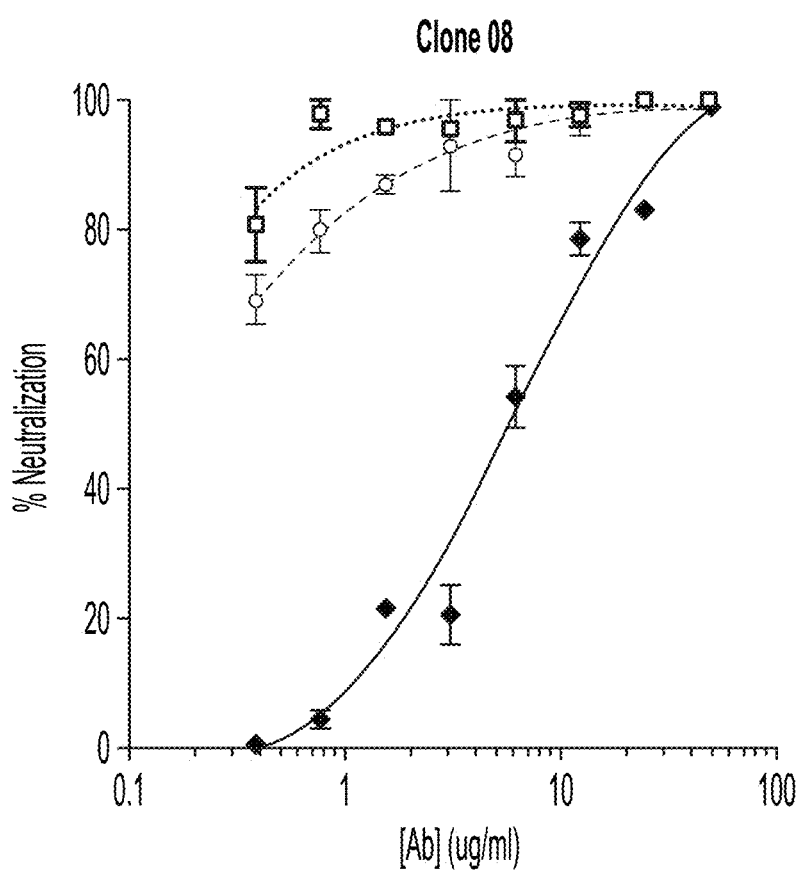
Figure 4J:
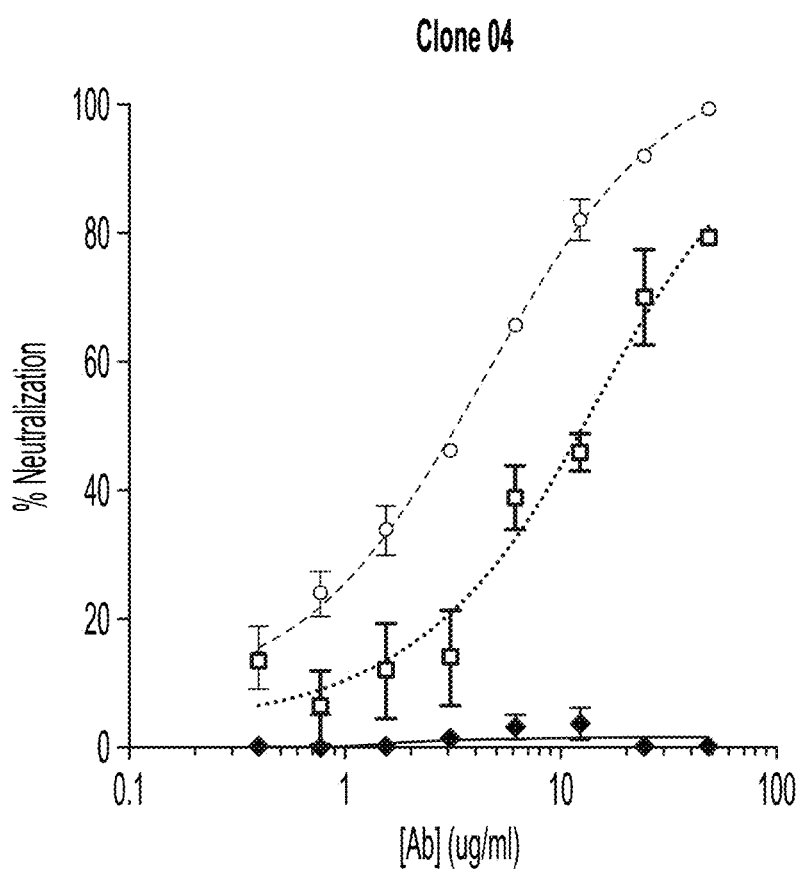
Figure 5A:
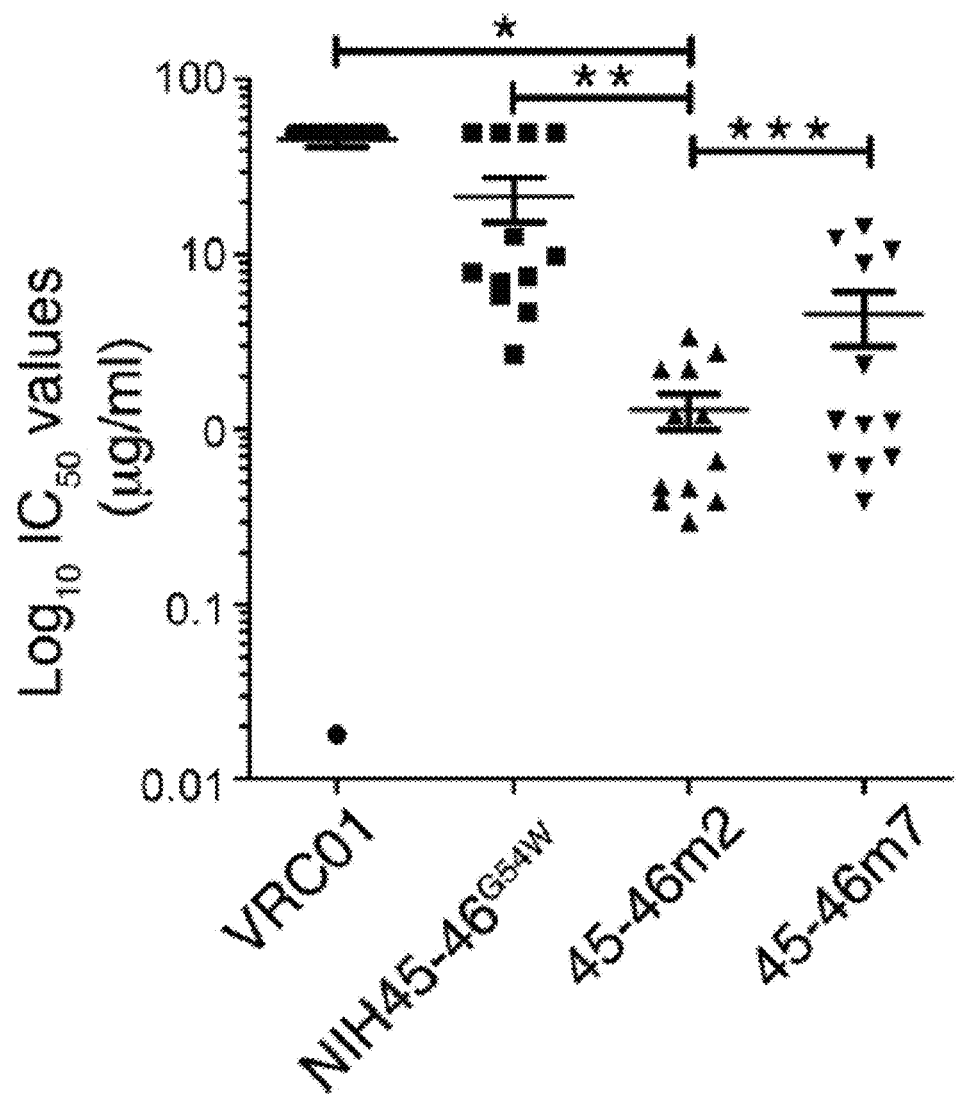
FIG. 5A is a scatter plot comparing IC50 values (μg/ml) for VRC01, NIH45-46$^{G54W}$, 45-46m2 and 45-46m7 against viral clones from patient VC10042, according to embodiments of the present invention.
Figure 6A:
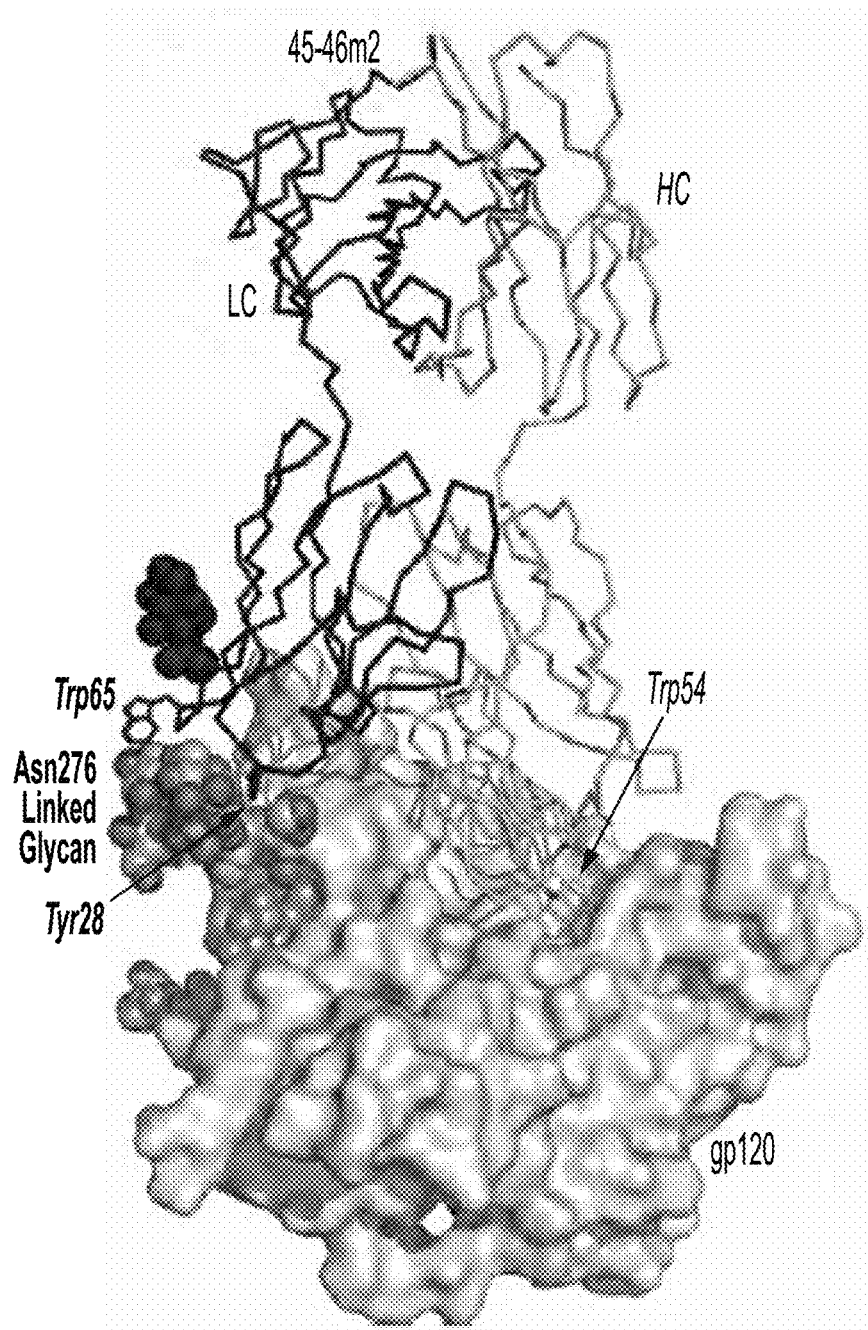
FIG. 6A is a schematic of the 45-46m2/gp 120 structure with gp 120 as a gray surface and 45-46m2 Fab in cyan (HC) and blue (LC) Cα traces, with ordered N-glycans shown in van der Waals representation, with the Asn276$_{gp120}$-linked N-glycan highlighted in shades of red, and Tyr28$_{45-46m2(LC)}$ and TrP54$_{45-46m2(HC)}$ are pointed with arrows, according to embodiments of the present invention.
Figure 6B:
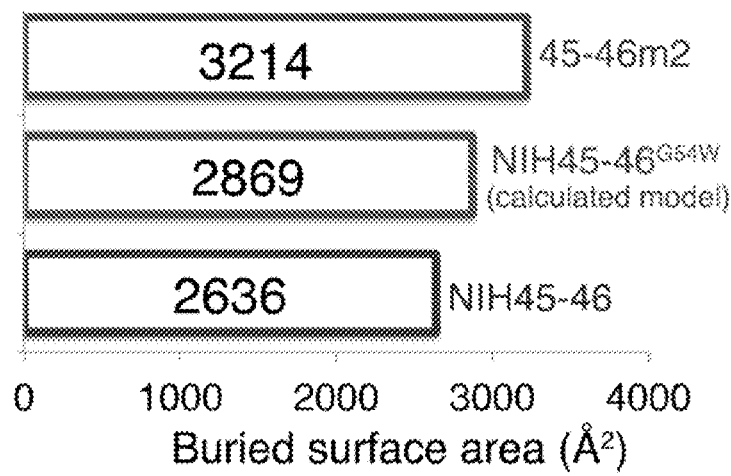
FIG. 6B is a graphical representation of the buried surface areas between gp120 and the indicated antibodies, in which the buried surface area for NIH45-46$^{G54W}$ was calculated by adding the contribution of Trp54 (derived from the structure of 45-46m2/gp120) to the buried surface area calculated from the NIH45-46/gp120 structure, according to embodiments of the present invention.
Figure 6C:
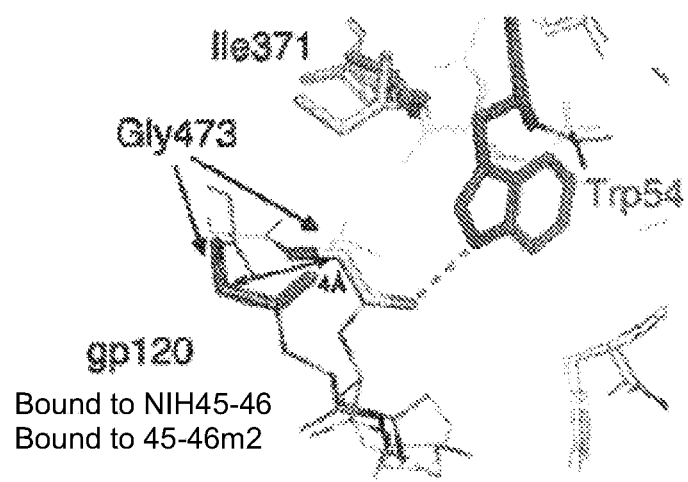
FIG. 6C is a close-up schematic comparison of the interactions of Trp54$_{45-46m2}$ (cyan sidechain) and Gly54$_{NIH45-46}$ (magenta) with gp120 in the structures of 45-46m2/gp120 (gray) and NIH45-46/gp120 (magenta), showing a hydrogen bond (green dashed line) between the nitrogen atom of the Trp54$_{45-46m2}$ indole ring and the main chain carbonyl oxygen of Gly473$_{gp120}$ creates a 4 Å shift (black arrow; Cα-Cα distance) of the gp120 main chain towards Trp54$_{45-46m2}$, and Ile371$_{gp120}$ adopts a different rotamer to accommodate Trp54$_{45-46m2}$, according to embodiments of the present invention.
Figure 6D:
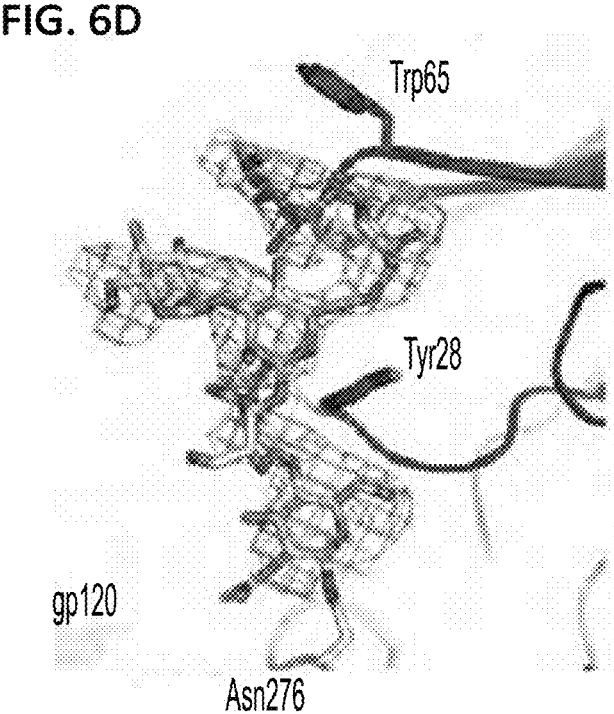
FIG. 6D is a schematic showing the electron density (green mesh; σ=2) for an N-linked glycan attached to Asn276$_{gp120}$, where a portion from the final model of the 45-46m2/gp120 complex is superimposed on a $F_o$-$F_c$ electron density map calculated using the initial model prior to adding the glycan and after several rounds of simulated annealing refinement, according to embodiments of the present invention.
Figure 6E:
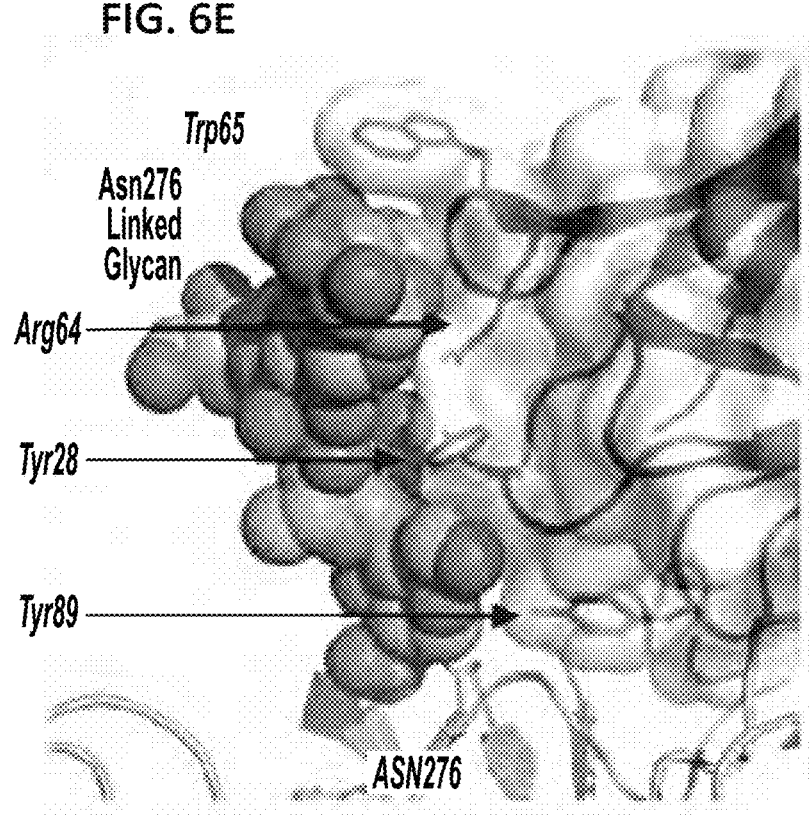
FIG. 6E is a close-up schematic of the Asn276$_{gp120}$-attached glycan and its interactions with the 45-46m2 LC (semi-transparent blue surface), in which the side chains of Tyr28$_{45-46m2}$, Trp65$_{45-46m2}$, Arg64$_{45-46m2}$ and Tyr89$_{45-46m2}$ are shown as sticks, according to embodiments of the present invention.
Figure 7A:
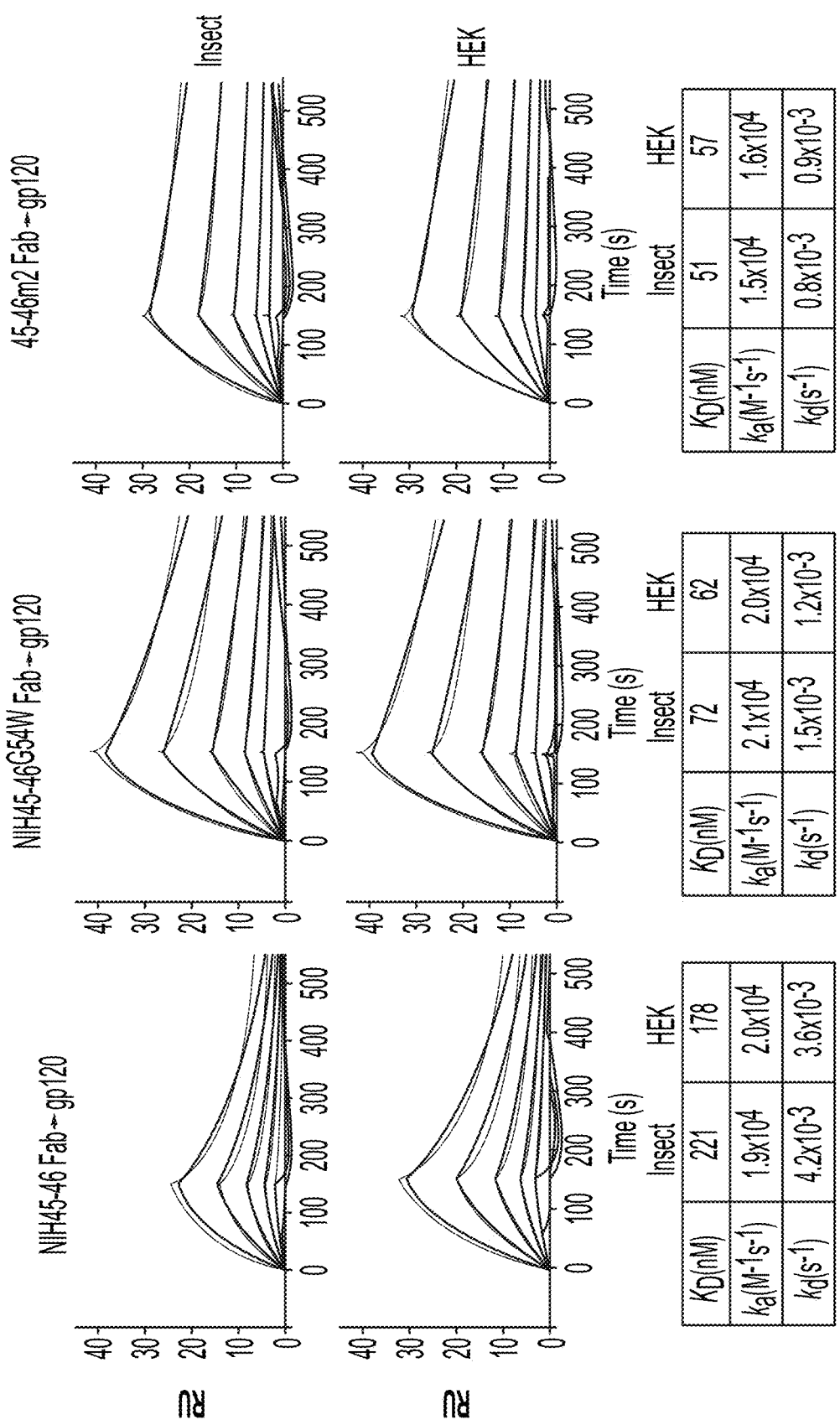
FIG. 7A shows the sensograms (orange curves) that were recorded for the interactions of injected 93TH057 gp120 produced in insect (Hi5) and mammalian (HEK293) cells over immobilized Fabs derived from the indicated antibodies in a 2-fold dilution series ranging from 500 nM-31 nM; where the kinetic constants ($k_a$, $k_d$) were derived from globally fitting the association and dissociation phases using a 1:1 binding model (black curves) and affinities were calculated as $K_D=k_d/k_a$; the residual plots (blue) within each sensogram describe the fit of the model to the data; and each binding experiment was conducted twice: once using gp 120 produced in insect cells; and once using gp120 produced in mammalian cells, according to embodiments of the present invention.
Figure 7B:
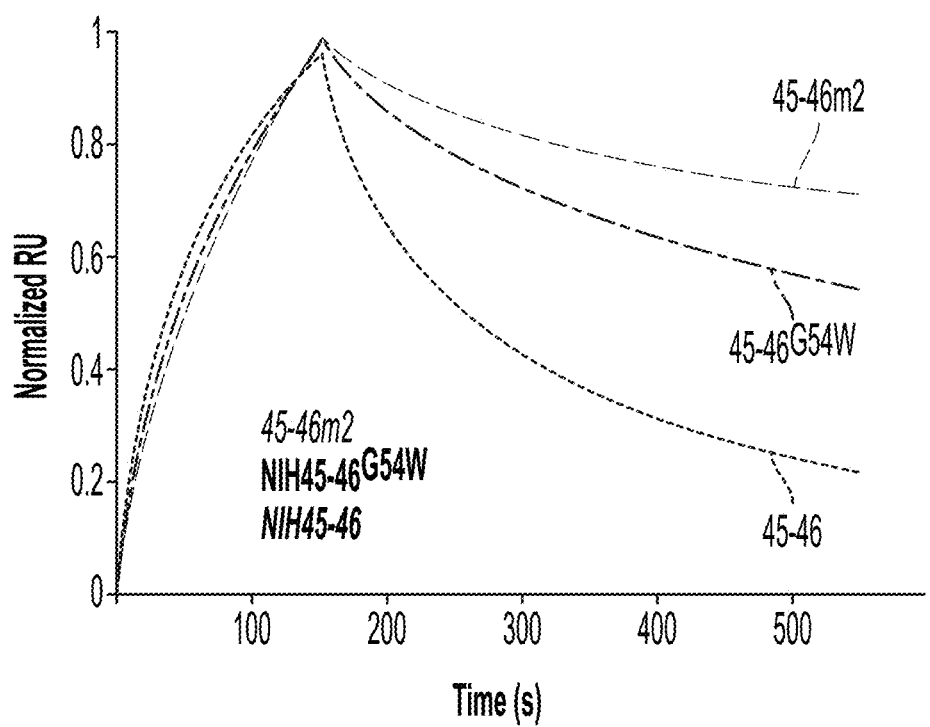
FIG. 7B is a graph of the SPR measurements of 500 nM injected 93TH057 gp120 over the indicated immobilized Fabs, where each curve was normalized to its $R_{max}$, and the gray and white shaded areas designate the association and dissociation phases, respectively, according to embodiments of the present invention.
Figure 8A:
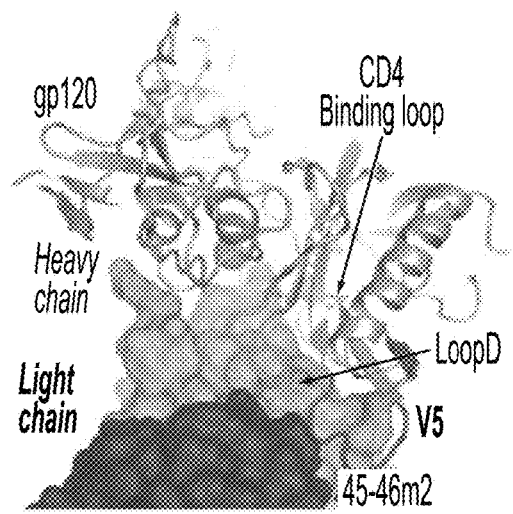
FIG. 8A is a schematic of steric constraints associated with the gp120 N/DNGG motif, in which an overview of loop D (green) and the V5 loop (magenta) of gp120 (gray) are interacting with the surface of the 45-46m2 HC (cyan) and LC (blue), and the CD4-binding loop of gp120 is shown in orange, according to embodiments of the present invention.
Figure 8B:
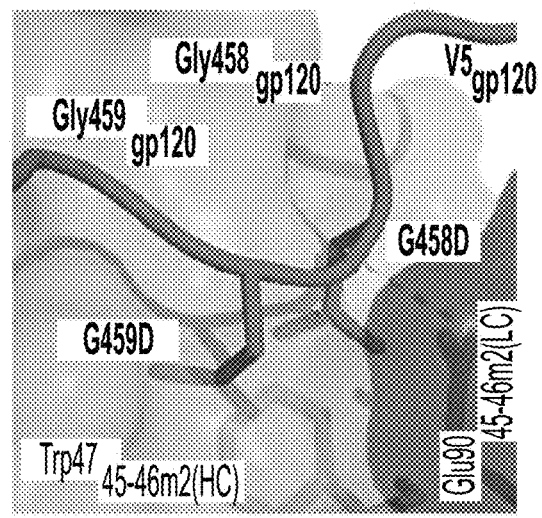
FIG. 8B is a schematic of the gp120 V5 loop region showing Gly458$_{gp120}$ and Gly459$_{gp120}$ with overlaid prediction of the consequences of aspartic acid substitutions at these positions (Asp458$_{gp120}$ and Asp459$_{gp120}$; pink sticks), in which both aspartic acids could clash with Trp47$_{45-46m2(HC)}$, according to embodiments of the present invention.
Figure 8C:
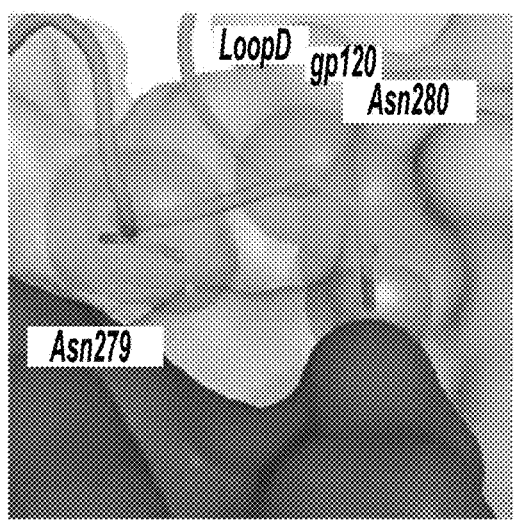
FIG. 8C is a schematic of Asn279$_{gp120}$ and Asn280$_{gp120}$ (sticks and semi-transparent spheres) interactions with 45-46m2, in which a hydrogen bond (orange dashed line) between Asn279$_{gp120}$ and the nitrogen atom of the Trp102$_{45-46m2(HC)}$ indole ring is shown, according to embodiments of the present invention.
Figure 8D:
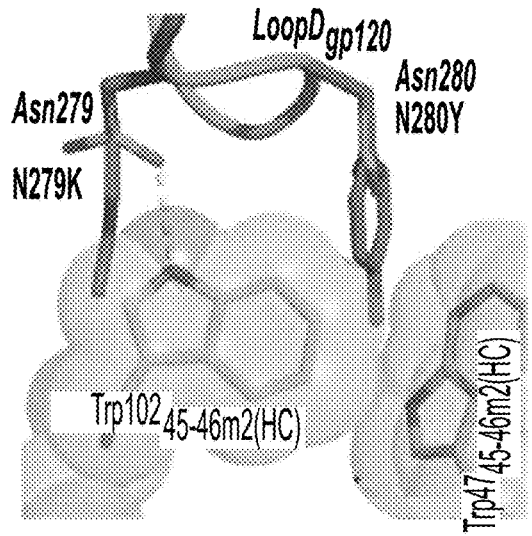
FIG. 8D is a schematic showing possible steric clashes between a lysine or a tyrosine in gp120 positions 279 and 280 (pink) and Trp102$_{45-46m2(HC)}$ and Trp47$_{45-46m2(HC)}$, according to embodiments of the present invention.
Figure 8E:
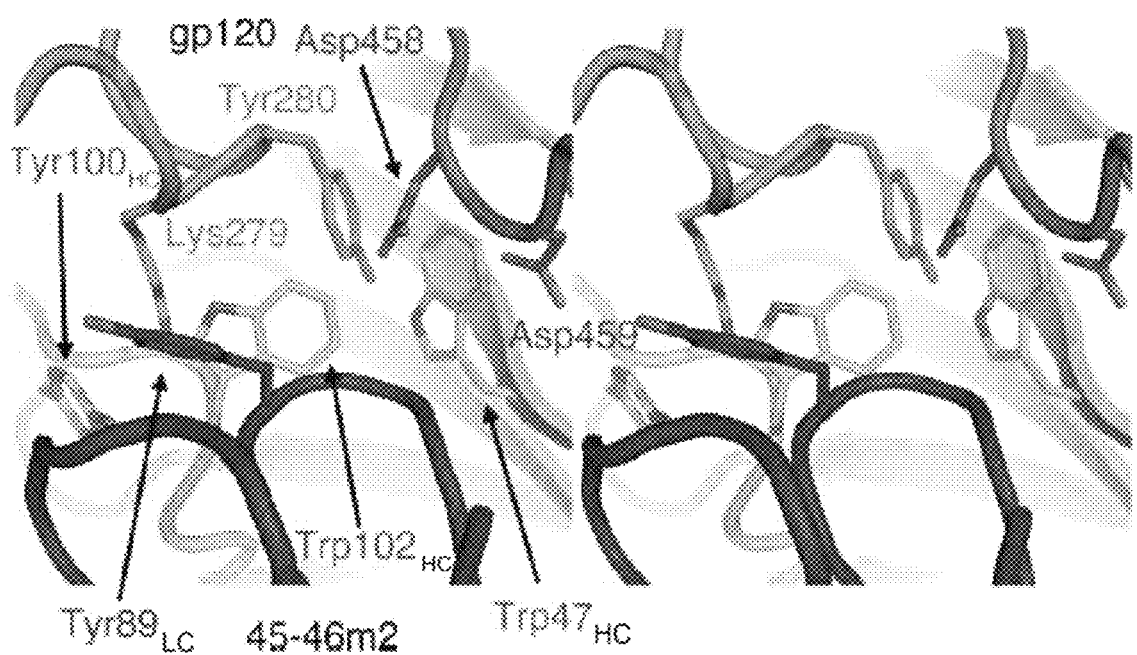
FIG. 8E is a stereo image showing modeled substitutions in the gp120 N/DNGG consensus sequence (Lys279$_{gp120}$, Tyr Asp458$_{gp120}$, and Asp459$_{gp120}$) at the interface with of gp120s with non-consensus substitutions, are shown together with Trp102$_{45-46m2\ HC}$ and Trp47$_{45-46m2\ HC}$, according to embodiments of the present invention.

Considering the close contacts that 45-46m2 makes with Asn279$_{gp120}$ (FIG. 8C), an N-linked glycan attached to Asn279gp120 would most likely prevent 45-46m2 binding to gp 120s on spike trimers, resulting in resistance to neutralization. The saturation of the YU-2$^{A281T}$ neutralization curves at values less than 100% (FIG. 11; FIG. 12C) is consistent with both a sensitive and a resistant population of virions, suggesting only partial incorporation of N-linked glycan attached to Asn279$_{gp120}$. Incomplete processing at the level of individual gp120 protomers would likely give rise to heterogeneously glycosylated trimeric Env spikes, i.e., trimers that were fully, partially, or not glycosylated at residue 279. At the population level, the sensitivity of YU-2$^{A281T}$ viruses to 45-46m2-like antibodies would vary according to the Env composition of each virus, thereby giving rise to both resistant and sensitive virions within the set of YU-2A281T viruses.

Figure 15:
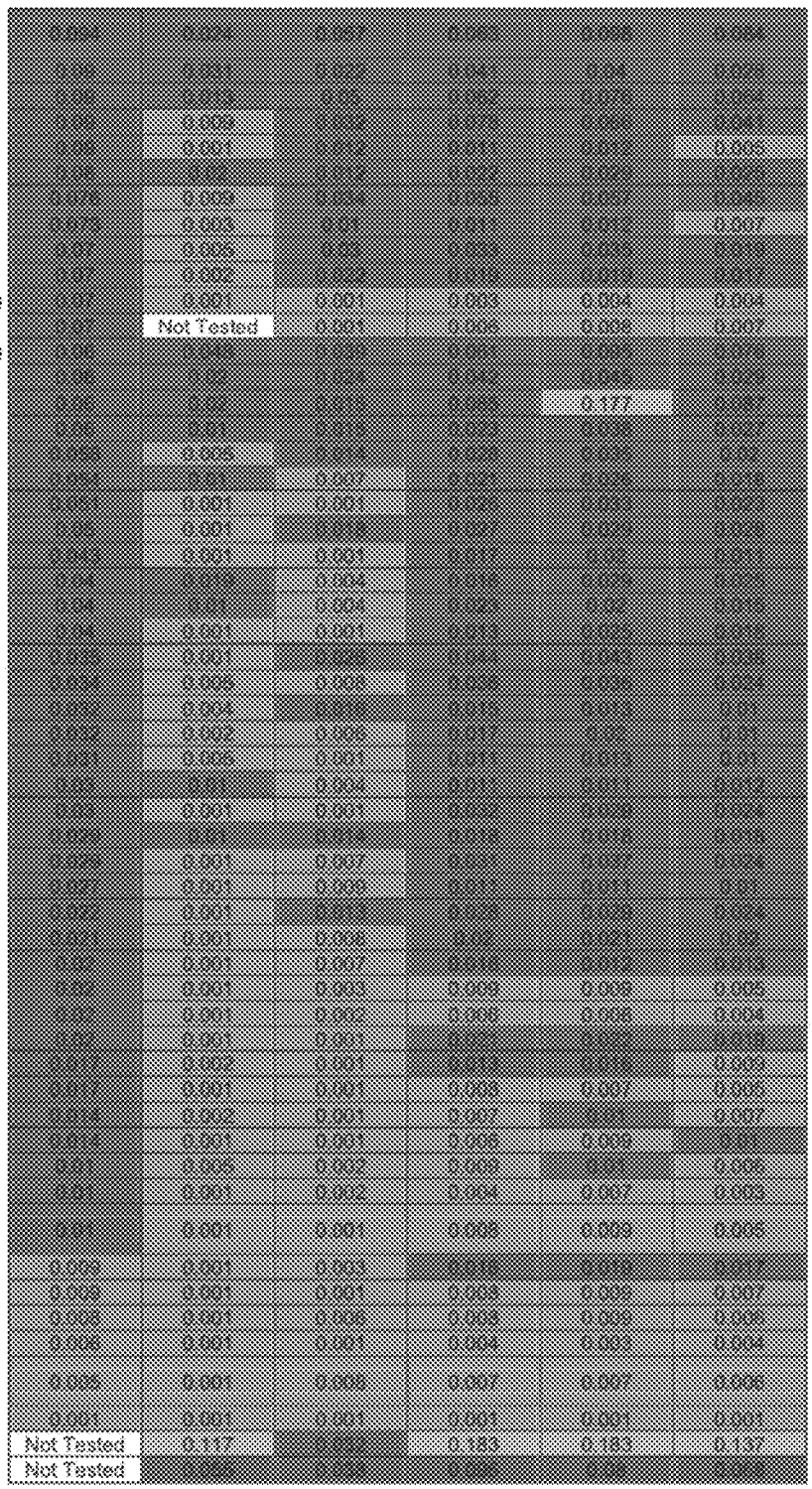
FIG. 15 is table of IC50 values for NIH45-46$^{G54W}$, 45-46m2, and 45-46m7, 45-46m25 and 45-46m28 antibodies against the various HIV viral strains as indicated, according to embodiments of the present invention.
Figure 16:
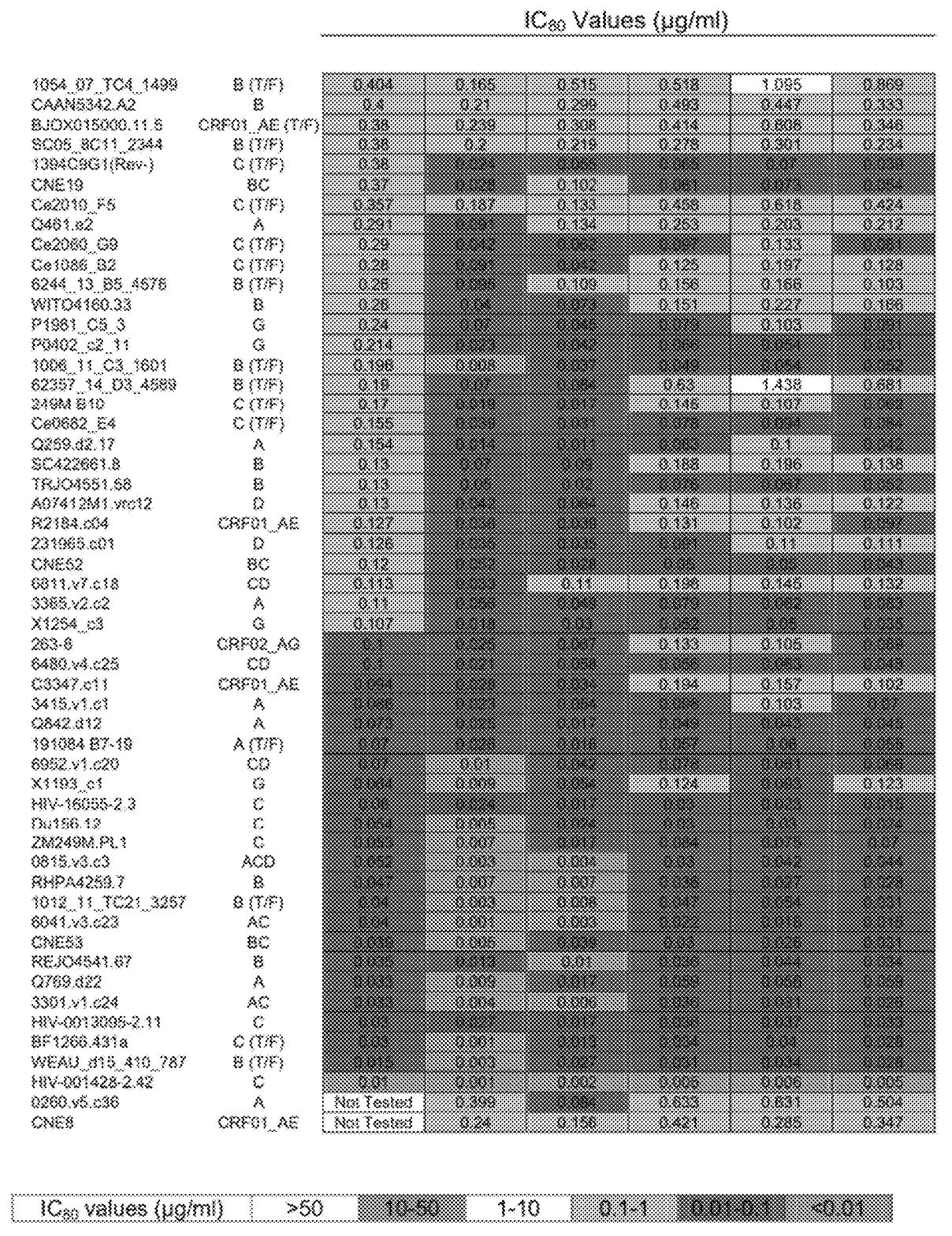
Figure 18:
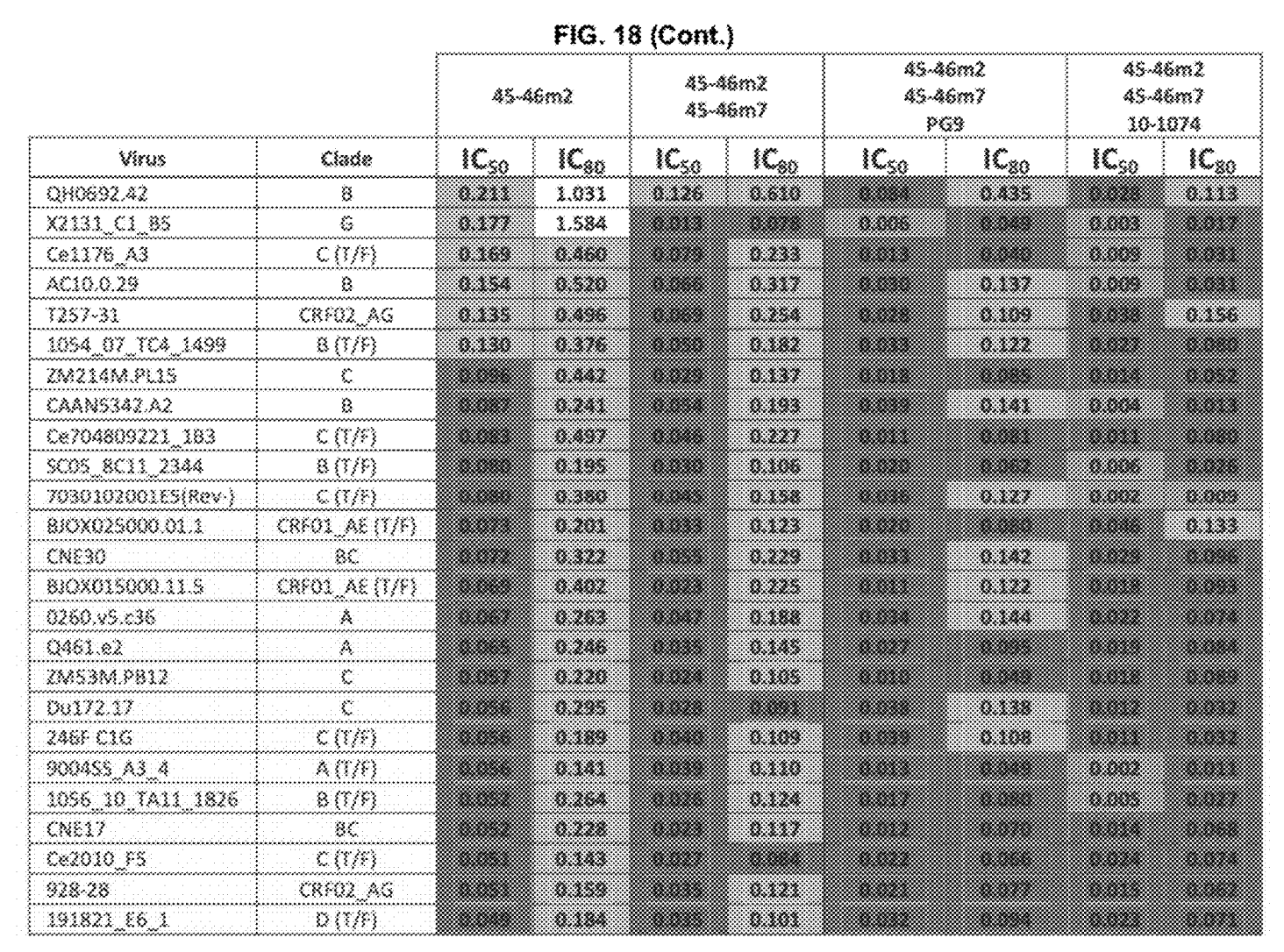
Figure 18:
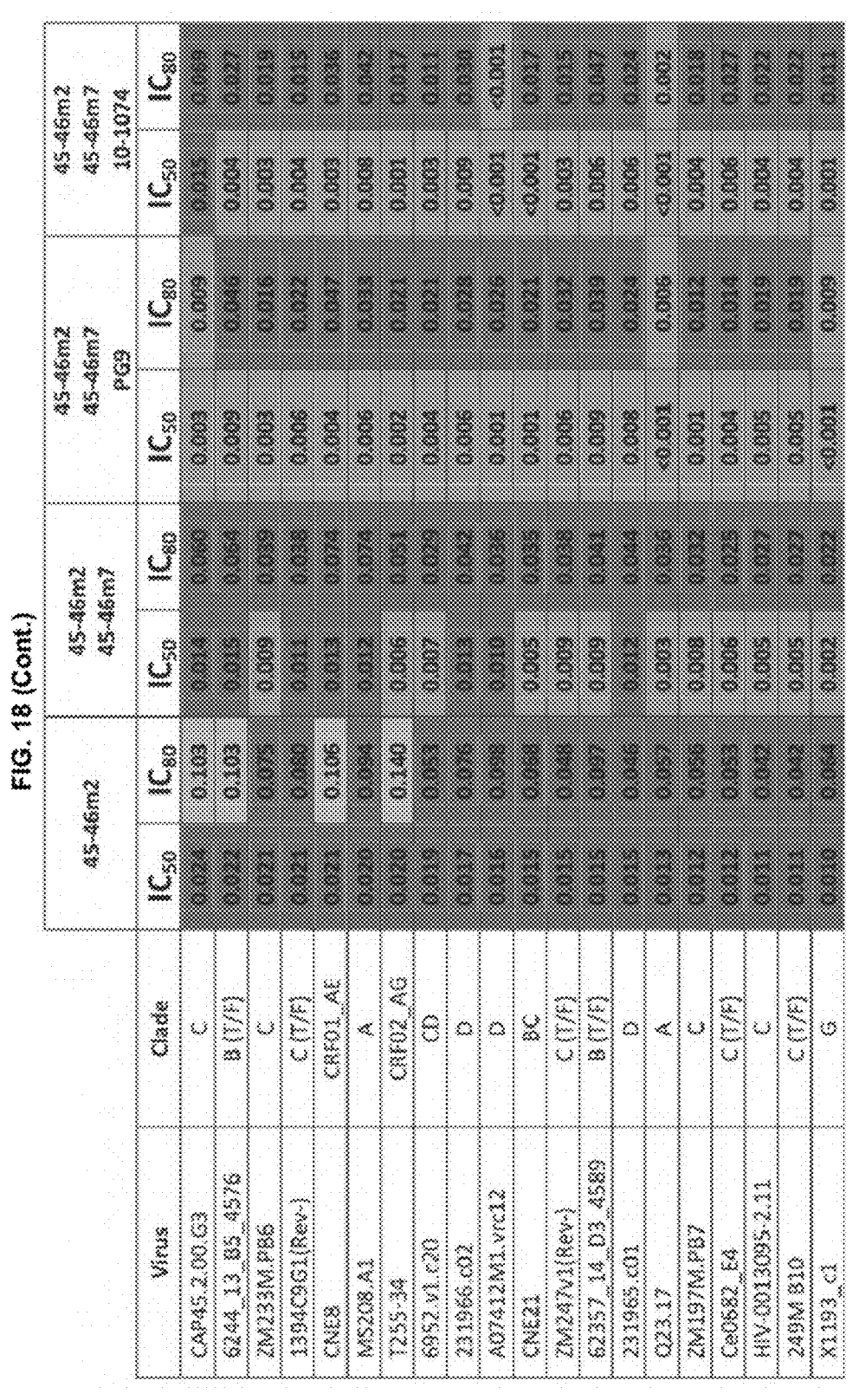

Example 3. Combinations of Antibodies Improve Anti-HIV-1 Activity In Vitro and In Vivo. The breadth and potencies of selected antibodies were evaluated alone and in combination using the 118-strain cross-clade virus panel (FIGS. 15-16). 45-46m7, 45-46m25 and 45-46m28 effectively neutralized YU-2 N/DNGG consensus variants, but these antibodies and a 45-46m2/45-46m7 combination did not neutralize consensus variant strains that were resistant to 45-46m2 (FIGS. 15-16, 18). These results suggest that changing Trp4745-46m2 (HC) to a smaller amino acid can only partially alleviate steric constraints associated with PVL antibody binding to an N/DNGG consensus variant. Thus effective neutralization by 45-46m7, 45-46m25 and 45-46m28 of escape mutants that utilize non-N/DNGG consensus residues is likely only when the parent viral strain is sensitive to a PVL antibody. However, given the broad neutralization profiles of parental PVL antibodies (West et al., 2012, supra), strains resistant to parental PVLs and to 45-46m7, 45-46m25 and 45-46m28 due to changes in the gp120 N/DNGG consensus sequence are likely to be rare. Addition of 10-1074, a more potent clonal variant of PGT121 (Walker et al., 2011, Nature 477:466-470, the entire contents of which are herein incorporated by reference) that recognizes a carbohydrate-dependent epitope associated with the gp120 V3 loop (Mouquet et al., 2012, PNAS, 109: E3268-3277, the entire contents of which are herein incorporated by reference), or PG9, a carbohydrate-dependent bNAb recognizing a V1/V2 epitope (Walker et al., 2009, *Science* 326:285-289, the entire contents of which are herein incorporated by reference), into the mixture resulted in neutralization of almost all resistant strains (FIG. 18).

Figure 13A:
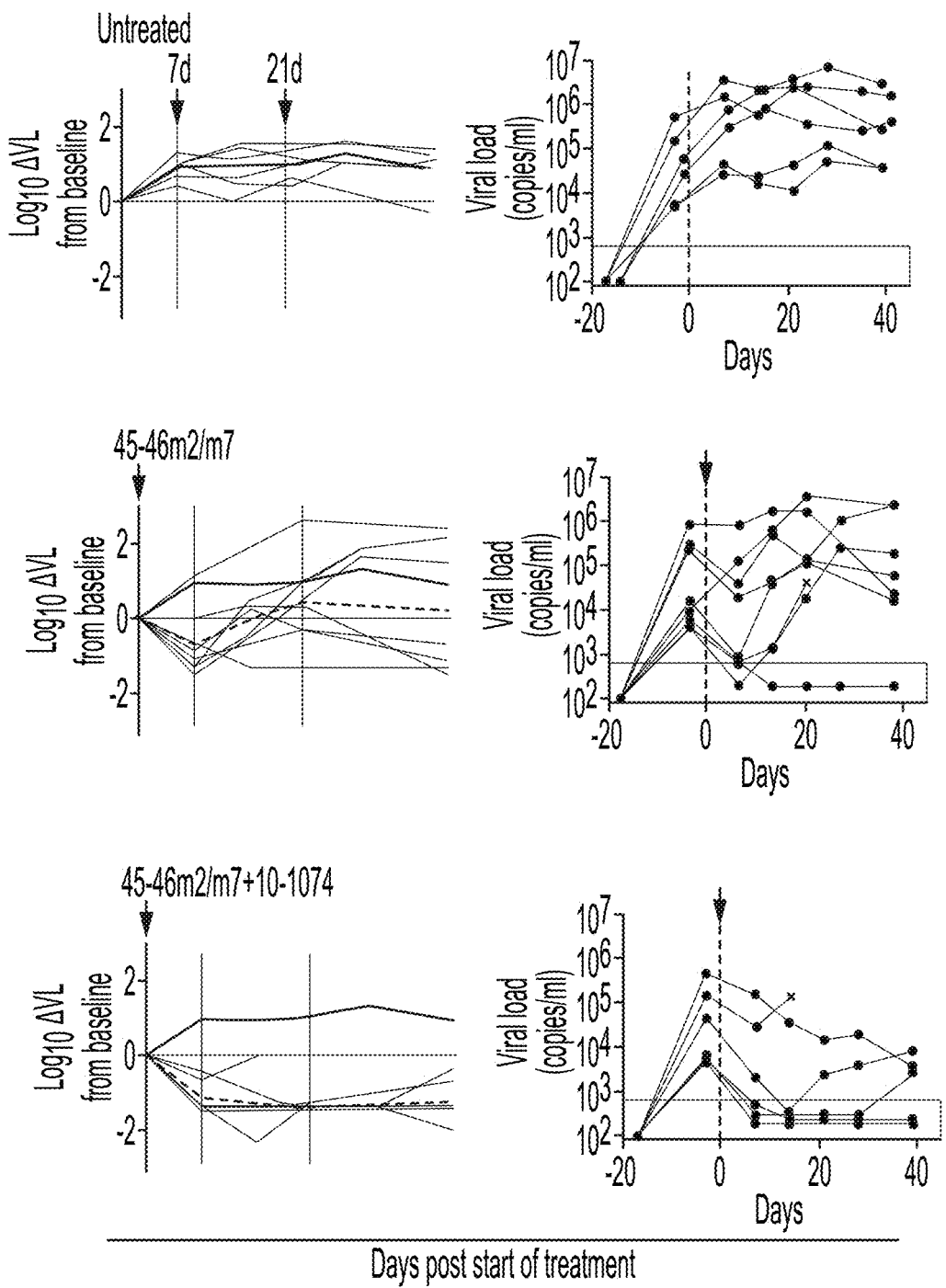
FIG. 13A shows the results from HIV-1 therapy by a combination of two [45-46m2+45-46m7, labeled 45-46m2/m7] or three [45-46m2/m7+10-1074] bNAbs in HIV-1$_{YU2}$-infected humanized mice, in which the viral load is shown: the left panels show the viral load change from baseline (log$_{10}$ HIV-1 RNA copies/mL), and the right panels show the absolute viral load per mouse (RNA copies/mL), where each line represents a single mouse, and red arrows indicate start of antibody treatment; green lines, geometric average of untreated mice; red lines, geometric average of antibody treatment group indicated, the treatment groups were analyzed in parallel and reflect a single experiment comprising six control animals (untreated), eight mice treated with 45-46m2/m7, and six animals treated with the combination 45-46m2/m7+10-1074, according to embodiments of the present invention.
Figure 13B:
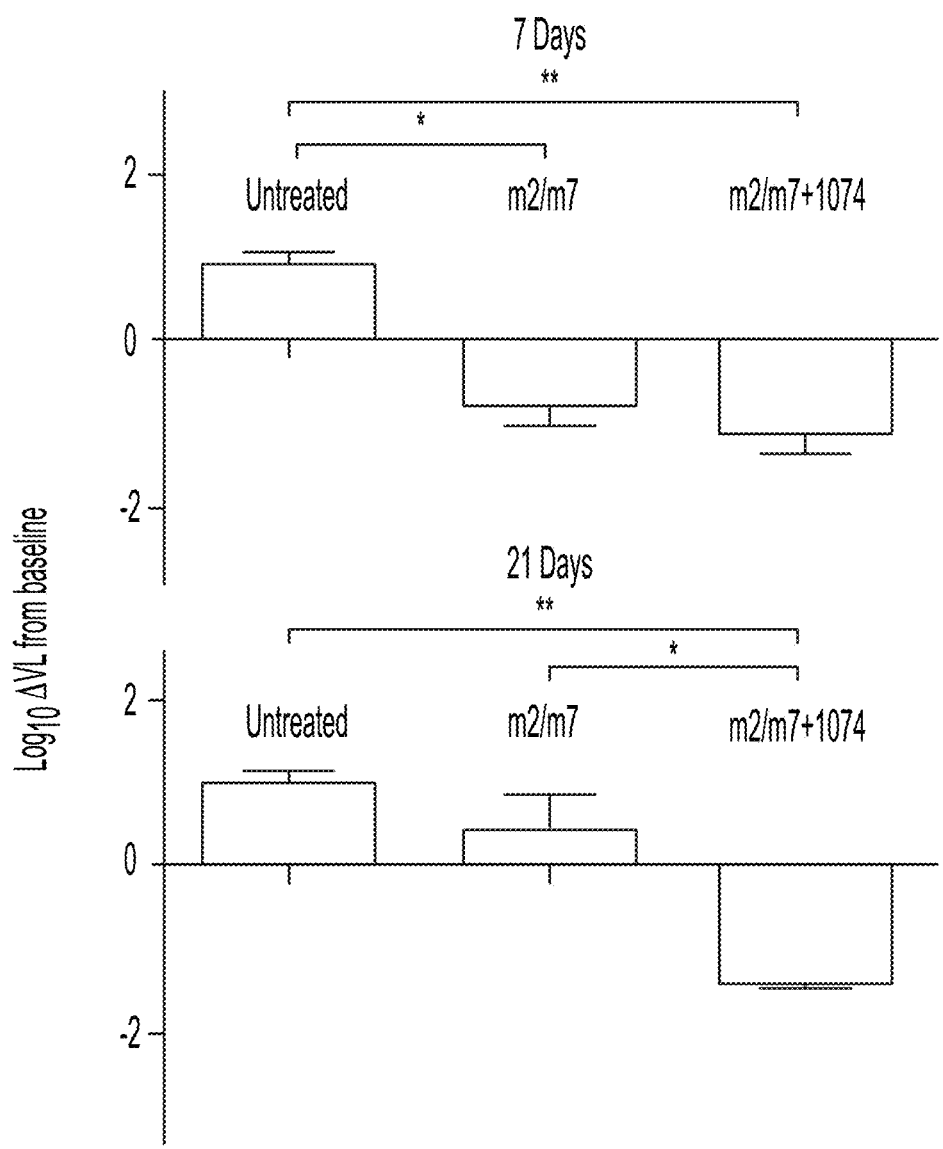
FIG. 13B is a graphical representation of the average viral load change (log$_{10}$ HIV-1 RNA copies/mL) from baseline at the indicated number of days from start of therapy (mean and standard error are shown), where the statistical test: Kruskal-Wallis test with Dunn's multiple comparison post-hoc test, asterisks (*p≤0.05; **p≤0.01) reflect statistically significant differences between the treatment groups indicated, according to embodiments of the present invention.
Figure 13C:
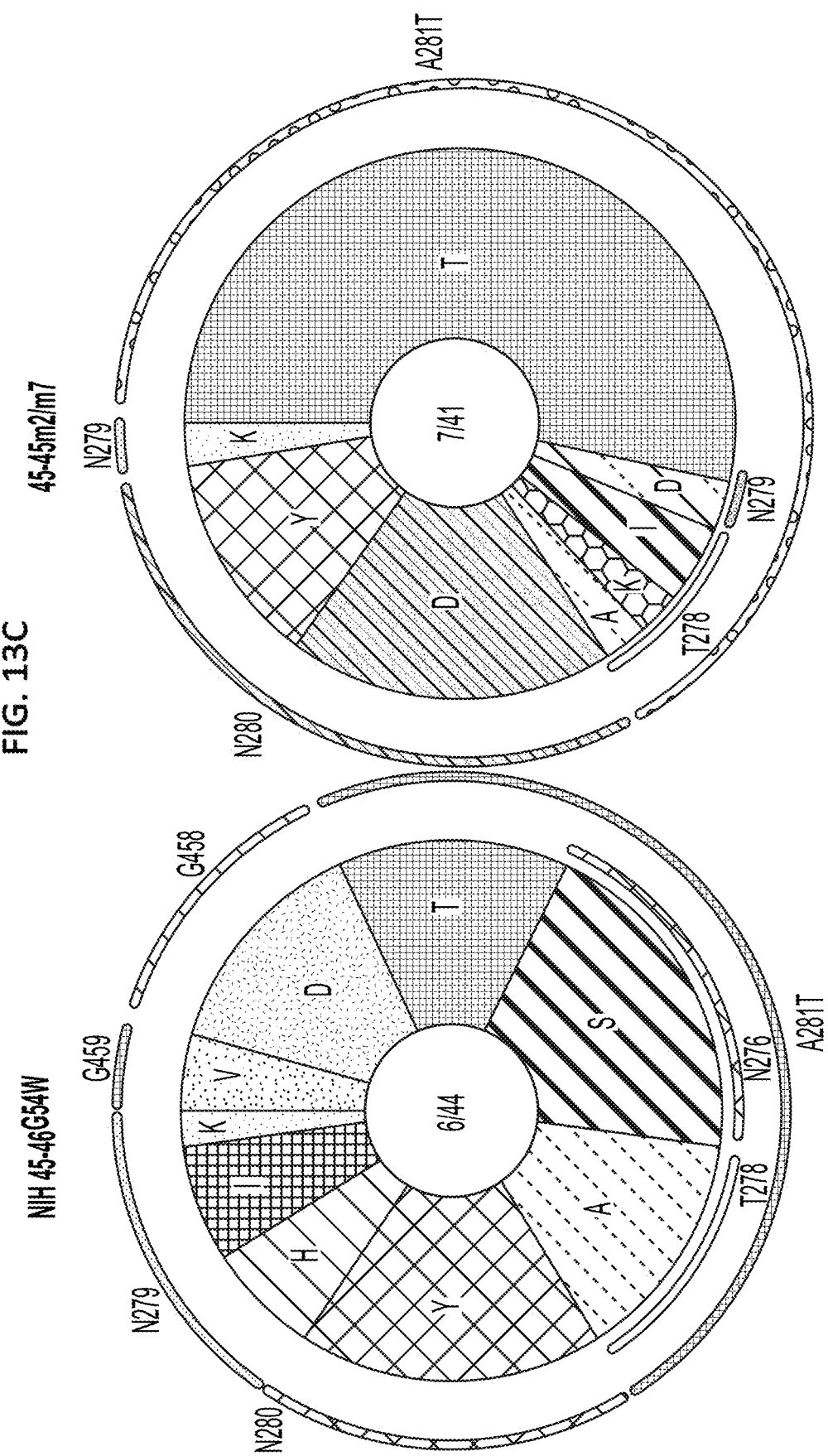
FIG. 13C shows two pie charts illustrating the distribution of amino acid changes in gp 120 at sites targeted by NIH45-46$^{G54W}$ (left; data from (Klein et al., 2012, as discussed and incorporated herein) versus the 45-46 (m2/m7) combination (right), in which the wedge sizes reflect the percent of gp 120 sequences carrying the indicated resistance mutation at the time of viral rebound, and the center numbers refer to the number of mice (left) and the number of gp 120 sequences (right) for each set of data, where the mutations listed within the A281T sector of the 45-46m2/m7 pie chart reflect compensatory mutations accompanying A281T, according to embodiments of the present invention.
Figure 14B:
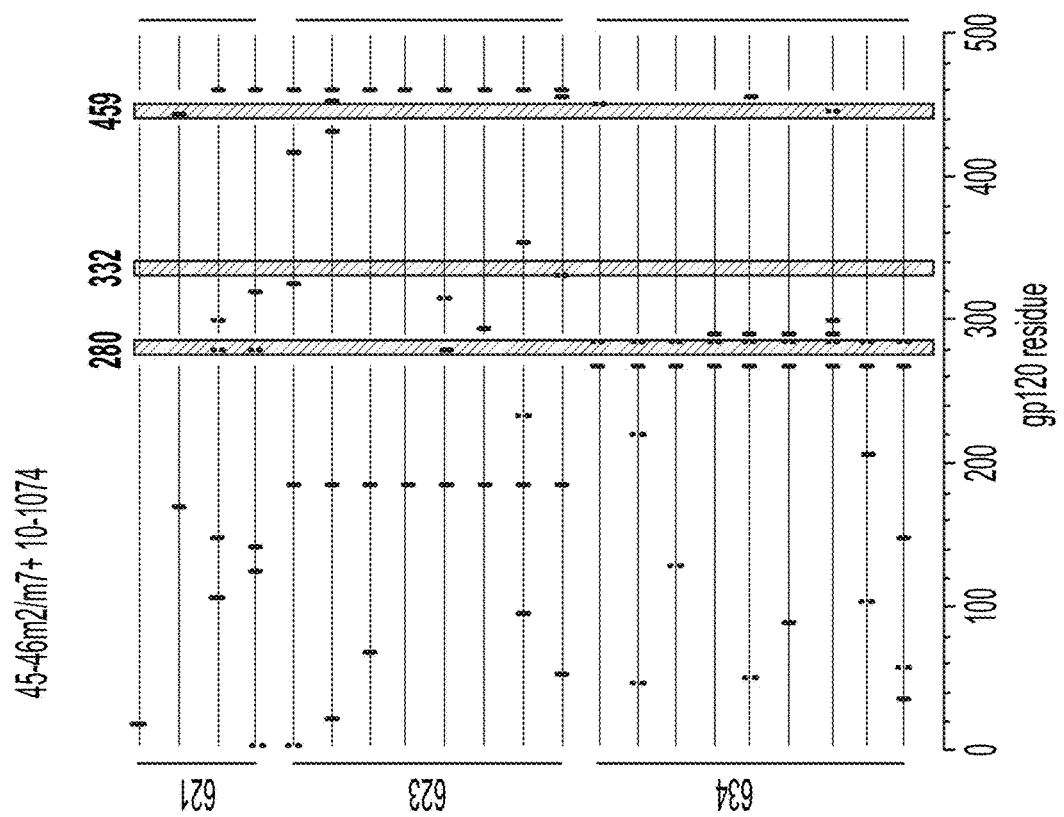
FIGS. 14A-14B shows mutation analysis of gp120 sequences during antibody therapy, where
Figure 14A:
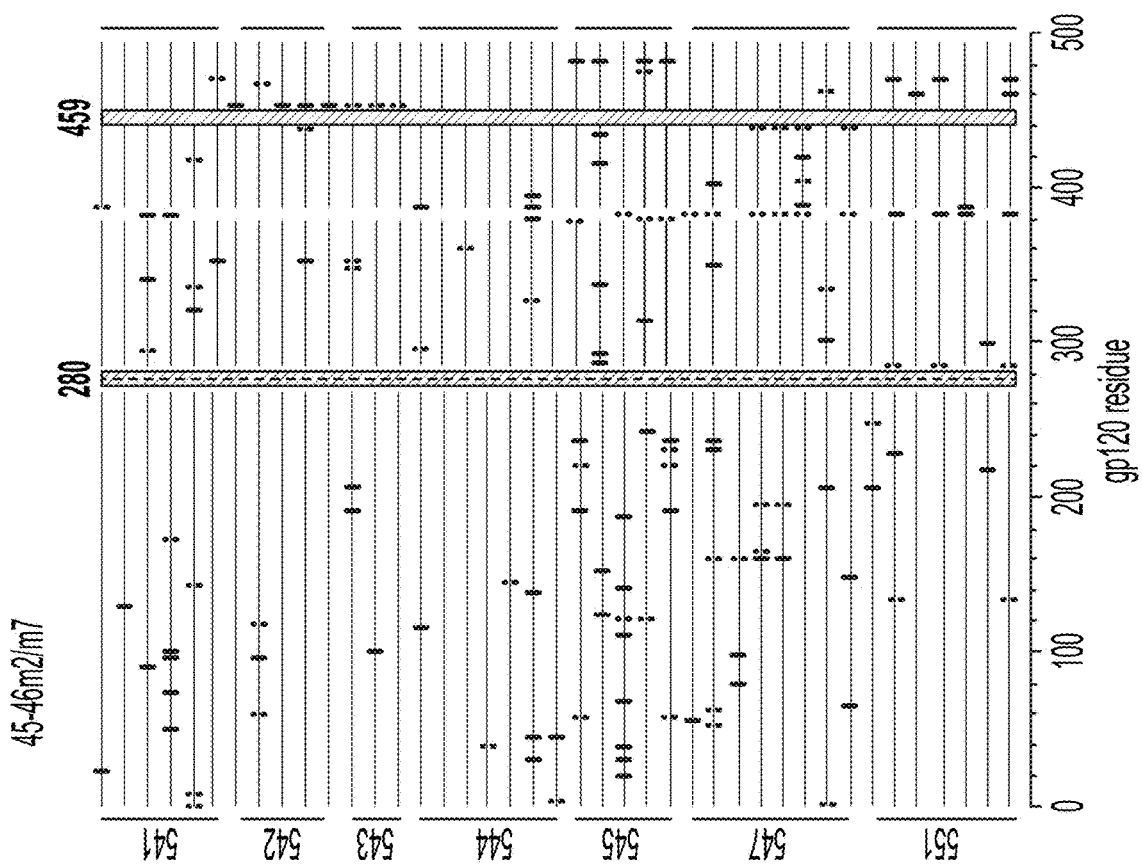

Antibodies can drive HIV-1 mutation or even control viral replication in humanized mice (Klein et al., 2012), offering the opportunity to examine HIV-1 escape mutations that arise in response to treatment with selected bNAbs. Escape mutations in HIV-1Yu-2 that arose in response to a 45-46m2/45-46m7 combination were compared to monotherapy with NIH45-46$^{G54W}$ Treatment with 45-46m2/45-46m7 resulted in a significant initial drop in viremia by 7 days (FIGS. 13A-13B; p=0.0057). Although viremia rebounded to pre-treatment levels after 21 days in seven of eight mice, the Env sequences isolated from the 45-46m2/45-46m7-treated viremic mice revealed striking differences compared with viruses isolated after escape from NIH45-46$^{G54W}$ monotherapy (Klein et al., 2012) (FIG. 13C; FIG. 14A; FIG. 19A). Mutations in the GG portion of the N/DNGG consensus sequence (Gly458gp120 and Gly459$_{gp120}$), which resulted in resistance to NIH45-46$^{G54W}$ (FIG. 10) and that were isolated following NIH45-46$^{G54W}$ monotherapy (Klein et al., 2012), were absent (FIG. 13C; FIG. 14A; FIG. 19A). Although effective against potential mutations in the V5 region (residues 458$_{gp120}$ and 459$_{gp120}$), the combination of 45-46m2 and 45-46m7 did not eliminate mutations in loop D (residues 279$_{gp120}$ and 280$_{gp120}$). This may indicate that the antibody concentrations reached in vivo were not sufficient. Consistent with this suggestion, the in vitro IC50 values for 45-46m2 and 45-46m7 against loop D variants were >0.1 μg/ml whereas the IC50 values for V5 variants were <0.01 μg/ml (FIG. 10).

The predominant escape mutant found in viruses isolated from the 45-46m2/45-46m7-treated mice was A281T$_{gp120}$, a substitution that introduces a potential N-linked glycosylation site at Asn279gp120 and results in a less fit virus (FIG. 12B). In the context of an Asn279$_{gp120}$-linked glycan, compensatory mutations to remove the potential N-linked glycosylation site at Asn276$_{gp120}$ were selected (FIG. 13C; FIG. 14A; FIG. 19A). Specifically, attachment of an N-linked glycan to Asn276$_{gp120}$ was prevented by altering the asparagine (N276D and N276S) or the final residue (T278A) in the Asn-X-Ser/Thr potential N-linked glycosylation sequence motif. It is believed that a glycan attached to Asn279$_{gp120}$ in a gp120 lacking Asn276$_{gp120}$-attached glycan could be pushed toward the empty space created by elimination of the Asn276$_{gp120}$ glycan to facilitate binding to CD4. Thus, eliminating the glycan at Asn276$_{gp120}$ could compensate for the otherwise unfavorable addition of a glycan to Asn279$_{gp120}$. The suggestion that mutations to remove an Asn276$_{gp120}$-linked glycan are compensatory mutations required when an Asn279$_{gp120}$-linked glycan is introduced rather than escape mutations on their own is consistent with potent neutralization of N276S and T278A mutants of YU-2 by NIH45-46$^{G54W}$, 45-46m2 and 45-46m7 (FIG. 12C) and the emergence of N276S and T278A mutations only when A281T was present (FIG. 14A; FIG. 19A).

Figure 19B:
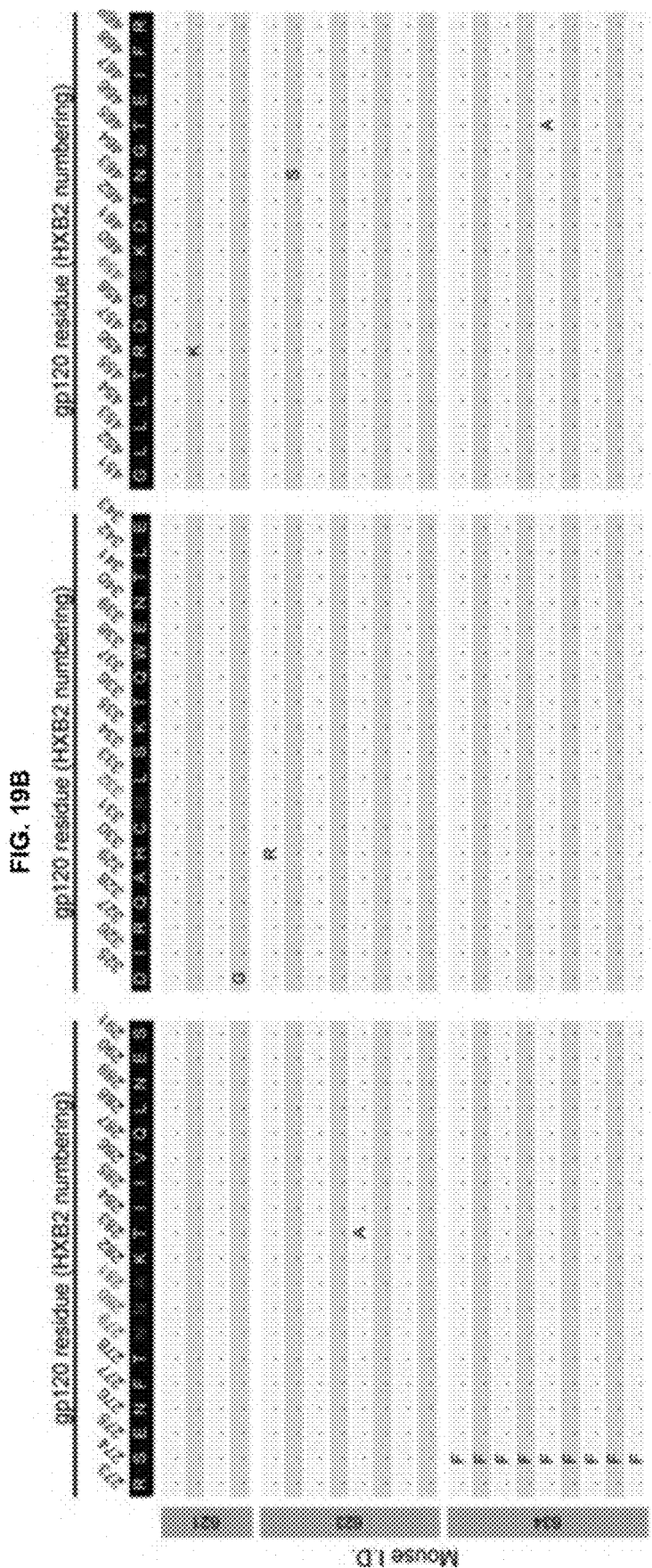

When HIV-1$_{YU2}$-infected mice were treated with a combination of 45-46-m2, 45-46m7 and 10-1074 (Mouquet et al., 2012, PNAS, 109: E3268-3277, the entire contents of which are incorporated by reference), control of viremia in all animals that lived beyond 20 days after the start of treatment (FIGS. 13A-13B). With regards to the animal that died prior to this time, gp120 sequences just prior to its death did not harbor mutations that would indicate escape from either 10-1074 or 45-46m2/m7 (FIG. 14B; FIG. 19B). While some mice had detectable viral loads during treatment, known escape mutations were not found in viruses isolated during treatment for the bNAbs used in the treatment mix (FIG. 14B; FIG. 19B). Thus the combination of 45-46m2 and 45-46m7 effectively reduced the available pathways for escape, and the 45-46m2, 45-46m7 and 10-1074 combination potently treated HIV-1Yu-2-infected mice.

Materials and Methods

Example 4. Vector Construction, Protein Expression and Protein Purification. Modifications of NIH45-46 heavy and light chain genes were made using QuikChange Lightning (Agilent Technologies) and verified by DNA sequencing (Eton Bioscience). Antibodies were expressed as IgGs using described protocols (Diskin et al., 2010, Nature structural & molecular biology 17:608-613, the entire contents of which are herein incorporated by reference). Briefly, secreted IgGs from polyethyleneimine (25 kD, linear; Polysciences)-mediated, transiently-transfected HEK293-6E cells were captured on protein A or protein G affinity columns (GE Healthcare) and eluted in 100 mM citrate pH 3.0, 150 mM sodium chloride. Antibodies subsequently used in neutralization assays were dialyzed into 10 mM citrate pH 3.0, 150 mM sodium chloride and adjusted to a concentration of 1 mg/ml. Fab fragments for crystallization and binding assays were obtained by digesting IgGs in 20 mM Tris pH 8.0, 150 mM sodium chloride (TBS) with a 1:100 ratio of papain (Sigma) activated in 50 mM phosphate pH 7.0, 2 mM ethylenediaminetetraacetic acid, 10 mM cysteine at 37° C. until completion of the cleavage (20 min-60 min, monitored by SDS-PAGE). The Fc was removed by protein A chromatography and Fabs were further purified using Superdex 200 (GE Healthcare) 10/300 Size Exclusion Chromatography (SEC).

The clade A/E 93TH057-derived gp120 core (Zhou et al., 2010, Science 329:811-817, the entire contents of which are herein incorporated by reference) (a gp120 construct lacking the V1/V2 and V3 loops) was expressed in insect cells and purified using previously-described protocols (Diskin et al., 2011, supra). Briefly, supernatants from baculovirus-infected insect cells were collected, buffer exchanged into TBS and passed through a Ni$^{2+}$-NTA affinity column (GE Healthcare). gp120 was eluted from the column using TBS plus 250 mM imidazole and purified using Superdex 200 16/60 SEC (GE Healthcare) in TBS supplemented with 0.02% (w/v) sodium azide.

Figure 9:
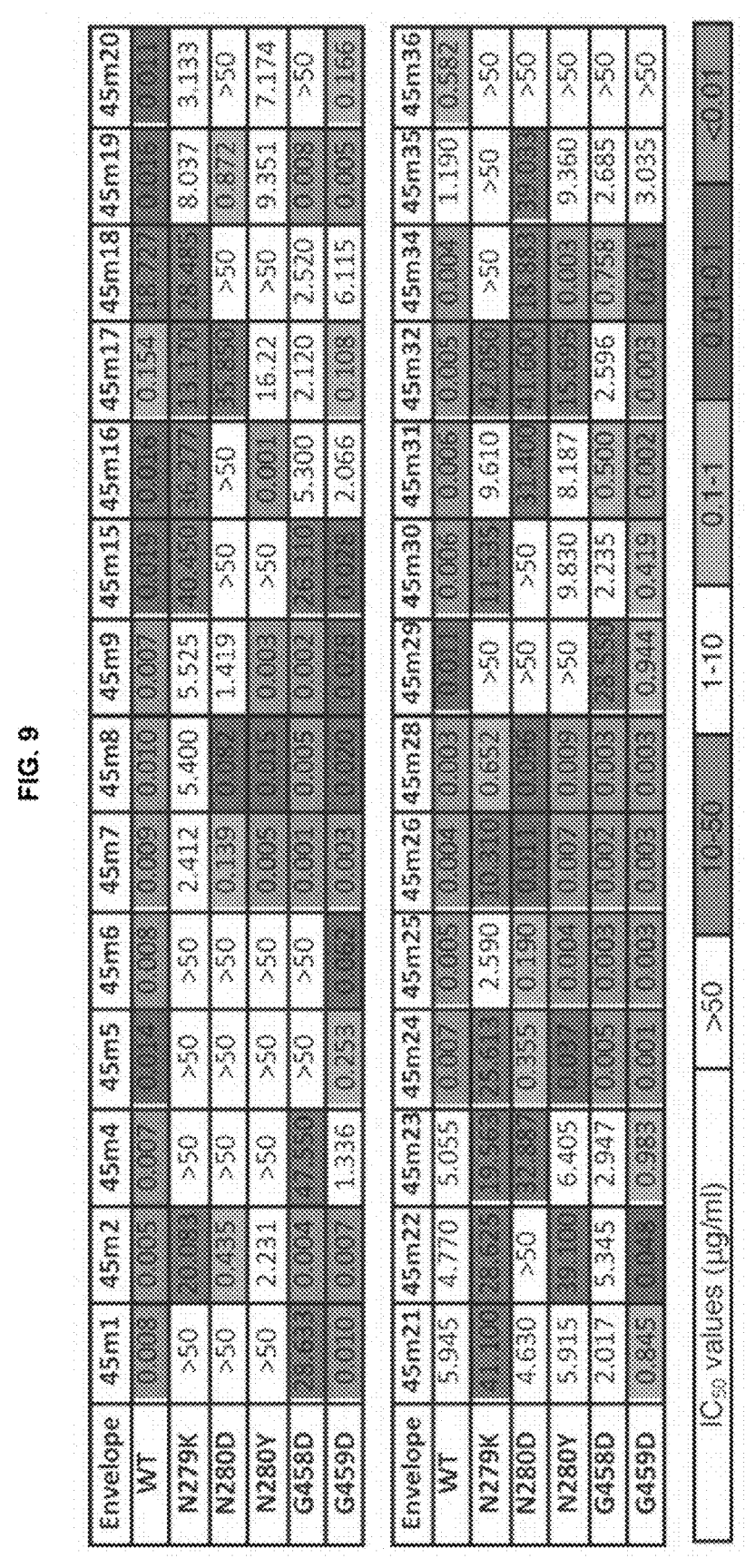

Example 5. In Vitro Neutralization Assays. A previously-described pseudovirus neutralization assay was used Montefiori, 2005, Current protocols in immunology, Edited by John E. Coligan et al., Chapter 12, Unit 12.11, the entire contents of which are herein incorporated by reference) to assess the neutralization potencies of the various antibodies against multiple HIV-1 strains. YU-2 escape mutant pseudoviruses were generated by co-transfecting HEK293T cells with vectors encoding Env and a replication-deficient HIV-1 backbone as described (Montefiori, 2005). Neutralization assays were performed in-house for evaluating antibody mutants against the YU-2 escape mutants (FIG. 15; FIG. 9) and by the Collaboration for AIDS Vaccine Discovery (CAVD) core neutralization facility for testing a subset of the antibodies against a large panel of isolates (FIGS. 16-17). Some of the in-house data were derived from neutralization assays that were dispensed automatically by a Freedom EVO® (Tecan) liquid handler (IC50 values derived from manual and robotic assays agreed to within 2-4 fold.) In all cases, neutralization was monitored by the reduction of a Tat-induced reporter gene (luciferase) in the presence of a three- or five-fold antibody dilution series (each concentration run in duplicate or triplicate) after a single round of pseudovirus infection in TZM-bl cell line (Montefiori, 2005). Antibodies were incubated with 250 viral infectious units at 37° C. for one hour prior to incubation with the reporter cells (10,000 per well) for 48 hours. Luciferase levels were measured from a cell lysate using BrightGlo (Promega) and a Victor3 luminometer (PerkinElmer). Data were fit by Prism (GraphPad) using nonlinear regression to find the concentration at which 50% inhibition occurred (IC50 value). For evaluating the neutralization of YU-2 escape mutants, at least two independent experiments were performed. FIG. 6 lists the average IC$_{50}$ values for the various 45-46 mutants if 0.1< (IC$_{50}$ 1/IC$_{50}$ 2)<10. In cases where the two IC$_{50}$ values did not agree, additional experiments were performed. The reported IC$_{50}$ values for NIH45-46$^{G54W}$, 45-46m2, and 45-46m7 are averages calculated from at least five independent experiments.

Example 6. Crystallization, Data Collection, Model Building and Refinement. 45-46m2 Fab was purified by Superdex 200 (GE Healthcare) 10/300 SEC in 100 mM citrate pH 3.0, 150 mM sodium chloride and combined with an equimolar amount of 93TH057 gp120. After concentration using an Amicon™ (Millipore) spin column, the complex was incubated with 40,000 units of Endoglycosidase H (NEB) per 2 mg of gp 120 in the absence of detergents at 37° C. for 16 hours in the manufacturer's recommended buffer. The complex was further purified using Superdex200 (GE Healthcare) SEC in TBS and concentrated to $OD_{280}$=9.5. Data for the structure determination were collected from rod-like crystals grown in a vapor diffusion sitting drop set at a final volume of 2 µl (1:1 protein/reservoir ratio) with 12% (v/v) isopropanol, 10% (w/v) polyethylene glycol 10,000 kD, 0.1 M citrate pH 5.0 at 20° C. The crystals were briefly soaked at 30% (v/v) isopropanol, 5% glycerol, 10% (w/v) polyethylene glycol 10,000 kD, 0.1 M citrate pH 5.0 before flash cooling using liquid nitrogen.

Data to 2.82 Å resolution were collected from a P21 21 21 45-46m2/gp120 complex crystal with similar cell dimensions as the NIH45-46/gp120 crystals (Diskin et al., 2011, supra) at the Stanford Synchrotron Radiation Lightsource (SSRL) beamline 12-2 using a Pilatus 6M (Dectris) detector and 0.9537 Å radiation (FIGS. 19A-19B). Data were indexed, integrated and scaled using XDS (Kabsch, 2010) (FIGS. 19A-19B). Using Phaser and the NIH45-46/gp120 complex (PDB: 3U7Y) as a search model, we found a molecular replacement solution comprising one 45-46m2 Fab and one gp 120 in the asymmetric unit. Several rounds of simulated annealing were performed in initial refinement cycles to minimize model bias. The structure was refined using iterative cycles of refinement using the Phenix crystallography package and Coot for manual re-building. To facilitate refinement at 2.82 Å, the model was restrained using the NIH45-46/gp120 structure as a reference and applying secondary structure restraints. The final model ($R_{free}$=23.1%, $R_{work}$=19.3%) consists of 5998 protein atoms, 242 carbohydrate atoms and 23 water molecules. 95.63%, 4.1%, and 0.26% of the residues are in the favored, allowed, and disallowed regions, respectively, of the Ramachandran plot. The first glutamine of the 45-46m2 HC was modeled as 5-pyrrolidone-2-carboxylic acid. Disordered regions that were not modeled include residues 1-2 and 210 (the C-terminus) of the 45-46m2 LC, residues 133-136 and 219-221 (the C-terminus) of the 45-46m2 HC, and residues 302-308 (a short linker substituting for the V3 loop), residues 397-408 (a total of 6 residues from V4) and the 6×-His tag of 93TH057 gp120.

Structures were analyzed and figures were prepared using PyMol as described in Schrödinger, 2011, The PyMOL Molecular Graphics System, the entire contents of which are herein incorporated by reference). Buried surface areas were was calculated using a 1.4 Å probe using Areaimol as implemented in CCP4i package (Collaborative Computational Project Number 4, 1994).

Example 7. Surface Plasmon Resonance (SPR) Measurements. SPR data were collected using a Biacore™ T200 instrument (GE Healthcare). Primary amine coupling chemistry was used to immobilize 1000 resonance units (RU) of the Fabs of NIH45-46, NIH45-46G54W, or 45-46m2 in 10 mM acetate pH 5.0 at a concentration of 0.2 µM to a CM5 sensor chip as described in the Biacore™ manual. Flow channel 1 was mock coupled and served as a blank subtraction channel. gp120 protein was injected as a two-fold dilution series (500 nM to 31.2 nM) at a flow rate of 80 µL/min at 25° C. in 20 mM HEPES, pH 7.0, 150 mM sodium chloride and 0.005% (v/v) P20 surfactant, and sensor chips were regenerated using 10 mM glycine pH 2.5. A 1:1 binding model was fit to the blank-subtracted data using the Biacore™ analysis software to derive kinetic constants ($k_a$ and $k_d$; on- and off-rates) that were subsequently used to calculate affinities (KD; equilibrium dissociation constant).

Example 8. In Vitro Viral Fitness Assays. Replication experiments were carried out as described previously (Neumann et al., 2005, Virology 333:251-262; Sather et al., 2012, J Virol 86:12676-12685, the entire contents of both of which are herein incorporated by reference) utilizing wild type YU-2 and three point mutants in gp120 designated as YU-$2^{N279K}$, YU-$2^{N280D}$, and YU-$2^{A281T}$. The entire gp160 portion of each env variant was inserted into the TN6 replication competent viral backbone, and each construct was transfected into 293T cells to produce infectious virions. Stimulated PBMCs were prepared from whole human blood by Ficoll gradient separation, followed by 72 hours of stimulation by culturing in complete RPMI containing 2 micrograms per ml IL-2 and 3 µg/mL phytohemagglutinin (PHA). 15×10⁶ stimulated PBMCs were infected for 3 hours with viral inoculum containing the equivalent of 12.5 pg of HIV p24. After inoculation, the cells were re-suspended in fresh complete RPMI/IL-2 media at a density of 3×10⁶ cells per ml. At 2-3 day intervals, half of the culture supernatant was harvested and replaced with fresh media. Harvested supernatants were assayed for p24 content by capture ELISA (Zeptometrix, Buffalo, N.Y.). During the culture period, the cultures were monitored to ensure that viability remained above 90%.

Example 9. In Vivo Therapy Experiments. HIV-1 escape experiments were performed in HIV-$1_{YU2}$-infected humanized mice as previously described in Klein et al., 2012, Nature 492:118-122, the entire contents of which are herein incorporated by reference). Briefly, non-obese diabetic Rag1$^{-/-}$ IL2Rγ$^{NULL}$ (NRG) mice (Jackson Laboratory, Bar Harbor, Me.) were reconstituted with fetal liver-derived hematopoietic stem cells and infected with HIV-$1_{YU2}$ (57.5 ng p24). Mice with viral loads >4×10³ copies/ml at 14-17 days post infection were included in treatment experiments. Antibody-treated mice were injected subcutaneously with 1.5 mg 45-46m2 and 1.5 mg 45-46m7 every two days, and mice receiving 10-1074 were injected with 0.5 mg antibody twice per week. All experiments were performed with authorization from the Institutional Review Board and the IACUC at the Rockefeller University.

Example 10. Viral Load Measurements and Sequence Analysis. Viral load and sequence analysis of HIV-1 gp120 were performed as previously described (Klein et al., 2012, supra). Briefly, total RNA was extracted from 100 µl EDTA-plasma using the QiaAmp MinElute Virus Spin Kit as per the manufacturer's protocol. Viral RNA was detected by quantitative reverse-transcriptase PCR using a Stratagene Mx3005P real-time thermal cycler. HIV-specific forward and reverse primer sequences were 5'-GCCTCAATAAA-GCTTGCCTTGA-3' (SEQ ID NO: 47) and 5'-GGCGC-CACTGCTAGAGATTTT-3' (SEQ ID NO: 48), respectively. An internal probe (5'-AAGTAGTGTGTGC-CCGTCTGTTRTKTGACT-3') (SEQ ID NO: 49) contained a 5' 6-carboxyfluorescein reporter and internal/3' ZEN-Iowa Black® FQ double-quencher (Integrated DNA Technologies, Inc., Coralville, Iowa). The reaction mix was prepared using the TaqMan® RNA-to-Ct™ 1-Step kit (Applied Biosystems, Foster City, Calif.). Cycle threshold values were converted to viral loads using an HIV-1 (NL4/3-YU-2) viral preparation of known copy number as a standard.

For gp120 sequencing, viral cDNA was generated from extracted viral RNA (described above) using Superscript III Reverse Transcriptase (Invitrogen) and amplified by gp 120-specific nested PCR using the Expand Long Template PCR System (Roche). PCR amplicons were gel purified, cloned into pCR4-TOPO® (Invitrogen), transformed into One-Shot TOP10® cells (Invitrogen) and sequenced using the insert-flanking primers M13F and M13R. Sequence reads were assembled using Geneious Pro software version 5.5.6 (Biomatters Ltd) and aligned to HIV-$1^{YU2}$ gp120

(accession number M93258). Manual edits to sequence assemblies and alignments were performed in Geneious. gp120 residues were numbered according to HXB2, as determined by the Los Alamos Sequence Locator tool.

As disclosed throughout, a PVL antibody such as NIH45-46 having three substitutions as described herein, results in a potent antibody that is capable of neutralizing a broad range of HIV viral strains. Furthermore, this triple mutant antibody in combination with a second select antibody further increases its potency.

While the present invention has been illustrated and described with reference to certain exemplary embodiments, those of ordinary skill in the art will understand that various modifications and changes may be made to the described embodiments without departing from the spirit and scope of the present invention, as defined in the following claims.

SEQUENCE LISTING SEQ ID NOS; 1-46

| Antibody Name | Light Chain<br>SEQ ID NO: | Heavy Chain<br>SEQ ID NO: |
|---|---|---|
| VRC01 | 1<br>EIVLTQSPGTLSLSPGETAIISCRTSQYGSLAWYQ<br>QRPGQAPRLVIYSGSTRAAGIP<br>DRFSGSRWGPDYNLTISNLESGDFGVYYCQQYE<br>FFGQGTKVQVDIKR | 2<br>QVQLVQSG--<br>GQMKKPGESMRISC<br>RASG --YEFI------<br>DCTLNWIRLAPGKR<br>PEWMGWLKPRGGA<br>VNYARPLQGRVTM<br>TRDVYSDTAFLELR<br>SLTVDDTAVYFCTR<br>GKNCDYNWDFEHW<br>GRGTPVIVSS |
| VRC02 | 3<br>EIVLTQSPGTLSLSPGETAIISCRTSQYGSLAWYQ<br>QRPGQAPRLVIYSGSTRAAGIPDRFSGSRWGPDY<br>NLTIRNLESGDFGLYYCQQYEFFGQGTKVQVDI<br>KR | 4<br>QVQLVQSGGQMKK<br>PGESMRISCQASGYE<br>FIDCTLNWVRLAPG<br>RR<br>PEWMGWLKPRGGA<br>VNYARPLQGRVTM<br>TRDVYSDTAFLELR<br>SLTADDTAVYYCTR<br>GKNCDYNWDFEHW<br>GRGTPVTVSS |
| NIH-45-46 | 5<br>EIVLTQSPATLSLSPGETAIISCRTSQSGSLAWYQ<br>QRPGQAPRLVIYSGSTRAAGIP<br>DRFSGSRWGADYNLSISNLESGDFGVYYCQQYE<br>FFGQGTKVQVDIKRTVA | 6<br>QVRLSQSG--<br>GQMKKPGESMRLSC<br>RASG-- YEFL------<br>NCPINWIRLAPGRRP<br>EWMG<br>WLKPRGGAVNY-<br>ARKFQGRVTMTRD<br>VY----<br>SDTAFLELRSLTSDD<br>TAVYFCTRGKYCTA<br>RDYYNWDFEHWGR<br>GAPVTVSS |
| 3BNC60 | 7<br>DIQMTQSPSSLSARVGDTVTITCQANGYLNWYQ<br>QRRGKAPKLLIYDGSKLERGVP<br>ARFSGRRWGQEYNLTINNLQPEDVATYFCQVYE<br>FIVPGTRLDLKRTVA | 8<br>QVHLSQSG--<br>AAVTKPGASVRVSC<br>EASG --YKIS------<br>DHFIHWWRQAPGQ<br>GLQWVG<br>WINPKTGQPNN-<br>PRQFQGRVSLTRQA<br>SWDFDTYSFYMDLK<br>AVRSDDTAIYFCAR<br>QRS<br>DFWDFDVWGSGTQ<br>VTVSS |

What is claimed is:

1. A composition comprising:

an isolated anti-CD4 binding site (anti-CD4bs) VRC01-related % antibody variant having a heavy chain and a light chain comprising a heavy chain variable region and a light chain variable region, the heavy chain variable region comprising:

a first substitution at position 54 of the heavy chain variable region having the amino acid sequence of SEQ ID NO: 85 according to Kabat numbering of, wherein the first substitution is selected from the group consisting of glycine, histidine, arginine, glutamine, asparagine, lysine, glutamic acid, and aspartic acid, and a second substitution at position 47 of the heavy chain variable region having an amino acid sequence of SEQ ID NO: 85 according to Kabat numbering, wherein the second substitution is selected from valine, isoleucine, and threonine; and the light chain variable region comprising:

a light chain substitution for serine at position 28 of the light chain variable region having the amino acid sequence of SEQ ID NO: 84 according to Kabat numbering.

2. The composition of claim 1, wherein the first substitution is arginine.

3. The composition of claim 1, wherein the anti-CD4bs VRC01-related % antibody variant is 45-46 m2.

4. A pharmaceutical composition comprising the composition of claim 1 or a fragment thereof, and a pharmaceutically acceptable carrier.

5. A method of preventing or treating an HIV infection or an HIV-related disease, the method comprising administering a therapeutically effective amount of the composition of claim 1 to a patient.

6. A method of preventing or treating an HIV infection or an HIV-related disease, the method comprising administering a therapeutically effective c7 amount of a combination of antibodies, the combination of antibodies comprising a first antibody and a second antibody, the first antibody comprising the composition of claim 1 and the second antibody comprising 10-1074 antibody or PG9 antibody.

* * * * *

UNITED STATES PATENT AND TRADEMARK OFFICE
CERTIFICATE OF CORRECTION

| | | |
|---|---|---|
| PATENT NO. | : 12,173,052 B2 | Page 1 of 1 |
| APPLICATION NO. | : 17/500171 | |
| DATED | : December 24, 2024 | |
| INVENTOR(S) | : Ron Diskin et al. | |

It is certified that error appears in the above-identified patent and that said Letters Patent is hereby corrected as shown below:

In the Specification

Column 1, Line 19, should read as follows:
--STATEMENT REGARDING FEDERALLY SPONSORED RESEARCH OR DEVELOPMENT
This invention was made with government support under Grant No. AI100148 and Grant No. AI100663 awarded by the National Institutes of Health. The government has certain rights in the invention.--

Signed and Sealed this
Eleventh Day of February, 2025

Coke Morgan Stewart
*Acting Director of the United States Patent and Trademark Office*